US009238690B2

(12) United States Patent
Setiady et al.

(10) Patent No.: US 9,238,690 B2
(45) Date of Patent: Jan. 19, 2016

(54) NON-ANTAGONISTIC EGFR-BINDING MOLECULES AND IMMUNOCONJUGATES THEREOF

(75) Inventors: Julianto Setiady, Waltham, MA (US); Rajeeva Singh, Framingham, MA (US); Peter U. Park, Somerville, MA (US); Lingyun Rui, Weston, MA (US); Thomas Chittenden, Sudbury, MA (US)

(73) Assignee: ImmunoGen, Inc., Waltham, MA (US)

( * ) Notice: Subject to any disclaimer, the term of this patent is extended or adjusted under 35 U.S.C. 154(b) by 0 days.

(21) Appl. No.: 13/882,059

(22) PCT Filed: Oct. 28, 2011

(86) PCT No.: PCT/US2011/058385
§ 371 (c)(1),
(2), (4) Date: Sep. 3, 2013

(87) PCT Pub. No.: WO2012/058592
PCT Pub. Date: May 3, 2012

(65) Prior Publication Data
US 2014/0023662 A1    Jan. 23, 2014

Related U.S. Application Data

(60) Provisional application No. 61/408,500, filed on Oct. 29, 2010, provisional application No. 61/436,012, filed on Jan. 25, 2011.

(51) Int. Cl.
| | |
|---|---|
| C07K 16/00 | (2006.01) |
| A61K 39/395 | (2006.01) |
| C07K 16/28 | (2006.01) |
| A61K 47/48 | (2006.01) |
| G01N 33/68 | (2006.01) |
| C07K 16/30 | (2006.01) |
| A61K 39/00 | (2006.01) |

(52) U.S. Cl.
CPC ........... *C07K 16/2863* (2013.01); *A61K 47/481* (2013.01); *A61K 47/48384* (2013.01); *A61K 47/48561* (2013.01); *A61K 47/48569* (2013.01); *C07K 16/30* (2013.01); *G01N 33/68* (2013.01); *A61K 2039/505* (2013.01); *C07K 2317/24* (2013.01); *C07K 2317/33* (2013.01); *C07K 2317/73* (2013.01); *C07K 2317/732* (2013.01); *C07K 2317/75* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,256,746 A | 3/1981 | Miyashita et al. |
| 4,294,757 A | 10/1981 | Asai |
| 4,307,016 A | 12/1981 | Asai et al. |
| 4,313,946 A | 2/1982 | Powell et al. |
| 4,315,929 A | 2/1982 | Freedman et al. |
| 4,322,348 A | 3/1982 | Asai et al. |
| 4,331,598 A | 5/1982 | Hasegawa et al. |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,424,219 A | 1/1984 | Hashimoto et al. |
| 4,450,254 A | 5/1984 | Isley et al. |
| 4,563,304 A | 1/1986 | Carlsson et al. |
| 4,943,533 A | 7/1990 | Mendelsohn et al. |
| 5,208,020 A | 5/1993 | Chari et al. |
| 5,416,064 A | 5/1995 | Chari et al. |
| 5,459,061 A | 10/1995 | Sato et al. |
| 5,470,571 A | 11/1995 | Herlyn et al. |
| 5,475,092 A | 12/1995 | Chari et al. |
| 5,558,864 A | 9/1996 | Bendig et al. |
| 5,585,499 A | 12/1996 | Chari et al. |
| 5,731,168 A | 3/1998 | Carter et al. |
| 5,750,373 A | 5/1998 | Garrard et al. |
| 5,756,291 A | 5/1998 | Griffin et al. |
| 5,844,093 A | 12/1998 | Kettleborough et al. |
| 5,846,545 A | 12/1998 | Chari et al. |
| 5,891,996 A | 4/1999 | Mateo de Acosta del Rio et al. |
| 5,942,602 A | 8/1999 | Wels et al. |
| 6,129,915 A | 10/2000 | Wels et al. |
| 6,217,866 B1 | 4/2001 | Schlessinger et al. |
| 6,235,883 B1 | 5/2001 | Jakobovits et al. |
| 6,333,410 B1 | 12/2001 | Chari et al. |
| 6,441,163 B1 | 8/2002 | Chari et al. |
| 6,506,883 B2 | 1/2003 | Meteo de Acosta del Rio et al. |
| 6,716,821 B2 | 4/2004 | Zhao et al. |
| 6,979,726 B1 | 12/2005 | von Hoegen et al. |

(Continued)

FOREIGN PATENT DOCUMENTS

| | | |
|---|---|---|
| EP | 1 033 406 A1 | 9/2000 |
| EP | 2 457 586 A1 | 5/2012 |

(Continued)

OTHER PUBLICATIONS

Paul, Fundamental Immunology, 3rd edition, 1993, pp. 292-295.*
Bendig (1995) Methods: a companion methods in encymology 8: 83-93.*
MacCallum et al. (1996) J. Mol. Biol. 262: 732-745.*
Casset et al. (2003) BBRC 307: 198-205.*
Akashi, Y., et al., "Enhancement of the antitumor activity of ionising radiation by nimotuzumab, a humanised monoclonal antibody to the epidermal growth factor receptor, in non-small cell lung cancer cell lines of differing epidermal growth factor receptor status," *British Journal of Cancer* 98:749-755, Cancer Research UK, United Kingdom (2008).

(Continued)

*Primary Examiner* — Michael Pak
(74) *Attorney, Agent, or Firm* — Sterne, Kessler, Goldstein & Fox P.L.L.C

(57) ABSTRACT

Novel anti-cancer agents, including, but not limited to, antibodies and immunoconjugates, that bind to EGFR are provided. Methods of using the agents, antibodies, or immunoconjugates, such as methods of inhibiting tumor growth are further provided.

38 Claims, 17 Drawing Sheets

(56) References Cited

U.S. PATENT DOCUMENTS

| | | | |
|---|---|---|---|
| 7,132,511 | B2 | 11/2006 | Carr et al. |
| 7,247,301 | B2 | 7/2007 | van de Winkel et al. |
| 7,276,497 | B2 | 10/2007 | Chari et al. |
| 7,368,565 | B2 | 5/2008 | Chari et al. |
| 7,473,796 | B2 | 1/2009 | Chari et al. |
| 7,479,543 | B2 | 1/2009 | Tsuchiya et al. |
| 7,585,857 | B2 | 9/2009 | Chari et al. |
| 7,589,180 | B2 | 9/2009 | Old et al. |
| 7,595,378 | B2 | 9/2009 | van de Winkel et al. |
| 7,598,350 | B2 | 10/2009 | Liu et al. |
| 7,628,986 | B2 | 12/2009 | Weber et al. |
| 7,736,644 | B2 | 6/2010 | Weber et al. |
| 7,749,697 | B2 | 7/2010 | Oleksiewicz et al. |
| 7,780,964 | B2 | 8/2010 | Ellis et al. |
| 7,846,443 | B2 | 12/2010 | Presta et al. |
| 7,887,805 | B2 | 2/2011 | Pedersen et al. |
| 7,892,777 | B2 | 2/2011 | Fisher et al. |
| 7,935,793 | B2 | 5/2011 | Balasa et al. |
| 8,088,387 | B2 | 1/2012 | Steeves et al. |
| 8,101,183 | B2 | 1/2012 | Siadak et al. |
| 8,236,319 | B2 | 8/2012 | Chari et al. |
| 2002/0001587 | A1 | 1/2002 | Erickson et al. |
| 2004/0031072 | A1 | 2/2004 | La Rosa et al. |
| 2004/0259942 | A1 | 12/2004 | Shaw et al. |
| 2005/0107325 | A1 | 5/2005 | Manoharan et al. |
| 2006/0147959 | A1 | 7/2006 | Bell et al. |
| 2006/0233814 | A1 | 10/2006 | Goldmakher et al. |
| 2007/0009972 | A1 | 1/2007 | Chao et al. |
| 2007/0213292 | A1 | 9/2007 | Stoffel et al. |
| 2008/0171040 | A1 | 7/2008 | Ebens et al. |
| 2009/0155282 | A1 | 6/2009 | Weber et al. |
| 2009/0156790 | A1 | 6/2009 | Weber et al. |
| 2009/0175887 | A1 | 7/2009 | Weber et al. |
| 2009/0240038 | A1 | 9/2009 | Weber et al. |
| 2009/0252681 | A1 | 10/2009 | Laeremans et al. |
| 2009/0258442 | A1 | 10/2009 | Polakiewicz et al. |
| 2010/0008929 | A1 | 1/2010 | van de Winkel et al. |
| 2010/0111979 | A1 | 5/2010 | Weber et al. |
| 2010/0166744 | A1 | 7/2010 | Wong |
| 2010/0190247 | A1 | 7/2010 | Lazar et al. |
| 2011/0287036 | A1 | 11/2011 | Matsumura et al. |
| 2012/0156217 | A1 | 6/2012 | Setiady et al. |
| 2013/0131322 | A1 | 5/2013 | Kaneda et al. |
| 2013/0156796 | A1 | 6/2013 | Setiady et al. |

FOREIGN PATENT DOCUMENTS

| | | | |
|---|---|---|---|
| WO | WO 2008/098145 | A1 | 8/2008 |
| WO | WO 2009/030239 | A1 | 3/2009 |
| WO | WO 2009/134976 | A1 | 11/2009 |
| WO | WO 2010/009124 | A2 | 1/2010 |
| WO | WO 2010/022736 | A2 | 3/2010 |
| WO | WO 2010/042904 | A2 | 4/2010 |
| WO | WO 2010/055950 | A1 | 5/2010 |
| WO | WO 2011/145629 | A2 | 11/2011 |
| WO | WO 2012/058588 | A2 | 5/2012 |
| WO | WO 2012/058592 | A2 | 5/2012 |
| WO | WO 2013/078271 | A1 | 5/2013 |

OTHER PUBLICATIONS

Clarke, J., et al., "Duration of chronic toxicity studies for biotechnology-derived pharmaceuticals: Is 6 months still appropriate?" *Regulatory Toxicology and Pharmacology* 50:2-22, Elsevier Inc., United States (2008).

Guo, L., et al., "Studies of Ligand-Induced Site-Specific Phosphorylation of Epidermal Growth Factor Receptor," *J Am Soc Mass Spectrom* 14:1022-1031, American Society for Mass Spectrometry, United States (2003).

Schmiedel, J., et al., "Matuzumab binding to EGFR prevents the conformational rearrangement required for dimerization," *Cancer Cell* 13(4):365-373, Cell Press, United States (2008).

Singh, R. and Erickson, H.K., "Antibody-Cytotoxic Agent Conjugates: Preparation and Characterization," in *Therapeutic Antibodies: Methods and Protocols*, Dimitrov, A.S., Ed., Chapter 23, pp. 445-467, Humana Press, United States (2009).

Talavera, A., et al., "Nimotuzumab, an Antitumor Antibody that Targets the Epidermal Growth Factor Receptor, Blocks Ligand Binding while Permitting the Active Receptor Conformation," *Cancer Res* 69(14):5851-5859, American Association for Cancer Research, United States (2009).

Eurasian Search Report, completed Nov. 25, 2013, in Eurasian Application No. 201390472, Moscow, Russia.

Eurasian Search Report, completed Feb. 7, 2014, in Eurasian Application No. 201390575, Moscow, Russia.

Notice of Allowance, mailed on Nov. 21, 2013, in U.S. Appl. No. 13/284,398, inventors Setiady et al., filed Oct. 28, 2011.

Corrected Notice of Allowance, mailed on Feb. 18, 2014, in U.S. Appl. No. 13/284,398, inventors Setiady et al., filed Oct. 28, 2011.

Kovtun, Y.V., et al., "Antibody-Maytansinoid Conjugates Designed to Bypass Multidrug Resistance," *Cancer Research* 70(6):2528-2537, American Association for Cancer Research, United States (2010).

Maloney, E.M., et al., "Designing Potent Antibody-Maytansinoid Conjugated (AMCs): The Impact of Lysosomal Processing Efficient and Conjugate Linker Selection on Anticancer Activity," 2009 AACR-NCI-EORTC International Conference on Molecular Targets and Cancer Therapeutics, Boston, MA (Nov. 15-19, 2009), Abstract #B120 Poster, American Association for Cancer Research, United States (Nov. 15, 2009).

Ojima, I., et al., "Tumor-Specific Novel Taxoid—Monoclonal Antibody Conjugates," *Journal of Medicinal Chemistry* 45(26):5620-5623, American Chemical Society, United States (2002).

Ojima, I., "Guided Molecular Missiles for Tumor-Targeting Chemotherapy—Case Studies Using the Second Generation Taxoids as Warheads," *Accounts of chemical research* 41(1):108-119, American Chemical Society, United States (2008).

Singh, R., and Maloney, E.K., "Labeling of Antibodies by in Situ Modification of Thiol Groups Generated from Selenol-Catalyzed Reduction of Native Disulfide Bonds," *Analytical Biochemistry* 304(2):147-156, Academic Press, United States (2002).

Wu, X., and Ojima, I., "Tumor Specific Novel Taxoid-Monoclonal Antibody Conjugates," *Current Medicinal Chemistry* 11(4):429-438, Bentham Science Publishers Ltd., Netherlands (2004).

Bardelli, A., and Siena, S., "Molecular Mechanisms of Resistance to Cetuximab and Panitumumab in Colorectal Cancer," *J. Clin. Oncol.* 28(7):1254-1261, American Society of Clinical Oncology, United States (Mar. 2010).

Baselga, J., and Arteaga, C.L., "Critical Update and Emerging Trends in Epidermal Growth Factor Receptor Targeting in Cancer," *J. Clin. Oncol.* 23(11):2445-2459, American Society of Clinical Oncology, United States (Apr. 2005).

DeRoock, W., et al., "Effects of *KRAS, BRAF, NRAS*, and *PIK3CA* mutations on the efficacy of cetuximab plus chemotherapy in chemotherapy-refractory metastatic colorectal cancer: a retrospective consortium analysis," *Lancet Oncol.* 11:753-762, Lancet Pub. Group, England (Aug. 2010).

Gill, G.N., et al, "Monoclonal Anti-epidermal Growth Factor Receptor Antibodies Which Are Inhibitors of Epidermal Growth Factor Binding and Antagonists of Epidermal Growth Factor-stimulated Tyrosine Protein Kinase Activity," *J. Biol. Chem.* 259(12):7755-7760, American Society for Biochemistry and Molecular Biology, England (Jun. 1984).

Goldstein, N.I., et al., "Biological Efficacy of a Chimeric Antibody to the Epidermal Growth Factor Receptor in a Human Tumor Xenograft Model," *Clin. Cancer Res.* 1:1311-1318, American Association for Cancer Research, United States (Nov. 1995).

Li, T., and Perez-Soler, R., "Skin toxicities associated with epidermal growth factor receptor inhibitors," *Targ. Oncol.* 4:107-119, Springer-Verlag, France (2009).

Linardou, H., et al., "Somatic *EGFR* mutations and efficacy of tyrosine kinase inhibitors in NSCLC," *Nat. Rev. Clin. Oncol.* 6:352-366, Macmillian Publishers Limited, England (Jun. 2009).

Paz-Ares, L., et al, "Clinical outcomes in non-small-cell lung cancer patients with *EGFR* mutations: pooled analysis," *J. Cell. Mol. Med.* 14(1-2):51-69, F. Hoffmann—La Roche Ltd., Switzerland (2010).

(56) References Cited

OTHER PUBLICATIONS

Prewett, M., et al., "Mouse-Human Chimeric Anti-Epidermal Growth Factor Receptor Antibody C225 Inhibits the Growth of Human Renal Cell Carcinoma Xenografts in Nude Mice," *Clin. Cancer Res.* 4:2957-2966, American Association for Cancer Research, United States (Dec. 1998).

Stoll, S.W., et al., "EGF receptor signaling inhibits keratinocyte apoptosis: evidence for mediation by Bcl-$X_L$," *Oncogene* 16:1493-1499, Stockton Press, United Kingdom (Mar. 1998).

Widdison, W.C., et al., "Semisynthetic Maytansine Analogues for the Targeted Treatment of Cancer," *J. Med. Chem.* 49:4392-4408, American Chemical Society, United States (2006).

Baselga, J., "Why the Epidermal Growth Factor Receptor? The Rationale for Cancer Therapy," *The Oncologist* 7(suppl 4):2-8, AlphaMed Press, United States (2002).

Carlsson, J., et al., "Protein Thiolation and Reversible Protein-Protein Conjugation," *Biochem. J.* 173:723-737, Portland Press, England (1978).

Friess, T., et al., "Combination Treatment with Erlotinib and Pertuzumab against Human Tumor Xenografts Is Superior to Monotherapy," *Clin Cancer Res* 11(14):5300-5309, American Association for Cancer Research, United States (2005).

Hashida, S., et al., "More Useful Maleimide Compounds for the Conjugation of Fab' to Horseradish Peroxidase through Thiol Groups in the Hinge," *Journal of Applied Biochemistry* 6:56-63, Academic Press, Inc., United States (1984).

Jost, M., et al., "Matrix-independent Survival of Human Keratinocytes through an EGF Receptor/MAPK-Kinase-dependent Pathway," *Molecular Biology of the Cell* 12:1519-1527, The American Society for Cell Biology, United States (2001).

Kamat, V., et al., "Enhanced EGFR inhibition and distinct epitope recognition by EGFR antagonistic mAbs C225 and 425," *Cancer Biology & Therapy* 7(5):726-733, Landes Bioscience, United States (2008).

Kim, S., et al., "E-cadherin promotes EGFR-mediated cell differentiation and MUC5AC mucin expression in cultured human airway epithelial cells," *Am J Physiol Lung Cell Mol Physiol* 289:L1049-L1060, the American Physiological Society, United States (2005).

Kimura, H., et al., "Antibody-dependent cellular cytotoxicity of cetuximab against tumor cells with wild-type or mutant epidermal growth factor receptor," *Cancer Sci* 98(8):1275-1280, Japanese Cancer Association, Japan (2007).

Lammerts van Bueren, J.L., et al., "The antibody zalutumumab inhibits epidermal growth factor receptor signaling by limiting intra- and intermolecular flexibility," *PNAS* 105(16):6109-6114, The National Academy of Sciences of the USA, United States (2008).

Laux, I., et al., "Epidermal growth factor receptor dimerization status determines skin toxicity to HER-kinase targeted therapies,"*British Journal of Cancer* 94:85-92, Cancer Research UK, England (2006).

Liu, F-T, et al., "New Procedures for Preparation and isolation of Conjugates of Proteins and a Synthetic Copolymer of D-Amino Acids and Immunochemical Characterization of Such Conjugates," *Biochemistry* 18:690-697, American Chemical Society, United States (1979).

Modjtahedi, H., et al., "Anti-EGFR Monoclonal Antibodies which Act as EGF, TGFα HB-EGF and BTC Antagonists Block the Binding of Epiregulin to EGFR-Expressing Tumours," *Int. J. Cancer* 75:310-316, Wiley-Liss, Inc., United States (1998).

Mok, T., et al, "A Small Step Towards Personalized Medicine for Non-small Cell Lung Cancer," *Discovery Medicine* 8(43): 227-231, Discovery Medicine, United States (2009).

Mutsaers, A.J., et al., "Dose-Dependent Increases in Circulating TGF-α and Other EGFR Ligands Act As Pharmacodynamic Markers for Optimal Biological Dosing of Cetuximab and Are Tumor Independent," *Clin Cancer Red* 15(7):2397-2405, American Association for Cancer Research, United States (2009).

Nygren, P-A., "Alternative binding proteins: Affibody binding proteins developed from a small three-helix bundle scaffold," *FEBS Journal* 275:2668-2676, The Author Journal compilation, FEBS, England (2008).

Ocvirk, J, "Management of cetuximab-induced skin toxicity with the prophylactic use of topical vitamin K1 cream," *Radiol Oncol* 44(4):256-266, Versita, Slovenia (2010).

Raben, D., et al., "The Effects of Cetuximab Alone and in Combination With Radiation and/or Chemotherapy in Lung Cancer," *Clinical Cancer Research* 11:795-805, American Association for Cancer Research, United States (2005).

Shalaby, M.R., et al., "Development of Humanized Bispecific Antibodies Reactive with Cytotoxic Lymphocytes and Tumor Cells Overexpressing the HER2 Protooncogene," *J. Exp. Med.* 175:217-225, The Rockefeller University Press, United States (1992).

Sheets, M.D., et al., "Efficient construction of a large nonimmune phage antibody library: The production of high-affinity human single-chain antibodies to protein antigens," *Proc. Natl. Acad. Sci. USA* 95:6157-6162, The National Academy of Sciences, United States (1998).

Steiner, P., et al., "Tumor Growth Inhinition with Cetuximab and Chemotherapy in Non-Small Cell Lung Cancer Xenografts Expressing Wild-type and Mutated Epidermal Growth Factor Receptor," *Clin Cancer Res* 13(5):1540-1551, American Association for Cancer Research, United States (2007).

Ullrich, A., et al., "Human epidermal growth factor receptor cDNA sequence and aberrant expression of the amplified gene in A431 epidermoid carcinoma cells," *Nature* 309:418-425, Nature Publishing Group, England (1984).

Yang, X-D, et al., "Eradication of Established Tumours by a Fully Human Monoclonal Antibody to the Epidermal Growth Factor Receptor without Concomitant Chemotherapy,"*Cancer Research* 59:1236-1243, American Association for Cancer Research, United States (1999).

Yarden, Y., and Sliwkowski, M.X., "Untangling the ErbB Signalling Network," *Nature Reviews Molecular Cell Biology* 2:127-137, Macmillan Magazines Ltd, England (2001).

Yoshitake, S., et al., "Conjugation of Glucose Oxidase from *Aspergillus niger* and Rabbit Antibodies Using N-Hydroxysuccinimide Ester of N -(4-Carboxycyclohexylmethyl)-Maleimide," *Eur. J. Biochem.* 101:395-399, Blackwell Science Ltd., England (1979).

NCBI Entrex, GenBank Report, Accession No. AY208307.1, Zhang, J.Q., and Davidson, W.F., Entry Date Mar. 2004.

NCBI Entrex GenBank Report, Accession No. M15225.1, Chua, M.M., et al., Entry Date Apr. 1993.

"UniProt_B4NGM2, GK21222," UniProt.com, accessed at http://www.uniprot.org/uniprot/B4NGM2, accessed on Dec. 5, 2012, 3 pages.

International Search Report for International Application No. PCT/US11/58378, European Patent Office, Netherlands, mailed on Jun. 8, 2012.

International Search Report for International Application No. PCT/US11/58385, European Patent Office, Netherlands, mailed on Jun. 21, 2012.

Sasaki, T., et al., "A Novel ALK Secondary Mutation and EGFR Signaling Cause Resistance to ALK Kinase Inhibitors," *Cancer Res* 71(18):6051-6060, American Association for Cancer Research, United States (2011).

International Search Report for International Application No. PCT/US12/66205, U.S. Patent Offce, United States, mailed on Feb. 26, 2013.

Lamminmaki, U., et al., "Crystal Structure of a recombinant anti-estradiol Fab fragment in complex with 17beta-estradiol,"*J. Biol. Chem.* 276(39): 36687-36694, American Society for Biochemistry and Molecular Biology, United States (2001).

Li, S., et al., " Structural basis for inhibition of the epidermal growth factor receptor by cetuximab," *Cancer Cell* 7:301-311, Cambridge, United States (2005).

MacCallum, R.M., et al., "Antibody—antigen Interactions: Contact Analysis and Binding Site Topography," *J. Mol. Biol.* 262:732-745, Elsevier, England (1996).

Rudikoff, S., et al., "Single amino acid substitution altering antigen-binding specificity," *Proc. Natl. Acad. Sci. USA* 7: 1979-1983, National Academy of the Sciences, United States (1982).

Office Action mailed on Mar. 18, 2013 in U.S. Appl. No. 13/284,398, inventors Setiady et al., filed Oct. 28, 2011.

(56) References Cited

OTHER PUBLICATIONS

Ramakrishnan, M.S., et al., "Nimotuzumab, a promising therapeutic monoclonal for treatment of turmors of epithelial origin," *mAbs* 1(1):41-48, Landes Bioscience, United States (2009).

Skartved, N.J.O., et al., "Preclinical pharmacokinetics and safety of Syn0004: A synergistic antibody mixture directed against epidermal growth factor receptor," Clin. Cancer Res. 17:5962-5972, American Association for Cancer Research, United States (2011).

Takeda, M., et al., "Nimotuzumab, a novel monoclonal antibody to the epidermal growth factor receptor, in the treatment of non-small cell lung cancer," *Lung Cancer: Targets and Therapy* 2:59-67, Dove Medical Press Ltd., United Kingdom (2011).

Willmarth, N.E., et al., "Autocrine and Juxtacrine Effects of Amphiregulin on the Proliferative, Invasive, and Migratory Properties of Normal and Neoplastic Human Mammary Epithelial Cells," *J. Biol. Chem.* 281:37728-37737, The American Society for Biochemistry and Molecular Biology, Inc., United States (2006).

International Preliminary Report on Patentability for International Application No. PCT/US2011/058385, U.S. Patent Office, United States, mailed May 10, 2013.

International Preliminary Report on Patentability for International Application No. PCT/US2011/058378, U.S. Patent Office, United States, mailed May 10, 2013.

Office Action mailed on Aug. 12, 2013 in U.S. Appl. No. 13/284,398, inventors Setiady et al., filed Oct. 28, 2011.

Extended European Search Report for EP Application No. EP 11 83 7196, European Patent Office, The Hague, mailed on Feb. 13, 2015.

Brown, M., et al., "Tolerance to a Single, but Not Multiple, Amino Acid Replacements in Antibody $V_H$ CDR2: A Means of Minimizing B Cell Wastage from Somatic Hypermutation?" *The Journal of Immunology* 156(9):3285-3291, The American Association of Immunologists, Inc., United States (1996).

Fakih, M. and Vincent, M., "Adverse events associated with anti-EGFR therapies for the treatment of metastatic colorectal cancer," *Current Oncology* 17(Suppl.):S18-S30, Multimed, Canada (Jul. 2010).

Milenic, D.E., et al., "Cetuximab: Preclinical Evaluation of a Monoclonal Antibody Targeting EGFR for Radioimmunodiagnostics and Radioimmunotherapeutic Applications," *Cancer Biotherapy & Radiopharmaceuticals* 23(5):619-632, Mary Ann Liebert, Inc., United States (2008).

Winkler, K., et al., "Changing the Antigen Binding Specificity by Single Point Mutations of an Anti-p24 (HIV-1) Antibody," *The Journal of Immunology* 165(8):4505-4514, The American Association of Immunologists, Inc., United States (2000).

Supplementary European Search Report and European Search Opinion for European Application No. EP 11837192, European Patent Office, Germany, mailed on Sep. 19, 2014.

Kalinowski, F.C., et al., "Regulation of Epidermal Growth Factor Receptor Signaling and Erlotinib Sensitivity in Head and Neck Cancer Cells by miR-7," *PLoS One* 7(10):e47067, Public Library of Science, United States (Oct. 2012).

Inukai, M., et al., "Presence of *Epidermal Growth Factor Receptor* Gene T790M Mutation as a Minor Clone in Non-Small Cell Lung Cancer," *Cancer Research* 66(16):7854-7858, American Association for Cancer Research, United States (2006).

Non-Final Office Action mailed Oct. 17, 2014, in U.S. Appl. No. 13/682,948, inventors Setiady, J., et al., filed Nov. 21, 2012.

\* cited by examiner

| Ab clone# | huEGFR Kd | maEGFR Kd |
|---|---|---|
| muEGFR-8 | 6.27E-10 | 4.70E-10 |
| huML66 | 1.00E-09 | 2.00E-09 |
| Cetuximab | 5.66E-10 | 5.50E-11 |
| Panitumumab | 5.72E-10 | 1.20E-10 |

FIGURE 1

Humanization of ML66

A

| ML66-V$_L$ | | |
|---|---|---|
| Kabat position | Rat residue | Human residue |
| 1 | D | D |
| 3 | V | V |
| 5 | T | T |
| 7 | S | S |
| 10 | A | _S_ |
| 11 | L | L |
| 16 | G | G |
| 18 | R | R |
| 19 | V | _A_ |
| 40 | S | _P_ |
| 41 | G | G |
| 42 | Q | Q |
| 45 | K | K |
| 57 | G | G |
| 60 | A | A |
| 67 | S | S |
| 70 | D | D |
| 80 | A | A |
| 81 | D | _E_ |
| 100 | G | _Q_ |
| 103 | N | _K_ |
| 105 | E | E |
| 107 | K | K |
| 108 | R | R |

B

| ML66-V$_H$ | | |
|---|---|---|
| Kabat position | Rat residue | Human residue |
| 1 | Q | Q |
| 3 | Q | Q |
| 5 | K | _Q_ |
| 11 | L | L |
| 13 | Q | _K_ |
| 15 | S | S |
| 16 | Q | _E_ |
| 41 | P | P |
| 42 | G | G |
| 43 | K | K |
| 61 | S | _P_ |
| 62 | V | _S_ |
| 64 | K | K |
| 65 | S | S |
| 74 | S | S |
| 75 | K | K |
| 83 | Q | _T_ |
| 84 | T | _A_ |
| 85 | E | _A_ |
| 105 | Q | Q |
| 108 | M | _L_ |
| 112 | S | S |

FIGURE 2

Humanization alignments

A

```
              1                                                              60
ratML66 VL    DTVLTQSPALAVSPGERVTISCRASESVSTLMHWYQQKSGQQPKLLIYLASHRESGVPAR
huML66 VL     --------S--------A---------------------P--------------------

61                                             107
ratML66 VL    FSGSGSGTDFTLTIDPMEADDTATYYCQQSRHDPWTFGGGTKLELKR
huML66 VL     ------------------E-----------------Q--K------
```

B

```
              1                                                              60
ratML66 VH    QVQLKESGPGLVQPSQTLSLTCTVSGLSLASNSVSWIRQPPGKGLEWMGVIWHGGTDYN
huML66 VH     ----Q-------K--E--------------------------------------------

61                                                116
ratML66 VH    SVIKSRLSISRDTSKSQVFLKMNSLQTEDTAMYFCVRKGGIYFDYWGQGVMVTVSS
huML66 VH     PS----------------------TAA---------------------L------
```

FIGURE 3

A.
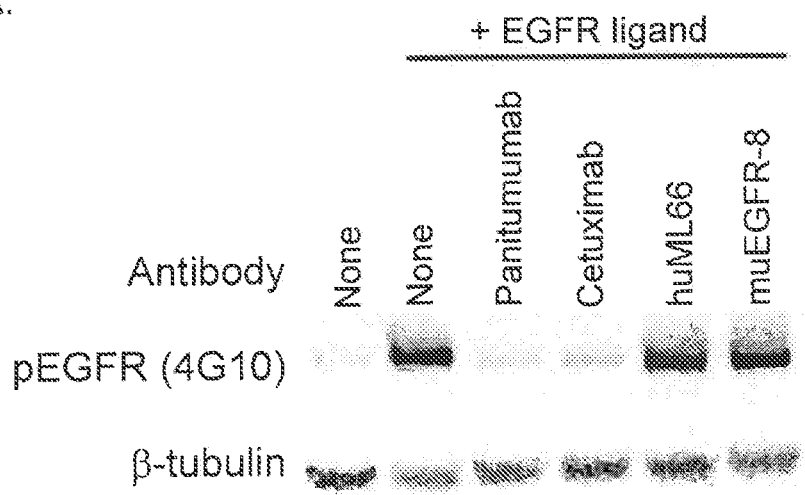
B.
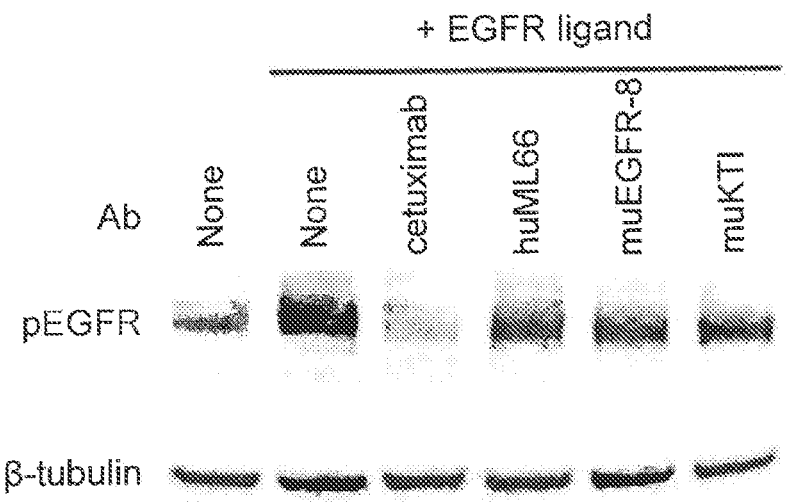
FIGURE 5

NON-ANTAGONISTIC EGFR-BINDING MOLECULES AND IMMUNOCONJUGATES THEREOF

FIELD OF THE INVENTION

The present invention generally relates to antibodies, antigen-binding fragments thereof, polypeptides, and immunoconjugates that bind to EGFR. In particular, it relates to anti-EGFR antibodies and fragments thereof which do not inhibit EGFR signaling but are highly cytotoxic to EGFR overexpressing tumor cells as immunoconjugates. The present invention also relates to methods of using such EGFR-binding molecules for diagnosing and treating diseases, such as malignancies.

BACKGROUND OF THE INVENTION

The epidermal growth factor receptor (EGFR or ErbB1 or HER1) is a member of the human epidermal growth factor receptor (HER) family of receptor tyrosine kinases (RTK) which includes HER2 (ErbB2), HER3 (ErbB3) and HER4 (ErbB4). These RTKs share a homologous structure that consists of a ligand-binding extracellular domain (ECD), a single span transmembrane domain and an intracellular domain that contain catalytic-kinase domain and a C-terminal tail. HER kinase signaling is initiated by the binding of extracellular ligand that induces receptor dimerization and transphosphorylation of the intracellular regions. These events generate the initial signal leading to activation of numerous downstream signaling pathways that are critical for cell proliferation and survival.

EGFR is over-expressed in many malignant tumor types of epithelial cell origin such as head and neck, colorectal, lung, ovarian, renal, pancreatic, skin and other solid tumors. EGFR-mediated signaling pathways play a significant role in the progression of tumor growth and metastases, making EGFR a good target for tumor therapy (Baselga, Oncologist, 7:2-8 (2002), Yarden and Sliwkowski, Nat Rev Mol Cell Biol, 2:127-137 (2001)). At present, four EGFR targeting agents including two small molecules tyrosine kinase inhibitors (TKIs) (erlotinib (Tarceva) and gefitinib (Iressa)) and two naked monoclonal antibodies (cetuximab (Erbitux) and panitumumab (Vectibix)) have been approved for treatment of colorectal cancer, pancreatic cancer, head and neck cancer, and non small cell lung cancer. These anti-EGFR agents strongly inhibit EGFR activation and downstream signaling. The TKIs compete with ATP for binding to the EGFR's intracellular kinase domain (Baselga and Arteaga, J Clin Oncol, 23:2445-2459 (20005)), whereas the two monoclonal antibodies compete with the EGFR ligands for binding to the receptor (Gill et al., J Biol Chem, 259:7755-7760 (1984), Goldstein et al., Clin Cancer Res, 1:1311-1318 (1995), Prewett et al., Clin Cancer Res, 4:2957-2966 (1998)).

Anti-EGFR therapies are not perfect. Inhibition of EGFR signaling is only effective in certain tumor type. For example, the efficacy of anti-EGFR antibodies is significantly reduced in colorectal cancer patients with KRAS, BRAF, PIK3CA and PTEN mutations (De Roock et al., Lancet Oncol, 11:753-762 (2010), Bardelli and Sienna, J Clin Oncol, 28: 1254-1261 (2010)). Additionally, the activity of small molecule EGFR inhibitors is limited to NSCLC patients with activating EGFR mutations (Linardou et al., Nat Rev Clin Oncol, 6: 352-366 (2009), Paz-Ares et al., J Cell Mol Med, 14: 51-69 (2009), Mok et al., Discov Med, 8: 227-231 (2009)). EGFR therapies also result in skin toxicity. EGFR expression in normal basal epithelial cells of the skin plays a crucial role in normal development and physiology of epidermis, and inhibition of EGFR signaling causes various skin toxicities including acneiform skin rash, skin dryness, pruritus, paronychia, hair abnormality, mucositis and increased growth of the eyelashes or facial hair (reviewed in Li and Perez-Soler, Targ Oncol 4:107-119 (2009)). Although rarely life-threatening, the skin toxicities cause significant physical and phycho-social discomfort that decrease the patient's life quality. Additionally, in around 10% of patients, the skin toxicity is so severe that it requires treatment interruption or discontinuation that impairs the clinical outcomes of EGFR inhibitors.

Accordingly, the need exists for improved anti-EGFR therapy which is harmless to normal tissues but still very effective in treating EGFR-overexpressing malignant tumors. To address this particular need, the present invention focuses on unique EGFR antibodies that do not inhibit EGFR signaling but are highly cytotoxic to EGFR-expressing tumor cells as immunoconjugates.

BRIEF SUMMARY OF THE INVENTION

The present invention generally relates to antibodies, antigen-binding fragments thereof, polypeptides, and immunoconjugates that bind to EGFR. In particular, it relates to anti-EGFR antibodies and fragments thereof which do not inhibit EGFR signaling but are highly cytotoxic to EGFR overexpressing tumor cells as immunoconjugates. The present invention also relates to methods of using such EGFR-binding molecules for diagnosing and treating diseases, such as malignancies.

Thus, in one embodiment, the invention is directed to a non-antagonistic antibody or antigen binding fragment thereof that specifically binds to human EGFR, wherein said antibody has at least one characteristic selected from the group consisting of: (a) does not inhibit epidermal growth factor (EGF)-induced EGFR phosphorylation in MDA-MB468 cell line and human primary keratinocytes at 10 µg/ml or lower, (b) does not inhibit binding of transforming growth factor alpha (TGFα) to EGFR in MDA-MB468 cell line at 100 nM or lower, (c) does not inhibit no more than 20% of ligand-induced proliferation of keratinocytes and MCF-10A epithelial cells at 100 nM or lower, (d) does not inhibit no more than 20% of basal proliferation of EGFR expressing NCI-H292 and NCI-H322M tumor cells at 100 nM or lower and (e) does not inhibit no more than 30% binding of cetuximab and 528 antibody in A431 cell line at 100 nM or lower.

In another embodiment, the antibody or antigen binding fragment has at least two characteristics selected from the group consisting of: (a) does not inhibit epidermal growth factor (EGF)-induced EGFR phosphorylation in MDA-MB468 cell line and human primary keratinocytes at 10 ug/ml or lower, (b) does not inhibit binding of TGFα to EGFR in MDA-MB468 cell line at 100 nM or lower, (c) does not inhibit no more than 20% of ligand-induced proliferation of keratinocytes and MCF-10A epithelial cells at 100 nM or lower, (d) does not inhibit no more than 20% of basal proliferation of EGFR expressing NCI-H292 and NCI-H322M tumor cells at 100 nM or lower and (e) does not inhibit no more than 30% binding of cetuximab and 528 antibody in A431 cell line at 100 nM or lower.

In another embodiment, the antibody or antigen binding fragment has at least three characteristics selected from the group consisting of: (a) does not inhibit epidermal growth factor (EGF)-induced EGFR phosphorylation in MDA-MB468 cell line and human primary keratinocytes at 10 ug/ml or lower, (b) does not inhibit binding of TGFα to EGFR in MDA-MB468 cell line at 100 nM or lower, (c) does not inhibit no more than 20% of ligand-induced proliferation of keratinocytes and MCF-100A epithelial cells at 100 nM or lower, (d) does not inhibit no more than 20% of basal proliferation of EGFR expressing NCI-H292 and NCI-H322M tumor cells at 100 nM or lower and (e) does not inhibit no more than 30% binding of cetuximab and 528 antibody in A431 cell line at 100 nM or lower.

In another embodiment, the antibody or antigen binding fragment has at least four characteristics selected from the group consisting of: (a) does not inhibit epidermal growth factor (EGF)-induced EGFR phosphorylation in MDA-MB468 cell line and human primary keratinocytes at 10 ug/ml or lower, (b) does not inhibit binding of TGFα to EGFR in MDA-MB468 cell line at 100 nM or lower, (c) does not inhibit no more than 20% of ligand-induced proliferation of keratinocytes and MCF-100A epithelial cells at 100 nM or lower, (d) does not inhibit no more than 20% of basal proliferation of EGFR expressing NCI-H292 and NCI-H322M tumor cells at 100 nM or lower and (e) does not inhibit no more than 30% binding of cetuximab and 528 antibody in A431 cell line at 100 nM or lower.

In another embodiment, the antibody or antigen binding fragment has at least five characteristics selected from the group consisting of: (a) does not inhibit epidermal growth factor (EGF)-induced EGFR phosphorylation in MDA-MB468 cell line and human primary keratinocytes at 10 ug/ml or lower, (b) does not inhibit binding of TGFα to EGFR in MDA-MB468 cell line at 100 nM or lower, (c) does not inhibit no more than 20% of ligand-induced proliferation of keratinocytes and MCF-10A epithelial cells at 100 nM or lower, (d) does not inhibit no more than 20% of basal proliferation of EGFR expressing NCI-H292 and NCI-H322M tumor cells at 100 nM or lower and (e) does not inhibit no more than 30% binding of cetuximab and 528 antibody in A431 cell line at 100 nM or lower.

In another embodiment the invention is directed to a non-antagonistic antibody or antigen binding fragment thereof that specifically binds to human EGFR, wherein said antibody (a) does not inhibit epidermal growth factor (EGF)-induced EGFR phosphorylation in MDA-MB468 cell line and human primary keratinocytes at 10 ug/ml or lower, (b) does not inhibit binding of TGFα to EGFR in MDA-MB468 cell line at 100 nM or lower, (c) does not inhibit no more than 20% of ligand-induced proliferation of keratinocytes and MCF-10A epithelial cells at 100 nM or lower, (d) does not inhibit no more than 20% of basal proliferation of EGFR expressing NCI-H292 and NCI-H322M tumor cells at 100 nM or lower, and (e) does not inhibit no more than 30% binding of cetuximab and 528 antibody in A431 cell line at 100 nM or lower.

In another embodiment, the invention is directed to a non-antagonistic antibody or antigen binding fragment thereof that specifically binds to human EGFR, wherein said antibody (a) does not inhibit epidermal growth factor (EGF)-induced EGFR phosphorylation in MDA-MB468 cell line and human primary keratinocytes at 10 ug/ml or lower, (b) does not inhibit binding of TGFα to EGFR in MDA-MB468 cell line at 100 nM or lower, (c) does not inhibit no more than 20% of ligand-induced proliferation of keratinocytes and MCF-10A epithelial cells at 100 nM or lower, (d) does not inhibit no more than 20% of basal proliferation of EGFR expressing NCI-H292 and NCI-H322M tumor cells at 100 nM or lower and (e) does not inhibit no more than 30% binding of cetuximab and 528 antibody in A431 cell line at 100 nM or lower, and (f) does not induce EGFR phosphylation in absence of exogenous EGF in MDA-MB468 cell line.

In another embodiment, the invention is directed to a non-antagonistic antibody or antigen binding fragment thereof that specifically binds to human EGFR, wherein said antibody (a) does not inhibit epidermal growth factor (EGF)-induced EGFR phosphorylation in MDA-MB468 cell line and human primary keratinocytes at 10 ug/ml or lower, (b) does not inhibit binding of TGFα to EGFR in MDA-MB468 cell line at 100 nM or lower, (c) does not inhibit no more than 20% of ligand-induced proliferation of keratinocytes and MCF-10A epithelial cells at 100 nM or lower, (d) does not inhibit no more than 20% of basal proliferation of EGFR expressing NCI-H292 and NCI-H322M tumor cells at 100 nM or lower and (e) does not inhibit no more than 30% binding of cetuximab and 528 antibody in A431 cell line at 100 nM or lower, and (f) does induce EGFR phosphylation in absence of exogenous EGF in MDA-MB468 cell line.

In another embodiment, the antibody or antigen binding fragment thereof comprises (a) a VH sequence at least 90% identical to a reference VH sequence selected from the group consisting of SEQ ID NOs: 17-20; and (b) a VL sequence at least 90% identical to a reference VL sequence selected from the group consisting of SEQ ID NOs:21-24. In a further embodiment, the antibody or antigen binding fragment thereof comprises VH and VL sequences are at least 95% identical to the reference VH and VL sequences. In another embodiment, the antibody or antigen binding fragment thereof comprises VH and VL sequences are at least 99% identical to the reference VH and VL sequences. In yet another embodiment, the antibody or antigen binding fragment thereof comprises (a) a VH sequence selected from the group consisting of SEQ ID NOs: 17-20 and (b) a VL sequence selected from the group consisting of SEQ ID NOs: 21-24.

In one embodiment, the antibody or antigen binding fragment thereof comprises SEQ ID NO: 17 and SEQ ID NO:21. In another embodiment, the antibody or antigen binding fragment thereof comprises SEQ ID NO: 18 and SEQ ID NO:22. In another embodiment, the antibody or antigen binding fragment thereof comprises SEQ ID NO: 19 and SEQ ID NO:23. In another embodiment, the antibody or antigen binding fragment thereof comprises SEQ ID NO:20 and SEQ ID NO:24.

In one embodiment, the invention provides an antibody or antigen binding fragment thereof that specifically binds to the same human EGFR epitope an antibody selected from the group consisting of: (a) an antibody comprising the VH polypeptide of SEQ ID NO: 17 and the VL polypeptide of SEQ ID NO:21; (b) an antibody comprising the VH polypeptide of SEQ ID NO: 18 and the VL polypeptide of SEQ ID NO:22; (c) an antibody comprising the VH polypeptide of SEQ ID NO: 19 and the VL polypeptide of SEQ ID NO:23; and (d) an antibody comprising the VH polypeptide of SEQ ID NO:20 and the VL polypeptide of SEQ ID NO:24.

In one embodiment, the invention provides an antibody or antigen binding fragment thereof that competitively inhibits binding of a reference antibody to human EGFR, wherein said reference antibody is selected from the group consisting of: (a) an antibody comprising the VH polypeptide of SEQ ID NO:17 and the VL polypeptide of SEQ ID NO:21; (b) an antibody comprising the VH polypeptide of SEQ ID NO: 18 and the VL polypeptide of SEQ ID NO:22; (c) an antibody comprising the VH polypeptide of SEQ ID NO: 19 and the VL polypeptide of SEQ ID NO:23; and (d) an antibody comprising the VH polypeptide of SEQ ID NO:20 and the VL polypeptide of SEQ ID NO:24.

In one embodiment, the invention provides an antibody or antigen binding fragment thereof that specifically binds to human EGFR, wherein the antibody or antigen binding fragment thereof comprises: (a) an immunoglobulin heavy chain variable region comprising CDR1, CDR2, and CDR3, which, with the exception of 1, 2, or 3 conservative amino acid substitutions, are respectively identical to the reference heavy chain CDR1, CDR2, and CDR3 sequences of SEQ ID NO: 1, SEQ ID NOs: 2, and SEQ ID NO: 3; and (b) an immunoglobulin a light chain variable region comprising CDR1, CDR2, and CDR3, which, with the exception of 1, 2, or 3 conservative amino acid substitutions, are respectively identical to the reference light chain CDR1, CDR2, and CDR3 sequences of SEQ ID NO: 11, SEQ ID NOs: 12, and SEQ ID NO: 13. In another embodiment, the antibody or antigen binding fragment thereof comprises: (a) an immunoglobulin heavy chain variable region comprising CDR1, CDR2, and CDR3, which are respectively identical to the reference heavy chain CDR1, CDR2, and CDR3 sequences of SEQ ID NO: 1, SEQ ID NOs: 2, and SEQ ID NO: 3; and (b) an immunoglobulin a light chain variable region comprising CDR1, CDR2, and CDR3, which are respectively identical to the reference light chain CDR1, CDR2, and CDR3 sequences of SEQ ID NO: 11, SEQ ID NOs: 12, and SEQ ID NO: 13.

In one embodiment, the invention provides an antibody or antigen binding fragment thereof that specifically binds to human EGFR, wherein the antibody or antigen binding fragment thereof comprises: (a) an immunoglobulin heavy chain variable region comprising CDR1, CDR2, and CDR3, which, with the exception of 1, 2, or 3 conservative amino acid substitutions, are respectively identical to the reference heavy chain CDR1, CDR2, and CDR3 sequences of SEQ ID NO: 1, SEQ ID NOs: 4, and SEQ ID NO: 3; and (b) an immunoglobulin a light chain variable region comprising CDR1, CDR2, and CDR3, which, with the exception of 1, 2, or 3 conservative amino acid substitutions, are respectively identical to the reference light chain CDR1, CDR2, and CDR3 sequences of SEQ ID NO: 11, SEQ ID NOs: 12, and SEQ ID NO: 13. In another embodiment, the antibody or antigen binding fragment thereof comprises: (a) an immunoglobulin heavy chain variable region comprising CDR1, CDR2, and CDR3, which are respectively identical to the reference heavy chain CDR1, CDR2, and CDR3 sequences of SEQ ID NO: 1, SEQ ID NOs: 4, and SEQ ID NO: 3; and (b) an immunoglobulin a light chain variable region comprising CDR1, CDR2, and CDR3, which are respectively identical to the reference light chain CDR1, CDR2, and CDR3 sequences of SEQ ID NO: 11, SEQ ID NOs: 12, and SEQ ID NO: 13.

In one embodiment, the invention provides an antibody or antigen binding fragment thereof that specifically binds to human EGFR, wherein the antibody or antigen binding fragment thereof comprises: (a) an immunoglobulin heavy chain variable region comprising CDR1, CDR2, and CDR3, which, with the exception of 1, 2, or 3 conservative amino acid substitutions, are identical to the reference heavy chain CDR1, CDR2, and CDR3 sequences of SEQ ID NO:1, SEQ ID NOs: 5, and SEQ ID NO: 3; and (b) an immunoglobulin a light chain variable region comprising CDR1, CDR2, and CDR3, which, with the exception of 1, 2, or 3 conservative amino acid substitutions, are respectively identical to the reference light chain CDR1, CDR2, and CDR3 sequences of SEQ ID NO: 11, SEQ ID NOs: 12, and SEQ ID NO: 13. In another embodiment, the antibody or antigen binding fragment comprises: (a) an immunoglobulin heavy chain variable region comprising CDR1, CDR2, and CDR3, which are respectively identical to the reference heavy chain CDR1, CDR2, and CDR3 sequences of SEQ ID NO:1, SEQ ID NOs: 5, and SEQ ID NO: 3; and (b) an immunoglobulin a light chain variable region comprising CDR1, CDR2, and CDR3, which are respectively identical to the reference light chain CDR1, CDR2, and CDR3 sequences of SEQ ID NO: 11, SEQ ID NOs: 12, and SEQ ID NO: 13.

In one embodiment, the invention provides an antibody or antigen binding fragment thereof that specifically binds to human EGFR, wherein the antibody or antigen binding fragment thereof comprises: (a) an immunoglobulin heavy chain variable region comprising CDR1, CDR2, and CDR3, which, with the exception of 1, 2, or 3 conservative amino acid substitutions, are respectively identical to the reference heavy chain CDR1, CDR2, and CDR3 sequences of SEQ ID NO: 6, SEQ ID NOs: 7, and SEQ ID NO: 8; and (b) an immunoglobulin a light chain variable region comprising CDR1, CDR2, and CDR3, which, with the exception of 1, 2, or 3 conservative amino acid substitutions, are respectively identical to the reference light chain CDR1, CDR2, and CDR3 sequences of SEQ ID NO: 14, SEQ ID NOs: 15, and SEQ ID NO: 16. In another embodiment, the antibody or antigen binding fragment comprises: (a) an immunoglobulin heavy chain variable region comprising CDR1, CDR2, and CDR3, which are respectively identical to the reference heavy chain CDR1, CDR2, and CDR3 sequences of SEQ ID NO: 6, SEQ ID NOs: 7, and SEQ ID NO: 8; and (b) an immunoglobulin a light chain variable region comprising CDR1, CDR2, and CDR3, which are respectively identical to the reference light chain CDR1, CDR2, and CDR3 sequences of SEQ ID NO: 14, SEQ ID NOs: 15, and SEQ ID NO: 16.

In one embodiment, the invention provides an antibody or antigen binding fragment thereof that specifically binds to human EGFR, wherein the antibody or antigen binding fragment thereof comprises: (a) an immunoglobulin heavy chain variable region comprising CDR1, CDR2, and CDR3, which, with the exception of 1, 2, or 3 conservative amino acid substitutions, are respectively identical to the reference heavy chain CDR1, CDR2, and CDR3 sequences of SEQ ID NO: 6, SEQ ID NOs: 9, and SEQ ID NO: 8; and (b) an immunoglobulin a light chain variable region comprising CDR1, CDR2, and CDR3, which, with the exception of 1, 2, or 3 conservative amino acid substitutions, are respectively identical to the reference light chain CDR1, CDR2, and CDR3 sequences of SEQ ID NO: 14, SEQ ID NOs: 15, and SEQ ID NO: 16. In another embodiment, the antibody or antigen binding fragment comprises: (a) an immunoglobulin heavy chain variable region comprising CDR1, CDR2, and CDR3, which are respectively identical to the reference heavy chain CDR1, CDR2, and CDR3 sequences of SEQ ID NO: 6, SEQ ID NOs: 9, and SEQ ID NO: 8; and (b) an immunoglobulin a light chain variable region comprising CDR1, CDR2, and CDR3, which are respectively identical to the reference light chain CDR1, CDR2, and CDR3 sequences of SEQ ID NO: 14, SEQ ID NOs: 15, and SEQ ID NO: 16.

In one embodiment, the invention provides an antibody or antigen binding fragment thereof that specifically binds to human EGFR, wherein the antibody or antigen binding fragment thereof comprises: (a) an immunoglobulin heavy chain variable region comprising CDR1, CDR2, and CDR3, which, with the exception of 1, 2, or 3 conservative amino acid substitutions, are respectively identical to the reference heavy chain CDR1, CDR2, and CDR3 sequences of SEQ ID NO: 6, SEQ ID NOs: 10, and SEQ ID NO: 8; and (b) an immunoglobulin a light chain variable region comprising CDR1, CDR2, and CDR3, which, with the exception of 1, 2, or 3 conservative amino acid substitutions, are respectively identical to the reference light chain CDR1, CDR2, and CDR3 sequences of SEQ ID NO: 14, SEQ ID NOs: 15, and SEQ ID NO: 16. In another embodiment, the antibody or antigen binding fragment of claim 27, which comprises: (a) an immunoglobulin heavy chain variable region comprising CDR1, CDR2, and CDR3, which are respectively identical to the reference heavy chain CDR1, CDR2, and CDR3 sequences of SEQ ID NO: 6, SEQ ID NOs: 10, and SEQ ID NO: 8; and (b) an immunoglobulin a light chain variable region comprising CDR1, CDR2, and CDR3, which are respectively identical to the reference light chain CDR1, CDR2, and CDR3 sequences of SEQ ID NO: 14, SEQ ID NOs: 15, and SEQ ID NO: 16.

In one embodiment, the antibody or antigen binding fragment of the invention is murine, non-human, humanized, chimeric, resurfaced, or human. In another embodiment, the antibody or antigen binding fragment thereof is a full length antibody. In another embodiment, the antibody or antigen binding fragment thereof is an antigen binding fragment. In another embodiment, the antibody or antigen binding fragment thereof comprises a Fab, Fab', F(ab')2, Fd, single chain Fv or scFv, disulfide linked Fv, V-NAR domain, IgNar, intrabody, IgGΔCH2, minibody, F(ab')3, tetrabody, triabody, diabody, single-domain antibody, DVD-Ig, Fcab, mAb2, (scFv)2, or scFv-Fc.

The invention also provides a polypeptide comprising the VH and VL sequences described herein.

In one embodiment, the invention provides an antibody or polypeptide that binds both human and macaque EGFR with a substantially similar binding affinity. In one embodiment, the antibody or polypeptide binds to human and macaque EGFR with a Kd of about 1.0 to about 10 nM. In another embodiment, the antibody or polypeptide of binds to human and macaque EGFR with a Kd of about 1.0 nM or better. In another embodiment, binding affinity is measured by flow cytometry, Biacore, or radioimmunoassay.

In one embodiment, the invention provides an isolated cell producing an antibody or antigen binding fragment thereof, or polypeptide described herein.

In one embodiment, the invention provides a method of making an antibody or antigen binding fragment thereof, or polypeptide described herein comprising (a) culturing a cell that expresses the antibody, antigen-binding fragment thereof, or polypeptide, and (b) isolating said antibody, antigen-binding fragment thereof, or polypeptide from said cultured cell. In one embodiment the cell is a eukaryotic cell.

In one embodiment, the invention provides an immunoconjugate having the formula (A)-(L)-(C), wherein: (A) is an antibody or antigen binding fragment thereof, or polypeptide described herein; (L) is a linker; and (C) is a cytotoxic agent; and wherein said linker (L) links (A) to (C). In another embodiment, the linker is selected from the group consisting of a cleavable linker, a non-cleavable linker, a hydrophilic linker, and a dicarboxylic acid based linker. In another embodiment, the linker is a non-cleavable linker. In another embodiment, the linker is selected from the group consisting: N-succinimidyl 4-(2-pyridyldithio)pentanoate (SPP); N-succinimidyl 4-(2-pyridyldithio)butanoate (SPDB) or N-succinimidyl 4-(2-pyridyldithio)-2-sulfobutanoate (sulfo-SPDB); N-succinimidyl 4-(maleimidomethyl)cyclohexanecarboxylate (SMCC); N-sulfosuccinimidyl 4-(maleimidomethyl)cyclohexanecarboxylate (sulfoSMCC); N-succinimidyl-4-(iodoacetyl)-aminobenzoate (SIAB); and N-succinimidyl-[(N-maleimidopropionamido)-tetraethyleneglycol]ester (NHS-PEG4-maleimide). In a further embodiment, the linker is N-succinimidyl-[(N-maleimidopropionamido)-tetraethyleneglycol]ester (NHS-PEG4-maleimide).

In another embodiment, the immunoconjugate comprises a cytotoxic agent selected from the group consisting of a maytansinoid, maytansinoid analog, doxorubicin, a modified doxorubicin, benzodiazepine, taxoid, CC-1065, CC-1065 analog, duocarmycin, duocarmycin analog, calicheamicin, dolastatin, dolastatin analog, aristatin, tomaymycin derivative, and leptomycin derivative or a prodrug of the agent. In another embodiment, the cytotoxic agent is a maytansinoid. In a further embodiment, the cytotoxic agent is N(2')-deacetyl-N(2')-(3-mercapto-1-oxopropyl)-maytansine (DM1) or N(2')-deacetyl-N2-(4-mercapto-4-methyl-1-oxopentyl)-maytansine (DM4).

In one embodiment, the invention provides a pharmaceutical composition comprising an antibody or antigen binding fragment thereof, or polypeptide described herein, or an immunoconjugate described herein and a pharmaceutically acceptable carrier. In another embodiment, the pharmaceutical composition comprises a second anti-cancer agent.

In one embodiment, the invention provides a diagnostic reagent comprising an antibody or antigen binding fragment thereof, polypeptide, or immunoconjugate of the invention which is labeled. In one embodiment, the label is selected from the group consisting of a radiolabel, a fluorophore, a chromophore, an imaging agent and a metal ion.

In one embodiment, the invention provides a kit comprising an antibody or antigen binding fragment thereof, polypeptide, or immunoconjugate described herein.

In one embodiment, the invention provides a method for inhibiting the growth of a cell expressing EGFR comprising contacting the cell with an immunoconjugate or the pharmaceutical composition described herein. In another embodiment, the cell is a tumor cell.

In one embodiment, the invention provides a method for treating a patient having a neoplasm comprising administering to said patient a therapeutically effective amount of an immunoconjugate or pharmaceutical composition described herein. In another embodiment, the neoplasm is selected from the group consisting of: abdominal, bone, breast, digestive system, liver, pancreas, peritoneum, adrenal, parathyroid, pituitary, testicles, ovary, thymus, thyroid, eye, head and neck, central nervous system, peripheral nervous system, lymphatic system, pelvic, skin, soft tissue, spleen, thoracic region, and urogenital system. In another embodiment, the method comprises administering a second anti-cancer agent to the subject. In a further embodiment, the second anti-cancer agent is a chemotherapeutic agent.

In one embodiment, the invention provides a method for treating a cell proliferative disorder in a patient comprising administering to said patient a therapeutically effective amount of an immunoconjugate or pharmaceutical composition described herein. In another embodiment, the cell proliferative disorder is selected from the group consisting of: adrenal cortex hyperplasia (Cushing's disease), congenital adrenal hyperplasia, endometrial hyperplasia, benign prostatic hyperplasia, breast hyperplasia, intimal hyperplasia, focal epithelial hyperplasia (Heck's disease), sebaceous hyperplasia, compensatory liver hyperplasia, and any other cell proliferation disease, besides neoplasia.

In one embodiment, the invention provides an isolated polynucleotide comprising a sequence that encodes a polypeptide at least 90% identical to a sequence selected from the group consisting of SEQ ID NOs: 17-28. In another embodiment, the sequence is at least 95% identical a sequence selected from the group consisting of SEQ ID NOs: 17-28. In a further embodiment, the sequence is at least 99% identical to a sequence selected from the group consisting of SEQ ID NOs: 17-28, In one embodiment, the invention provides an isolated polynucleotide which comprises a sequence that is at least 90% identical to SEQ ID NOs: 29-40. In another embodiment, the polynucleotide comprises a sequence that is at least 95% identical to SEQ ID NOs: 29-40. In a further embodiment, the polynucleotide comprises a sequence that is at least 99% identical to SEQ ID NOs: 29-40. In yet another embodiment, the invention provides an isolated polynucleotide which comprises a sequence selected from the group consisting of SEQ ID NOs: 17-40. In another embodiment, the invention provides a vector comprising the polynucleotides described herein. In another embodiment, the invention provides a host cell comprising the vectors described herein.

BRIEF DESCRIPTION OF THE DRAWINGS/FIGURES

FIG. 1 shows a table describing the binding affinity of the indicated anti-EGFR antibodies to human EGFR (huEGFR) and monkey EGFR (maEGFR) antigen.

FIG. 2 shows tables depicting specific framework surface residue changes in resurfacing of ML66 VL (A) and VH (B).

FIG. 3 shows alignment of the resurfaced sequences and murine counterparts of ML66 VL (A) and VH (B).

FIG. 5 shows Western blot data depicting the effect of the indicated anti-EGFR antibodies in ligand-induced EGFR phosphorylation in MDA-MB468 cells (A) and in human primary keratinocytes (B).

DETAILED DESCRIPTION OF THE INVENTION

Figure 4:
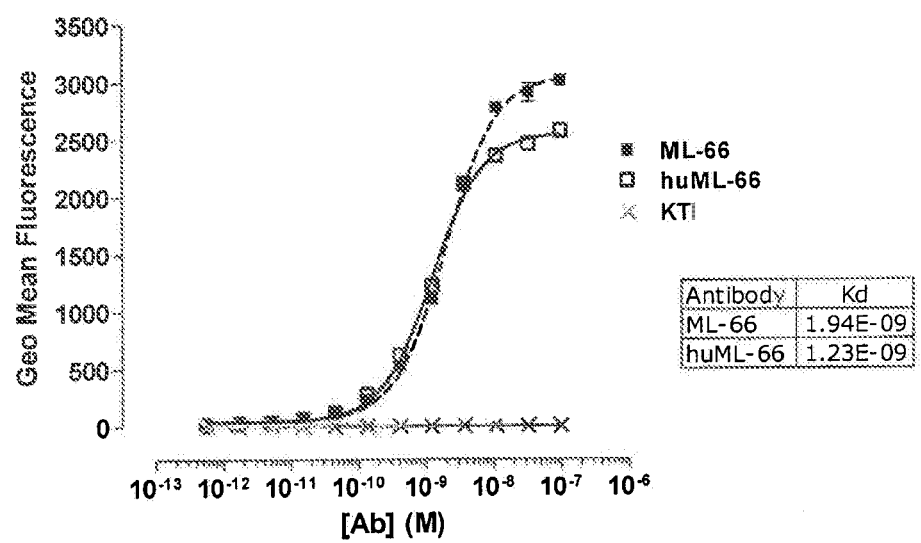
FIG. 4 shows a line graph depicting the binding of ML.-66 (filled squares) and huML-66 (open squares) to MDA-MB468 cells.

The present invention provides a new class of EGFR binding molecules which have non-antagonist properties. Further, immunoconjugates of anti-EGFR antibodies kill EGFR expressing cells unexpectedly well, as demonstrated using in vivo tumor models.

I. Definitions

To facilitate an understanding of the present invention, a number of terms and phrases are defined below.

As used herein, "epidermal growth factor receptor" or "EGFR" refers to the mature, tyrosine kinase cell surface receptor. The term "soluble EGFR" or "sEGFR" refers to a portion of EGFR containing the extracellular, ligand-binding domain of EGFR. More specifically, sEGFR contains amino acids 1-619 of mature EGFR (Ullrich et al., Human Epidermal Growth Factor cDNA Sequence and Aberrant Expression of the Amplified Gene in A-431 Epidermoid Carcinoma Cells, Nature, Vol. 309, 418-25 (1986)).

The phrase "EGFR mediated cancer" refers to a cancer characterized by epithelial tumors in which EGFR is abnormally activated to levels greater than in normal, corresponding epithelial tissue. These greater levels of EGFR activity promote tumor growth in many types of cancer. Such cancers include, but are not limited to, non-small cell lung cancer, breast cancer, colorectal cancer, head and neck cancers, and prostate cancer. Abnormal activation of EGFR can arise from overexpression of the receptor, gene amplification, activating mutations, overexpression of receptor ligands, and/or loss of regulators of EGFR activity.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

A "blocking" antibody or an "antagonist" antibody is one which inhibits or reduces biological activity of the antigen it binds, such as EGFR. In some embodiments, blocking antibodies or antagonist antibodies substantially or completely inhibit the biological activity of the antigen. The biological activity can be reduced by 10%, 20%, 30%, 50%, 70%, 80%, 90%, 95%, or even 100%.

The phrase "ability to inhibit EGFR activation" with respect to an antibody as used herein, is intended to refer to an antibody whose binding to EGFR results in inhibition of human EGFR activation and the biological activity of human EGFR that occurs upon activation of the receptor. Measuring one or more indicators of EGFR biological activity as determined using either a cell proliferation assay, an apoptosis assay, a receptor binding assay, a receptor phosphorylation assay, or a mouse tumor model (see Examples) can assess an antibody's ability to inhibit EGFR activation.

The term "anti-EGFR antibody" or "an antibody that binds to EGFR" refers to an antibody that is capable of binding EGFR with sufficient affinity such that the antibody is useful as a diagnostic and/or therapeutic agent in targeting EGFR. Several anti-EGFR antibodies are known in the art. For example, cetuximab (Ab 225) and 528 Ab are described in U.S. Pat. No. 4,943,533, which is herein incorporated by reference.

The extent of binding of an anti-EGFR antibody to an unrelated, non-EGFR protein can be less than about 10% of the binding of the antibody to EGFR as measured, e.g., by a radioimmunoassay (RIA). In certain embodiments, an antibody that binds to EGFR has a dissociation constant (Kd) of ≤1 μM, ≤100 nM, ≤:10 nM, ≤1 nM, or ≤0.1 nM.

The term "antibody fragment" refers to a portion of an intact antibody and refers to the antigenic determining variable regions of an intact antibody. Examples of antibody fragments include, but are not limited to Fab, Fab', F(ab')2, and Fv fragments, linear antibodies, single chain antibodies, and multispecific antibodies formed from antibody fragments.

A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of manners including but not limited to by hybridoma, phage selection, recombinant expression, and transgenic animals.

The term "humanized antibody" refers to forms of non-human (e.g. murine) antibodies that are specific immunoglobulin chains, chimeric immunoglobulins, or fragments thereof that contain minimal non-human (e.g., murine) sequences. Typically, humanized antibodies are human immunoglobulins in which residues from the complementary determining region (CDR) are replaced by residues from the CDR of a non-human species (e.g. mouse, rat, rabbit, hamster) that have the desired specificity, affinity, and capability (Jones et al., 1986, Nature, 321:522-525; Riechmann et al., 1988, Nature, 332:323-327; Verhoeyen et al., 1988, Science, 239:1534-1536). In some instances, the Fv framework region (FR) residues of a human immunoglobulin are replaced with the corresponding residues in an antibody from a non-human species that has the desired specificity, affinity, and capability. The humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. No. 5,225,539.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al (1997) J. Molec. Biol. 273:927-948)). In addition, combinations of these two approaches are sometimes used in the art to determine CDRs.

The Kabat numbering system is generally used when referring to a residue in the variable domain (approximately residues 1-107 of the light chain and residues 1-113 of the heavy chain) (e.g, Kabat et al., Sequences of Immunological Interest. 5th Ed. Public Health Service, National Institutes of Health, Bethesda, Md. (1991)).

The amino acid position numbering as in Kabat, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence can contain fewer or additional amino acids corresponding to a shortening of, or insertion into, a FR or CDR of the variable domain. For example, a heavy chain variable domain can include a single amino acid insert (residue 52a according to Kabat) after residue 52 of H2 and inserted residues (e.g. residues 82a, 82b, and 82c, etc according to Kabat) after heavy chain FR residue 82. The Kabat numbering of residues can be determined for a given antibody by alignment at regions of homology of the sequence of the antibody with a "standard" Kabat numbered sequence. Chothia refers instead to the location of the structural loops (Chothia and Lesk J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

| Loop | Kabat | AbM | Chothia |
|------|-------|-----|---------|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32..34 |
| | (Kabat Numbering) | | |
| H1 | H31-H35 | H26-H35 | H26-H32 |
| | (Chothia Numbering) | | |
| H2 | H50-H65 | H50-H58 | H52-H56 |
| H3 | H95-H102 | H95-H102 | H95-H102 |

The term "human antibody" means an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g. mouse, rat, rabbit, etc) with the desired specificity, affinity, and capability while the constant regions are homologous to the sequences in antibodies derived from another (usually human) to avoid eliciting an immune response in that species.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

"Or better" when used herein to refer to binding affinity refers to a stronger binding between a molecule and its binding partner. "Or better" when used herein refers to a stronger binding, represented by a smaller numerical Kd value. For example, an antibody which has an affinity for an antigen of "0.6 nM or better", the antibody's affinity for the antigen is <0.6 nM, i.e. 0.59 nM, 0.58 nM, 0.57 nM etc. or any value less than 0.6 nM.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

An antibody is said to "competitively inhibit" binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

The phrase "substantially similar," or "substantially the same", as used herein, denotes a sufficiently high degree of similarity between two numeric values (generally one associated with an antibody of the invention and the other associated with a reference/comparator antibody) such that one of skill in the art would consider the difference between the two values to be of little or no biological and/or statistical significance within the context of the biological characteristic measured by said values (e.g., Kd values). The difference between said two values can be less than about 50%, less than about 40%, less than about 30%, less than about 20%, or less than about 10% as a function of the value for the reference/comparator antibody. The difference between two "substantially similar binding affinities" is generally less than about 10% as a function of the value for the reference/comparator antibody.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cell or compositions include those which have been purified to a degree that they are no longer in a form in which they are found in nature. In some embodiments, an antibody, polynucleotide, vector, cell, or composition which is isolated is substantially pure.

As used herein, "substantially pure" refers to material which is at least 50% pure (i.e., free from contaminants), at least 90% pure, at least 95% pure, at least 98% pure, or at least 99% pure.

The term "immunoconjugate" or "conjugate" as used herein refers to a compound or a derivative thereof that is linked to a cell binding agent (i.e., an anti-EGFR antibody or fragment thereof) and is defined by a generic formula: C-L-A, wherein C=cytotoxin, L=linker, and A=cell binding agent or anti-EGFR antibody or antibody fragment. Immunoconjugates can also be defined by the generic formula in reverse order: A-L-C.

A "linker" is any chemical moiety that is capable of linking a compound, usually a drug, such as a maytansinoid, to a cell-binding agent such as an anti EGFR antibody or a fragment thereof in a stable, covalent manner. Linkers can be susceptible to or be substantially resistant to acid-induced cleavage, light-induced cleavage, peptidase-induced cleavage, esterase-induced cleavage, and disulfide bond cleavage, at conditions under which the compound or the antibody remains active. Suitable linkers are well known in the art and include, for example, disulfide groups, thioether groups, acid labile groups, photolabile groups, peptidase labile groups and esterase labile groups. Linkers also include charged linkers, and hydrophilic forms thereof as described herein and know in the art.

The terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. "Tumor" and "neoplasm" refer to one or more cells that result from excessive cell growth or proliferation, either benign (noncancerous) or malignant (cancerous) including pre-cancerous lesions. Examples of "cancer" or "tumorigenic" diseases which can be treated and/or prevented include neoplasms of the abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system.

The terms "cancer cell," "tumor cell," and grammatical equivalents refer to the total population of cells derived from a tumor or a pre-cancerous lesion, including both non-tumorigenic cells, which comprise the bulk of the tumor cell population, and tumorigenic stem cells (cancer stem cells). As used herein, the term "tumor cell" will be modified by the term "non-tumorigenic" when referring solely to those tumor cells lacking the capacity to renew and differentiate to distinguish those tumor cells from cancer stem cells.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

Administration "in combination with" one or more further therapeutic agents includes simultaneous (concurrent) and consecutive administration in any order.

The term "pharmaceutical formulation" refers to a preparation which is in such form as to permit the biological activity of the active ingredient to be effective, and which contains no additional components which are unacceptably toxic to a subject to which the formulation would be administered. The formulation can be sterile.

An "effective amount" of an antibody as disclosed herein is an amount sufficient to carry out a specifically stated purpose. An "effective amount" can be determined empirically and in a routine manner, in relation to the stated purpose.

The term "therapeutically effective amount" refers to an amount of an antibody or other drug effective to "treat" a disease or disorder in a subject or mammal. In the case of cancer, the therapeutically effective amount of the drug can reduce the number of cancer cells; reduce the tumor size; inhibit (i.e., slow to some extent or stop) cancer cell infiltration into peripheral organs; inhibit (i.e., slow to some extent or stop) tumor metastasis; inhibit, to some extent, tumor growth; and/or relieve to some extent one or more of the symptoms associated with the cancer. See the definition herein of "treating". To the extent the drug can prevent growth and/or kill existing cancer cells, it can be cytostatic and/or cytotoxic. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The word "label" when used herein refers to a detectable compound or composition which is conjugated directly or indirectly to the antibody so as to generate a "labeled" antibody. The label can be detectable by itself (e.g. radioisotope labels or fluorescent labels) or, in the case of an enzymatic label, can catalyze chemical alteration of a substrate compound or composition which is detectable.

A "chemotherapeutic agent" is a chemical compound useful in the treatment of cancer, regardless of mechanism of action. Chemotherapeutic agents include, for example, antagonists of CD20 such as Rituximab and cyclophosphamide, doxorubicin, vincristine, predinisone, fludarabine, etoposide, methotrexate, lenalidomide, chlorambucil, bentamustine and/or modified versions of such chemotherapeutics.

Terms such as "treating" or "treatment" or "to treat" or "alleviating" or "to alleviate" refer to both 1) therapeutic measures that cure, slow down, lessen symptoms of, and/or halt progression of a diagnosed pathologic condition or disorder and 2) prophylactic or preventative measures that prevent and/or slow the development of a targeted pathologic condition or disorder. Thus, those in need of treatment include those already with the disorder; those prone to have the disorder; and those in whom the disorder is to be prevented. In certain embodiments, a subject is successfully "treated" for cancer according to the methods of the present invention if the patient shows one or more of the following: a reduction in the number of or complete absence of cancer cells; a reduction in the tumor size; inhibition of or an absence of cancer cell infiltration into peripheral organs including, for example, the spread of cancer into soft tissue and bone; inhibition of or an absence of tumor metastasis; inhibition or an absence of tumor growth; relief of one or more symptoms associated with the specific cancer; reduced morbidity and mortality; improvement in quality of life; reduction in tumorigenicity, tumorgenic frequency, or tumorgenic capacity, of a tumor; reduction in the number or frequency of cancer stem cells in a tumor; differentiation of tumorigenic cells to a non-tumorigenic state; or some combination of effects.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide can comprise modified nucleotides, such as methylated nucleotides and their analogs. If present, modification to the nucleotide structure can be imparted before or after assembly of the polymer. The sequence of nucleotides can be interrupted by non-nucleotide components. A polynucleotide can be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars can be replaced, for example, by phosphonate groups, phosphate groups, protected by standard protecting groups, or activated to prepare additional linkages to additional nucleotides, or can be conjugated to solid supports. The 5' and 3' terminal OH can be phosphorylated or substituted with amines or organic capping group moieties of from 1 to 20 carbon atoms. Other hydroxyls can also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, .alpha.-anomeric sugars, epimeric sugars such as arabinose, xyloses or lyxoses, pyranose sugars, furanose sugars, sedoheptuloses, acyclic analogs and a basic nucleoside analogs such as methyl riboside. One or more phosphodiester linkages can be replaced by alternative linking groups. These alternative linking groups include, but are not limited to, embodiments wherein phosphate is replaced by P(O)S ("thioate"), P(S)S ("dithioate"), "(O)NR$_2$ ("amidate"), P(O)R, P(O)OR, CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

The term "vector" means a construct, which is capable of delivering, and optionally expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon antibodies, in certain embodiments, the polypeptides can occur as single chains or associated chains.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. One such non-limiting example of a sequence alignment algorithm is the algorithm described in Karlin et al, 1990, *Proc. Natl. Acad. Sci.*, 87:2264-2268, as modified in Karlin et al., 1993, *Proc. Natl. Acad. Sci.*, 90:5873-5877, and incorporated into the NBLAST and XBLAST programs (Altschul et al., 1991, *Nucleic Acids Res.*, 25:3389-3402). In certain embodiments, Gapped BLAST can be used as described in Altschul et al., 1997, *Nucleic Acids Res.* 25:3389-3402. BLAST-2, WU-BLAST-2 (Altschul et al., 1996, *Methods in Enzymology*, 266:460-480), ALIGN, ALIGN-2 (Genentech, South San Francisco, Calif.) or Megalign (DNASTAR) are additional publicly available software programs that can be used to align sequences. In certain embodiments, the percent identity between two nucleotide sequences is determined using the GAP program in GCG software (e.g., using a NWSgapdna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (*J. Mol. Biol.* (48): 444-453 (1970)) can be used to determine the percent identity between two amino acid sequences (e.g., using either a Blossum 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (CABIOS, 4:11-17 (1989)). For example, the percent identity can be determined using the ALIGN program (version 2.0) and using a PAM120 with residue table, a gap length penalty of 12 and a gap penalty of 4. Appropriate parameters for maximal alignment by particular alignment software can be determined by one skilled in the art. In certain embodiments, the default parameters of the alignment software are used. In certain embodiments, the percentage identity "X" of a first amino acid sequence to a second sequence amino acid is calculated as 100× (Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be longer than the percent identity of the second sequence to the first sequence.

As a non-limiting example, whether any particular polynucleotide has a certain percentage sequence identity (e.g., is at least 80% identical, at least 85% identical, at least 90% identical, and in some embodiments, at least 95%, 96%, 97%, 98%, or 99% identical) to a reference sequence can, in certain embodiments, be determined using the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2: 482 489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

In some embodiments, two nucleic acids or polypeptides of the invention are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. Identity can exist over a region of the sequences that is at least about 10, about 20, about 40-60 residues in length or any integral value therebetween, and can be over a longer region than 60-80 residues, for example, at least about 90-100 residues, and in some embodiments, the sequences are substantially identical over the full length of the sequences being compared, such as the coding region of a nucleotide sequence for example.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In some embodiments, conservative substitutions in the sequences of the polypeptides and antibodies of the invention do not abrogate the binding of the polypeptide or antibody containing the amino acid sequence, to the antigen(s), i.e., the EGFR to which the polypeptide or antibody binds. Methods of identifying nucleotide and amino acid conservative substitutions which do not eliminate antigen binding are well-known in the art (see, e.g., Brummell et al., *Biochem.* 32: 1180-1 187 (1993); Kobayashi et al. *Protein Eng.* 12(10):879-884 (1999); and Burks et al. *Proc. Natl. Acad. Sci. USA* 94:.412-417 (1997)).

As used in the present disclosure and claims, the singular forms "a," "an," and "the" include plural forms unless the context clearly dictates otherwise.

It is understood that wherever embodiments are described herein with the language "comprising," otherwise analogous embodiments described in terms of "consisting of" and/or "consisting essentially of" are also provided.

The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. EGFR Binding Agents

Tumors often overexpress growth factor receptors that bind various ligands ligand and facilitate unrestricted tumor growth. One example of such growth factor receptors are the receptors of the Epidermal Growth Factor Receptor (EGFR) protein family.

Signal transduction through members of the Epidermal Growth Factor Receptor (EGFR) protein family is dependent upon the formation of homodimers or heterodimers triggered by the binding of ligand. This receptor family is comprised of four membrane-bound proteins: EGFR, HER2/neu, HER3 and HER4. Overexpression of these proteins has been correlated with a poor prognosis in a number of types of cancer, including, but not limited to, breast, colon, ovarian, endometrial, gastric, pancreatic, prostate and salivary gland cancers. While a number of groups have developed strategies to target individual members of the EGFR protein family (e.g., HER2/neu or EGFR) to inhibit tumor growth, none of the treatments has been proven to ultimately cure these forms of cancer.

In accordance with this invention novel agents (e.g. antibodies) are provided that specifically bind to EGFR. These novel agents are non-antagonistic of EGFR. However, when attached to an effector (e.g., as an immunoconjugate) the effector rescues the killing activity such that the immunoconjugate can act to inhibit growth and/or proliferation of the target cells.

Thus, present invention provides agents that specifically bind EGFR. These agents are referred to herein as "EGFR binding agents." The EGFR binding agents described differ from EGFR binding agents of the prior art in that they are non-antagonistic antibodies, and can be weakly agonistic.

In certain embodiments, the EGFR binding agents are antibodies, immunoconjugates or polypeptides. In some embodiments, the EGFR binding agents are humanized antibodies.

In certain embodiments, the EGFR-binding agents have one or more of the following effects: inhibit proliferation of tumor cells, reduce the tumorigenicity of a tumor by reducing the frequency of cancer stem cells in the tumor, inhibit tumor growth, increase survival, trigger cell death of tumor cells, differentiate tumorigenic cells to a non-tumorigenic state, or prevent metastasis of tumor cells.

In some embodiments, the EGFR-binding agents are capable of reducing tumor volume. The ability of a EGFR-binding agent to reduce tumor volume can be assessed, for example, by measuring a % T/C value, which is the median tumor volume of treated subjects divided by the median tumor volume of the control subjects. In some embodiments, treatment with a EGFR-binding agent results in a % T/C value that is less than about 55%, less than about 50%, less than about 45%, less than about 40%, less than about 35%, less than about 30%, less than about 25%, less than about 20%, less than about 15%, less than about 10%, or less than about 5%.

In certain embodiments, immunoconjugates or other agents that specifically bind human EGFR trigger cell death via a cytotoxic agent. For example, in certain embodiments, an antibody to a human EGFR antibody is conjugated to a maytansinoid that is activated in tumor cells expressing the EGFR by protein internalization. In certain alternative embodiments, the agent or antibody is not conjugated.

In certain embodiments, the EGFR-binding agents are capable of inhibiting tumor growth. In certain embodiments, the EGFR-binding agents are capable of inhibiting tumor growth in vivo (e.g., in a xenograft mouse model and/or in a human having cancer).

The EGFR-binding agents include EGFR antibodies ML66 and EGFR-8 and fragments, variants and derivatives thereof. The EGFR-binding agents also include EGFR-binding agents that specifically bind to the same EGFR epitope as the antibodies ML66 and EGFR-8. The EGFR-binding agents also include EGFR-binding agents that competitively inhibit the antibodies ML66 and EGFR-8. A plasmid encoding the heavy and light chain sequences of ML66 was deposited with American Type Culture Collection (ATCC) on Oct. 21, 2010 and given deposit number PTA-11424. A hybridoma encoding EGFR-8 was deposited with ATCC on Oct. 21, 2010 and given deposit number PTA-11423.

The EGFR-binding agents also include EGFR-binding agents that comprise the heavy and light chain CDR sequences of ML66 and EGFR-8. The CDR sequences of ML66 and EGFR-8, both murine and humanized are described in Tables 1 and 2 below.

TABLE 1

| Variable heavy chain CDR amino acid sequences | | | |
|---|---|---|---|
| Antibody | VH-CDR1 | VH-CDR2 | VH-CDR3 |
| ML66 | ASNSVS (SEQ ID NO: 1) | VIWNHGGTD (SEQ ID NO: 2) | KGGIYFDY (SEQ ID NO: 3) |
| ML66 Kabat HC CDR2 (rat) | | VIWNHGGTDYNSVIKS (SEQ ID NO: 4) | |
| ML66 Kabat HC CDR2 (humanized) | | VIWNHGGTDYNPSIKS (SEQ ID NO: 5) | |

TABLE 1-continued

Variable heavy chain CDR amino acid sequences

| Antibody | VH-CDR1 | VH-CDR2 | VH-CDR3 |
|---|---|---|---|
| EGFR-8 | KDTYIH (SEQ ID NO: 6) | RIDPTNGNNK (SEQ ID NO: 7) | EDGYRYDDW YFDV (SEQ ID NO: 8) |
| EGFR-8 Kabat HC CDR2 (murine) | | RIDPTNGNNKYDPK FQG (SEQ ID NO: 9) | |
| EGFR-8 Kabat HC CDR2 (humanized) | | RIDPTNGNNKYDQK FQG (SEQ ID NO: 10) | |

TABLE 2

Variable light chain CDR amino acid sequences

| Antibody | VL-CDR1 | VL-CDR2 | VL-CDR3 |
|---|---|---|---|
| ML66 | RASESVSTLMH (SEQ ID NO: 11) | LASHRES (SEQ ID NO: 12) | QQSRNDPWT (SEQ ID NO: 13) |
| EGFR-8 | SASSSVSYMH (SEQ ID NO: 14) | ATSKLAS (SEQ ID NO: 15) | QQWSSNPLT (SEQ ID NO: 16) |

The EGFR binding molecules can be antibodies or antigen binding fragments that specifically bind to EGFR that comprise the CDRs of ML66 or EGFR-8 with up to four (i.e. 0, 1, 2, 3, or 4) conservative amino acid substitutions per CDR.

Polypeptides can comprise one of the individual variable light chains or variable heavy chains described herein. Antibodies and polypeptides can also comprise both a variable light chain and a variable heavy chain. The variable light chain and variable heavy chain sequences of murine and humanized ML66 and EGFR-8 antibodies are provided in Tables 3 and 4 below.

TABLE 3

Variable heavy chain amino acid sequences

| Antibody | VH Amino Acid Sequence |
|---|---|
| ratML66 $V_H$ | QVQLKESGPGLVQPSQTLSLTCTVSGLSLASNSVSWIRQ PPGKGLEWMGVIWNHGGTDYNSVIKSRLSISRDTSKSQV FLKMNSLQTEDTAMYFCVRKGGIYFDYWGQGVMVTVSS (SEQ ID NO: 17) |
| huML66 $V_H$ | QVQLQESGPGLVKPSETLSLTCTVSGLSLASNSVSWIRQ PPGKGLEWMGVIWNHGGTDYNPSIKSRLSISRDTSKSQV FLKMNSLTAADTAMYFCVRKGGIYFDYWGQGVLVTVSS (SEQ ID NO: 18) |
| muEGFR-8 $V_H$ | EVQLQQSGAELVKPGASVKLSCTTSGFNIKDTYIHWVKK RPEQGLEWIGRIDPTNGNNKYDPKFQGKATITADTSSNT AYLQLSSLTSEDTAVYYCTREDGYRYDDWYFDVWGAGTT VTVSS (SEQ ID NO: 19) |
| huEGFR-8 $V_H$ | QVQLVQSGAEVVKPGASVKLSCTTSGFTIKDTYIHWVKK RPGQGLEWIGRIDPTNGNNKYDQKFQGKATITADTSSNT AYLQLSSLTSEDTAVYYCTREDGYRYDDWYFDVWGQGTL VTVSS (SEQ ID NO: 20) |

TABLE 4

Variable light chain amino acid sequences

| Antibody | VL Amino Acid Sequence |
|---|---|
| ratML66 $V_L$ | DTVLTQSPALAVSPGERVTISCRASESVSTLMHWYQQKS GQQPKLLIYLASHRESGVPARFSGSGSGTDFTLTIDPME ADDTATYYCQQSRNDPWTFGGGTNLELKR (SEQ ID NO: 21) |
| huML66 $V_L$ | DTVLTQSPSLAVSPGERATISCRASESVSTLMHWYQQKP GQQTKLLIYLASHRESGVPARFSGSGSGTDFTLTIDPME AEDTATYYCQQSRNDPWTFGQGTKLELKR (SEQ ID NO: 22) |
| muEGFR-8 $V_L$ | QIVLTQSPASMSASPGEKVTMTCSASSSVSYMHWYQQKS GTSPKRWIYATSKLASGVPARFSGSGSGTSYSLTISSME AEDAATYYCQQWSSNPLTFGAGTKLELKR (SEQ ID NO: 23) |
| huEGFR-8 $V_L$ | DIVLTQSPAFMSASPGEKVTMTCSASSSVSYMHWYQQKP DQSPKRWIYATSKLASGVPSRFSGSGSGTDYSLTISSME AEDAATYYCQQWSSNPLTFGQGTKLELKR (SEQ ID NO: 24) |

Also provided are polypeptides that comprise: (a) a polypeptide having at least about 90% sequence identity to SEQ ID NOs:17-20; and/or (b) a polypeptide having at least about 90% sequence identity to SEQ ID NOs:21-24. In certain embodiments, the polypeptide comprises a polypeptide having at least about 95%, at least about 96%, at least about 97%, at least about 98%, or at least about 99% sequence identity to SEQ ID NOs: 17-24. Thus, in certain embodiments, the polypeptide comprises (a) a polypeptide having at least about 95% sequence identity to SEQ ID NOs: 17-20, and/or (b) a polypeptide having at least about 95% sequence identity to SEQ ID NOs:21-24. In certain embodiments, the polypeptide comprises (a) a polypeptide having the amino acid sequence of SEQ ID NOs:17-20; and/or (b) a polypeptide having the amino acid sequence of SEQ ID NOs:21-24. In certain embodiments, the polypeptide is an antibody and/or the polypeptide specifically binds EGFR. In certain embodiments, the polypeptide is a murine, chimeric, or humanized antibody that specifically binds EGFR. In certain embodiments, the polypeptide having a certain percentage of sequence identity to SEQ ID NOs: 17-24 differs from SEQ ID NOs: 17-24 by conservative amino acid substitutions only.

TABLE 5

Full-length heavy chain and light chain amino acid sequences

| Antibody | Full-Length Heavy/Light Chain Amino Acid Sequence |
|---|---|
| huML66HC | QVQLQESGPGLVKPSETLSLTCTVSGLSLASNSVSWIRQ PPGKGLEWMGVIWNHGGTDYNPSIKSRLSISRDTSKSQV FLKMNSLTAADTAMYFCVRKGGIYFDYWGQGVLVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKKVEPKSCDKTHTCPPCPAPELL GGPSVFLFPPKPKDTLMISRTPEVTCVVVDVSHEDPEVK FNWYVDGVEVHNAKTKPREEQYNSTYRVVSVLTVLHQDW LNGKEYKCKVSNKALPAPIEKTISKAKGQPREPQVYTLP PSRDELTKNQVSLTCLVKGFYPSDIAVEWESNGQPENNY KTTPPVLDSDGSFFLYSKLTVDKSRWQQGNVFSCSVMHE ALHNHYTQKSLSLSPG (SEQ ID NO: 25) |
| huML66LC | DTVLTQSPSLAVSPGERATISCRASESVSTLMHWYQQKP GQQPKLLIYLASHRESGVPARFSGSGSGTDFTLTIDPME AEDTATYYCQQSRNDPWTFGQGTKLELKRTVAAPSVFIF PPSDEQLKSGTASVVCLLNNFYPREAKVQWKVDNALQSG NSQESVTEQDSKDSTYSLSSTLTLSKADYEKHKVYACEV THQGLSSPVTKSFNRGEC (SEQ ID NO: 26) |

TABLE 5-continued

Full-length heavy chain and light chain amino acid sequences

| Antibody | Full-Length Heavy/Light Chain Amino Acid Sequence |
|---|---|
| huEGFR-8 HC | QVQLVQSGAEVVKPGASVKLSCTTSGFTIKDTYIHWVKK RPGQGLEWIGRIDPTNGNNKYDQKFQGKATITADTSSNT AYLQLSSLTSEDTAVYYCTREDGYRYDDWYFDVWGQGTL VTVSSASTKGPSVFPLAPSSKSTSGGTAALGCLVKDYFP EPVTVSWNSGALTSGVHTFPAVLQSSGLYSLSSVVTVPS SSLGTQTYICNVNHKPSNTKVDKKVEPKSCDKTHTCPPC PAPELLGGPSVFLFPPKPKDTLMISRTPEVTCVVVDVSH EDPEVKFNWYVDGVEVHNAKTKPREEQYNSTYRVVSVLT VLHQDWLNGKEYKCKVSNKALPAPIEKTISKAKGQPREP QVYTLPPSRDELTKNQVSLTCLVKGFYPSDIAVEWESNG QPENNYKTTPPVLDSDGSFFLYSKLTVDKSRWQQGNVFS CSVMHEALHNHYTQKSLSLSPG (SEQ ID NO: 27) |
| huEGFR-8 LC | DIVLTQSPAFMSASPGEKVTMTCSASSSVSYMHWYQQKP DQSPKRWIYATSKLASGVPSRFSGSGSGTDYSLTISSME AEDAATYYCQQWSSNPLTFGQGTKLELKRTVAAPSVFIF PPSDEQLKSGTASVVCLLNNFYPREAKVQWKVDNALQSG NSQESVTEQDSKDSTYSLSSTLTLSKADYEKHKVYACEV THQGLSSPVTKSFNRGEC (SEQ ID NO: 28) |

Also provided are polypeptides that comprise: (a) a polypeptide having at least about 90% sequence identity to SEQ ID NOs:25 and 27; and/or (b) a polypeptide having at least about 90% sequence identity to SEQ ID NOs:26 and 28. In certain embodiments, the polypeptide comprises a polypeptide having at least about 95%, at least about 96%, at least about 97%, at least about 98%, or at least about 99% sequence identity to SEQ ID NOs:25-28. Thus, in certain embodiments, the polypeptide comprises (a) a polypeptide having at least about 95% sequence identity to SEQ ID NOs: 25 and 27, and/or (b) a polypeptide having at least about 95% sequence identity to SEQ ID NOs:26 and 28. In certain embodiments, the polypeptide comprises (a) a polypeptide having the amino acid sequence of SEQ ID NOs:25 and 27; and/or (b) a polypeptide having the amino acid sequence of SEQ ID NOs:26 and 28. In certain embodiments, the polypeptide is an antibody and/or the polypeptide specifically binds EGFR. In certain embodiments, the polypeptide is a humanized antibody that specifically binds EGFR. In certain embodiments, the polypeptide having a certain percentage of sequence identity to SEQ ID NOs:25-28 differs from SEQ ID NOs:25-28 by conservative amino acid substitutions only.

Monoclonal antibodies can be prepared using hybridoma methods, such as those described by Kohler and Milstein (1975) Nature 256:495. Using the hybridoma method, a mouse, hamster, or other appropriate host animal, is immunized as described above to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g. radioimmunoassay (RIA); enzyme-linked immunosorbent assay (ELISA)) can then be propagated either in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

Alternatively monoclonal antibodies can also be made using recombinant DNA methods as described in U.S. Pat. No. 4,816,567. The polynucleotides encoding a monoclonal antibody are isolated from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries expressing CDRs of the desired species as described (McCafferty et al., 1990, Nature, 348:552-554; Clackson et al., 1991, Nature, 352:624-628; and Marks et al., 1991, J. Mol. Biol., 222:581-597).

The polynucleotide(s) encoding a monoclonal antibody can further be modified in a number of different manners using recombinant DNA technology to generate alternative antibodies. In some embodiments, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

In some embodiments, the monoclonal antibody against the human EGFR is a humanized antibody. In certain embodiments, such antibodies are used therapeutically to reduce antigenicity and HAMA (human anti-mouse antibody) responses when administered to a human subject. Humanized antibodies can be produced using various techniques known in the art. In certain alternative embodiments, the antibody to EGFR is a human antibody.

Human antibodies can be directly prepared using various techniques known in the art. Immortalized human B lymphocytes immunized in vitro or isolated from an immunized individual that produce an antibody directed against a target antigen can be generated (See, e.g., Cole et al., Monoclonal Antibodies and Cancer Therapy, Alan R. Liss, p. 77 (1985); Boerner et al., 1991, J. Immunol., 147 (1):86-95; and U.S. Pat. No. 5,750,373). Also, the human antibody can be selected from a phage library, where that phage library expresses human antibodies, as described, for example, in Vaughan et al., 1996, Nat. Biotech., 14:309-314, Sheets et al., 1998, Proc. Nat'l. Acad. Sci., 95:6157-6162, Hoogenboom and Winter, 1991, J. Mol. Biol., 227:381, and Marks et al., 1991, J. Mol. Biol., 222:581). Techniques for the generation and use of antibody phage libraries are also described in U.S. Pat. Nos. 5,969,108, 6,172,197, 5,885,793, 6,521,404; 6,544,731; 6,555,313; 6,582,915; 6,593,081; 6,300,064; 6,653,068; 6,706,484; and 7,264,963; and Rothe et al., 2007, J. Mol. Bio., doi:10.1016/j.jmb.2007.12.018 (each of which is incorporated by reference in its entirety). Affinity maturation strategies and chain shuffling strategies (Marks et al., 1992, Bio/Technology 10:779-783, incorporated by reference in its entirety) are known in the art and can be employed to generate high affinity human antibodies.

Humanized antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

This invention also encompasses bispecific antibodies that specifically recognize a EGFR. Bispecific antibodies are antibodies that are capable of specifically recognizing and binding at least two different epitopes. The different epitopes can either be within the same molecule (e.g. the same EGFR) or on different molecules such that both, for example, the antibodies can specifically recognize and bind a EGFR as well as, for example, 1) an effector molecule on a leukocyte such as a T-cell receptor (e.g. CD3) or Fc receptor (e.g. CD64, CD32, or CD16) or 2) a cytotoxic agent as described in detail below.

Exemplary bispecific antibodies can bind to two different epitopes, at least one of which originates in a polypeptide of the invention. Alternatively, an anti-antigenic arm of an immunoglobulin molecule can be combined with an arm which binds to a triggering molecule on a leukocyte such as a T cell receptor molecule (e.g. CD2, CD3, CD28, or B7), or Fc receptors for IgG so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Techniques for making bispecific antibodies are common in the art (Millstein et al., 1983, Nature 305:537-539; Brennan et al., 1985, Science 229:81; Suresh et al, 1986, Methods in Enzymol. 121:120; Traunecker et al., 1991, EMBO J. 10:3655-3659; Shalaby et al., 1992, J. Exp. Med. 175:217-225; Kostelny et al., 1992, J. Immunol. 148:1547-1553; Gruber et al., 1994, J. Immunol. 152:5368; and U.S. Pat. No. 5,731,168). Antibodies with more than two valencies are also contemplated. For example, trispecific antibodies can be prepared (Tutt et al., J. Immunol. 147:60 (1991)). Thus, in certain embodiments the antibodies to EGFR are multispecific.

In certain embodiments are provided an antibody fragment to, for example, increase tumor penetration. Various techniques are known for the production of antibody fragments. Traditionally, these fragments are derived via proteolytic digestion of intact antibodies (for example Morimoto et al., 1993, Journal of Biochemical and Biophysical Methods 24:107-117; Brennan et al., 1985, Science, 229:81). In certain embodiments, antibody fragments are produced recombinantly. Fab, Fv, and scFv antibody fragments can all be expressed in and secreted from *E. coli* or other host cells, thus allowing the production of large amounts of these fragments. Such antibody fragments can also be isolated from the antibody phage libraries discussed above. The antibody fragment can also be linear antibodies as described in U.S. Pat. No. 5,641,870, for example, and can be monospecific or bispecific. Other techniques for the production of antibody fragments will be apparent to the skilled practitioner.

According to the present invention, techniques can be adapted for the production of single-chain antibodies specific to EGFR (see U.S. Pat. No. 4,946,778). In addition, methods can be adapted for the construction of Fab expression libraries (Huse, et al., Science 246:1275-1281 (1989)) to allow rapid and effective identification of monoclonal Fab fragments with the desired specificity for EGFR, or derivatives, fragments, analogs or homologs thereof. Antibody fragments can be produced by techniques in the art including, but not limited to: (a) a F(ab')2 fragment produced by pepsin digestion of an antibody molecule; (b) a Fab fragment generated by reducing the disulfide bridges of an F(ab')2 fragment, (c) a Fab fragment generated by the treatment of the antibody molecule with papain and a reducing agent, and (d) Fv fragments.

It can further be desirable, especially in the case of antibody fragments, to modify an antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

Heteroconjugate antibodies are also within the scope of the present invention. Heteroconjugate antibodies are composed of two covalently joined antibodies. Such antibodies have, for example, been proposed to target immune cells to unwanted cells (U.S. Pat. No. 4,676,980). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

For the purposes of the present invention, it should be appreciated that modified antibodies can comprise any type of variable region that provides for the association of the antibody with the polypeptides of a human EGFR. In this regard, the variable region can comprise or be derived from any type of mammal that can be induced to mount a humoral response and generate immunoglobulins against the desired tumor associated antigen. As such, the variable region of the modified antibodies can be, for example, of human, murine, non-human primate (e.g. cynomolgus monkeys, macaques, etc.) or lupine origin. In some embodiments both the variable and constant regions of the modified immunoglobulins are human. In other embodiments the variable regions of compatible antibodies (usually derived from a non-human source) can be engineered or specifically tailored to improve the binding properties or reduce the immunogenicity of the molecule. In this respect, variable regions useful in the present invention can be humanized or otherwise altered through the inclusion of imported amino acid sequences.

In certain embodiments, the variable domains in both the heavy and light chains are altered by at least partial replacement of one or more CDRs and, if necessary, by partial framework region replacement and sequence changing. Although the CDRs can be derived from an antibody of the same class or even subclass as the antibody from which the framework regions are derived, it is envisaged that the CDRs will be derived from an antibody of different class and possibly from an antibody from a different species. It is not always necessary to replace all of the CDRs with the complete CDRs from the donor variable region to transfer the antigen binding capacity of one variable domain to another. Rather, in some cases it is only necessary to transfer those residues that are necessary to maintain the activity of the antigen binding site. Given the explanations set forth in U.S. Pat. Nos. 5,585,089, 5,693,761 and 5,693,762, it will be well within the competence of those skilled in the art, either by carrying out routine experimentation or by trial and error testing to obtain a functional antibody with reduced immunogenicity.

Alterations to the variable region notwithstanding, those skilled in the art will appreciate that the modified antibodies of this invention will comprise antibodies (e.g., full-length antibodies or immunoreactive fragments thereof) in which at least a fraction of one or more of the constant region domains has been deleted or otherwise altered so as to provide desired biochemical characteristics such as increased tumor localization or reduced serum half-life when compared with an antibody of approximately the same immunogenicity comprising a native or unaltered constant region. In some embodiments, the constant region of the modified antibodies will comprise a human constant region. Modifications to the constant region compatible with this invention comprise additions, deletions or substitutions of one or more amino acids in one or more domains. That is, the modified antibodies disclosed herein can comprise alterations or modifications to one or more of the three heavy chain constant domains (CH1, CH2 or CH3) and/or to the light chain constant domain (CL). In some embodiments, modified constant regions wherein one or more domains are partially or entirely deleted are contemplated. In some embodiments, the modified antibodies will comprise domain deleted constructs or variants wherein the entire CH2 domain has been removed (ACH2 constructs). In some embodiments, the omitted constant region domain will be replaced by a short amino acid spacer (e.g. 10 residues) that provides some of the molecular flexibility typically imparted by the absent constant region.

Besides their configuration, it is known in the art that the constant region mediates several effector functions. For example, binding of the C1 component of complement to antibodies activates the complement system. Activation of complement is important in the opsonisation and lysis of cell pathogens. The activation of complement also stimulates the inflammatory response and can also be involved in autoimmune hypersensitivity. Further, antibodies bind to cells via the Fc region, with a Fc receptor site on the antibody Fc region binding to a Fc receptor (FcR) on a cell. There are a number of Fc receptors which are specific for different classes of antibody, including IgG (gamma receptors), IgE (eta receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

In certain embodiments, the EGFR-binding antibodies provide for altered effector functions that, in turn, affect the biological profile of the administered antibody. For example, the deletion or inactivation (through point mutations or other means) of a constant region domain can reduce Fc receptor binding of the circulating modified antibody thereby increasing tumor localization. In other cases, it can be that constant region modifications, consistent with this invention, moderate complement binding and thus reduce the serum half life and nonspecific association of a conjugated cytotoxin. Yet other modifications of the constant region can be used to eliminate disulfide linkages or oligosaccharide moieties that allow for enhanced localization due to increased antigen specificity or antibody flexibility. Similarly, modifications to the constant region in accordance with this invention can easily be made using well known biochemical or molecular engineering techniques well within the purview of the skilled artisan.

In certain embodiments, an EGFR-binding agent that is an antibody does not have one or more effector functions. For instance, in some embodiments, the antibody has no antibody-dependent cellular cytotoxicity (ADCC) activity and/or no complement-dependent cytotoxicity (CDC) activity. In certain embodiments, the antibody does not bind to an Fc receptor and/or complement factors. In certain embodiments, the antibody has no effector function.

It will be noted that in certain embodiments, the modified antibodies can be engineered to fuse the CH3 domain directly to the hinge region of the respective modified antibodies. In other constructs it can be desirable to provide a peptide spacer between the hinge region and the modified CH2 and/or CH3 domains. For example, compatible constructs could be expressed wherein the CH2 domain has been deleted and the remaining CH3 domain (modified or unmodified) is joined to the hinge region with a 5-20 amino acid spacer. Such a spacer can be added, for instance, to ensure that the regulatory elements of the constant domain remain free and accessible or that the hinge region remains flexible. However, it should be noted that amino acid spacers can, in some cases, prove to be immunogenic and elicit an unwanted immune response against the construct. Accordingly, in certain embodiments, any spacer added to the construct will be relatively non-immunogenic, or even omitted altogether, so as to maintain the desired biochemical qualities of the modified antibodies.

Besides the deletion of whole constant region domains, it will be appreciated that the antibodies of the present invention can be provided by the partial deletion or substitution of a few or even a single amino acid. For example, the mutation of a single amino acid in selected areas of the CH2 domain can be enough to substantially reduce Fc binding and thereby increase tumor localization. Similarly, it can be desirable to simply delete that part of one or more constant region domains that control the effector function (e.g. complement CLQ binding) to be modulated. Such partial deletions of the constant regions can improve selected characteristics of the antibody (serum half-life) while leaving other desirable functions associated with the subject constant region domain intact. Moreover, as alluded to above, the constant regions of the disclosed antibodies can be modified through the mutation or substitution of one or more amino acids that enhances the profile of the resulting construct. In this respect it can be possible to disrupt the activity provided by a conserved binding site (e.g. Fc binding) while substantially maintaining the configuration and immunogenic profile of the modified antibody. Certain embodiments can comprise the addition of one or more amino acids to the constant region to enhance desirable characteristics such as decreasing or increasing effector function or provide for more cytotoxin or carbohydrate attachment. In such embodiments it can be desirable to insert or replicate specific sequences derived from selected constant region domains.

The present invention further embraces variants and equivalents which are substantially homologous to the chimeric, humanized and human antibodies, or antibody fragments thereof, set forth herein. These can contain, for example, conservative substitution mutations, i.e. the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

The polypeptides of the present invention can be recombinant polypeptides, natural polypeptides, or synthetic polypeptides comprising an antibody, or fragment thereof, against a human EGFR. It will be recognized in the art that some amino acid sequences of the invention can be varied without significant effect of the structure or function of the protein. Thus, the invention further includes variations of the polypeptides which show substantial activity or which include regions of an antibody, or fragment thereof, against EGFR protein. Such mutants include deletions, insertions, inversions, repeats, and type substitutions.

The polypeptides and analogs can be further modified to contain additional chemical moieties not normally part of the protein. Those derivatized moieties can improve the solubility, the biological half life or absorption of the protein. The moieties can also reduce or eliminate any desirable side effects of the proteins and the like. An overview for those moieties can be found in REMINGTON'S PHARMACEUTICAL SCIENCES, 20th ed., Mack Publishing Co., Easton, Pa. (2000).

The isolated polypeptides described herein can be produced by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g. Zoeller et al., Proc. Nat'l. Acad. Sci. USA 81:5662-5066 (1984) and U.S. Pat. No. 4,588,585.

In some embodiments a DNA sequence encoding a polypeptide of interest would be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis or another method), the polynucleotide sequences encoding a particular isolated polypeptide of interest will be inserted into an expression vector and operatively linked to an expression control sequence appropriate for expression of the protein in a desired host. Proper assembly can be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

In certain embodiments, recombinant expression vectors are used to amplify and express DNA encoding antibodies, or fragments thereof, against human EGFR. Recombinant expression vectors are replicable DNA constructs which have synthetic or cDNA-derived DNA fragments encoding a polypeptide chain of an anti-EGFR antibody, or fragment thereof, operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *Esherichia coli*, including pCR 1, pBR322, pMB9 and their derivatives, wider host range plasmids, such as M13 and filamentous single-stranded DNA phages.

Suitable host cells for expression of a EGFR-binding polypeptide or antibody (or a EGFR protein to use as an antigen) include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin as described below. Cell-free translation systems could also be employed. Appropriate cloning and expression vectors for use with bacterial, fungal, yeast, and mammalian cellular hosts are described by Pouwels et al. (Cloning Vectors: A Laboratory Manual, Elsevier, N.Y., 1985), the relevant disclosure of which is hereby incorporated by reference. Additional information regarding methods of protein production, including antibody production, can be found, e.g., in U.S. Patent Publication No. 2008/0187954, U.S. Pat. Nos. 6,413, 746 and 6,660,501, and International Patent Publication No. WO 04009823, each of which is hereby incorporated by reference herein in its entirety.

Various mammalian or insect cell culture systems are also advantageously employed to express recombinant protein. Expression of recombinant proteins in mammalian cells can be performed because such proteins are generally correctly folded, appropriately modified and completely functional. Examples of suitable mammalian host cell lines include the COS-7 lines of monkey kidney cells, described by Gluzman (Cell 23:175, 1981), and other cell lines capable of expressing an appropriate vector including, for example, L cells, C127, 3T3, Chinese hamster ovary (CHO), HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, Bio/Technology 6:47 (1988).

The proteins produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexahistidine, maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify a EGFR-binding agent. Some or all of the foregoing purification steps, in various combinations, can also be employed to provide a homogeneous recombinant protein.

Recombinant protein produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying antibodies and other proteins also include, for example, those described in U.S. Patent Publication No. 2008/0312425, 2008/0177048, and 2009/0187005, each of which is hereby incorporated by reference herein in its entirety.

In certain embodiments, the EGFR-binding agent is a polypeptide that is not an antibody. A variety of methods for identifying and producing non-antibody polypeptides that bind with high affinity to a protein target are known in the art. See, e.g., Skerra, Curr. Opin. Biotechnol., 18:295-304 (2007), Hosse et al., Protein Science, 15:14-27 (2006), Gill et al., Curr. Opin. Biotechnol., 17:653-658 (2006), Nygren, FEBS J., 275:2668-76 (2008), and Skerra, FEBS J., 275:2677-83 (2008), each of which is incorporated by reference herein in its entirety. In certain embodiments, phage display technology has been used to identify/produce the EGFR-binding polypeptide. In certain embodiments, the polypeptide comprises a protein scaffold of a type selected from the group consisting of protein A, a lipocalin, a fibronectin domain, an ankyrin consensus repeat domain, and thioredoxin.

In some embodiments, the agent is a non-protein molecule. In certain embodiments, the agent is a small molecule. Combinatorial chemistry libraries and techniques useful in the identification of non-protein EGFR-binding agents are known to those skilled in the art. See, e.g., Kennedy et al., J. Comb. Chem., 10:345-354 (2008), Dolle et al, J. Comb. Chem., 9:855-902 (2007), and Bhattacharyya, Curr. Med. Chem., 8:1383-404 (2001), each of which is incorporated by reference herein in its entirety. In certain further embodiments, the agent is a carbohydrate, a glycosaminoglycan, a glycoprotein, or a proteoglycan.

In certain embodiments, the agent is a nucleic acid aptamer. Aptamers are polynucleotide molecules that have been selected (e.g., from random or mutagenized pools) on the basis of their ability to bind to another molecule. In some embodiments, the aptamer comprises a DNA polynucleotide. In certain alternative embodiments, the aptamer comprises an RNA polynucleotide. In certain embodiments, the aptamer comprises one or more modified nucleic acid residues. Methods of generating and screening nucleic acid aptamers for binding to proteins are well known in the art. See, e.g., U.S. Pat. No. 5,270,163, U.S. Pat. No. 5,683,867, U.S. Pat. No. 5,763,595, U.S. Pat. No. 6,344,321, U.S. Pat. No. 7,368,236, U.S. Pat. No. 5,582,981, U.S. Pat. No. 5,756,291, U.S. Pat. No. 5,840,867, U.S. Pat. No. 7,312,325, U.S. Pat. No. 7,329,742, International Patent Publication No. WO 02/077262, International Patent Publication No. WO 03/070984, U.S. Patent Application Publication No. 2005/0239134, U.S. Patent Application Publication No. 2005/0124565, and U.S. Patent Application Publication No. 2008/0227735, each of which is incorporated by reference herein in its entirety.

III. Immunoconjugates

The present invention is also directed to conjugates (also referred to herein as immunoconjugates), comprising the anti-EGFR antibodies, antibody fragments, and their functional equivalents as disclosed herein, linked or conjugated to a drug or prodrug. Suitable drugs or prodrugs are known in the art. The drugs or prodrugs can be cytotoxic agents. The cytotoxic agent used in the cytotoxic conjugate of the present invention can be any compound that results in the death of a cell, or induces cell death, or in some manner decreases cell viability, and includes, for example, maytansinoids and maytansinoid analogs. Other suitable cytotoxic agents are for example benzodiazepines, taxoids, CC-1065 and CC-1065 analogs, duocarmycins and duocarmycin analogs, enediynes, such as calicheamicins, dolastatin and dolastatin analogs including auristatins, tomaymycin derivatives, leptomycin derivaties, methotrexate, cisplatin, carboplatin, daunorubicin, doxorubicin, vincristine, vinblastine, melphalan, mitomycin C, chlorambucil and morpholino doxorubicin.

Such conjugates can be prepared by using a linking group in order to link a drug or prodrug to the antibody or functional equivalent. Suitable linking groups are well known in the art and include, for example, disulfide groups, thioether groups, acid labile groups, photolabile groups, peptidase labile groups and esterase labile groups.

The drug or prodrug can, for example, be linked to the anti-EGFR antibody or fragment thereof through a disulfide bond. The linker molecule or crosslinking agent comprises a reactive chemical group that can react with the anti-EGFR antibody or fragment thereof. The reactive chemical groups for reaction with the cell-binding agent can be N-succinimidyl esters and N-sulfosuccinimidyl esters. Additionally the linker molecule comprises a reactive chemical group, which can be a dithiopyridyl group that can react with the drug to form a disulfide bond. Linker molecules include, for example, N-succinimidyl 3-(2-pyridyldithio) propionate (SPDP) (see, e.g., Carlsson et al., Biochem. J., 173: 723-737 (1978)), N-succinimidyl 4-(2-pyridyldithio)butanoate (SPDB) (see, e.g., U.S. Pat. No. 4,563,304), N-succinimidyl 4-(2-pyridyldithio)-2-sulfobutanoate (sulfo-SPDB) (see US Publication No. 20090274713), N-succinimidyl 4-(2-pyridyldithio) pentanoate (SPP) (see, e.g., CAS Registry number 341498-08-6), 2-iminothiolane, or acetylsuccinic anhydride. For example, the antibody or cell binding agent can be modified with crosslinking reagents and the antibody or cell binding agent containing free or protected thiol groups thus derived is then reacted with a disulfide- or thiol-containing maytansinoid to produce conjugates. The conjugates can be purified by chromatography, including but not limited to HPLC, size-exclusion, adsorption, ion exchange and affinity capture, dialysis or tangential flow filtration.

In another aspect of the present invention, the anti-EGFR antibody is linked to cytotoxic drugs via disulfide bonds and a polyethylene glycol spacer in enhancing the potency, solubility or the efficacy of the immunoconjugate. Such cleavable hydrophilic linkers are described in WO2009/0134976. The additional benefit of this linker design is the desired high monomer ratio and the minimal aggregation of the antibody-drug conjugate. Specifically contemplated in this aspect are conjugates of cell-binding agents and drugs linked via disulfide group (—S—S—) bearing polyethylene glycol spacers $((CH_2CH_2O)_{n=1-14})$ with a narrow range of drug load of 2-8 are described that show relatively high potent biological activity toward cancer cells and have the desired biochemical properties of high conjugation yield and high monomer ratio with minimal protein aggregation.

Specifically contemplated in this aspect is an anti-EGFR antibody drug conjugate of formula (I) or a conjugate of formula (I'):

$$CB-[X_{l'}-(-CH_2-CH_2O-)_n-Y-D]_m \qquad (I)$$

$$[D-Y-(-CH_2-CH_2O-)_n-X_l]_m-CB \qquad (I')$$

wherein:
CB represents an anti-EGFR antibody or fragment;
D represents a drug;
X represents an aliphatic, an aromatic or a heterocyclic unit attached to the cell-binding agent via a thioether bond, an amide bond, a carbamate bond, or an ether bond;
Y represents an aliphatic, an aromatic or a heterocyclic unit attached to the drug via a disulfide bond;
l is 0 or 1;
m is an integer from 2 to 8; and
n is an integer from 1 to 24.

In some embodiments, m is an integer from 2 to 6.
In some embodiments, m is an integer from 3 to 5.
In some embodiments, n is an integer form 2 to 8. Alternatively, as disclosed in, for example, U.S. Pat. Nos. 6,441,163 and 7,368,565, the drug can be first modified to introduce a reactive ester suitable to react with a cell-binding agent. Reaction of these drugs containing an activated linker moiety with a cell-binding agent provides another method of producing a cell-binding agent drug conjugate. Maytansinoids can also be linked to anti-EGFR antibody or fragment using PEG linking groups, as set forth for example in U.S. Pat. No. 6,716,821. These PEG non-cleavable linking groups are soluble both in water and in non-aqueous solvents, and can be used to join one or more cytotoxic agents to a cell binding agent. Exemplary PEG linking groups include heterobifunctional PEG linkers that react with cytotoxic agents and cell binding agents at opposite ends of the linkers through a functional sulfhydryl or disulfide group at one end, and an active ester at the other end. As a general example of the synthesis of a cytotoxic conjugate using a PEG linking group, reference is again made to U.S. Pat. No. 6,716,821 which is incorporated entirely by reference herein. Synthesis begins with the reaction of one or more cytotoxic agents bearing a reactive PEG moiety with a cell-binding agent, resulting in displacement of the terminal active ester of each reactive PEG moiety by an amino acid residue of the cell binding agent, to yield a cytotoxic conjugate comprising one or more cytotoxic agents covalently bonded to a cell binding agent through a PEG linking group. Alternatively, the cell binding can be modified with the bifunctional PEG crosslinker to introduce a reactive disulfide moiety (such as a pyridyldisulfide), which can then be treated with a thiol-containing maytansinoid to provide a conjugate. In another method, the cell binding can be modified with the bifunctional PEG crosslinker to introduce a thiol moiety which can then can be treated with a reactive disulfide-containing maytansinoid (such as a pyridyldisulfide), to provide a conjugate.

Antibody-maytansinoid conjugates with non-cleavable links can also be prepared. Such crosslinkers are described in the art (see US Publication No. 20050169933) and include but are not limited to, N-succinimidyl 4-(maleimidomethyl)cyclohexanecarboxylate (SMCC). In some embodiments, the antibody is modified with crosslinking reagents such as succinimidyl 4-(N-maleimidomethyl)-cyclohexane-1-carboxylate (SMCC), sulfo-SMCC, maleimidobenzoyl-N-hydroxysuccinimide ester (MBS), sulfo-MBS or succinimidyl-iodoacetate, as described in the literature, to introduce 1-10 reactive groups (Yoshitake et al, Eur. J. Biochem., 101:395-399 (1979); Hashida et al, J. Applied Biochem., 56-63 (1984); and Liu et al, Biochem., 18:690-697 (1979)). The modified antibody is then reacted with the thiol-containing maytansinoid derivative to produce a conjugate. The conjugate can be purified by gel filtration through a Sephadex G25 column or by dialysis or tangential flow filtration. The modified antibodies are treated with the thiol-containing maytansinoid (1 to 2 molar equivalent/maleimido group) and antibody-maytansinoid conjugates are purified by gel filtration through a Sephadex G-25 column, chromatography on a ceramic hydroxyapatite column, dialysis or tangential flow filtration or a combination of methods thereof. Typically, an average of 1-10 maytansinoids per antibody are linked. One method is to modify antibodies with succinimidyl 4-(N-maleimidomethyl)-cyclohexane-1-carboxylate (SMCC) to introduce maleimido groups followed by reaction of the modified antibody with a thiol-containing maytansinoid to give a thioether-linked conjugate. Again conjugates with 1 to 10 drug molecules per antibody molecule result. Maytansinoid conjugates of antibodies, antibody fragments, and other proteins are made in the same way.

In another aspect of the invention, the EGFR antibody is linked to the drug via a non-cleavable bond through the intermediacy of a PEG spacer. Suitable crosslinking reagents comprising hydrophilic PEG chains that form linkers between a drug and the anti-EGFR antibody or fragment are also well known in the art, or are commercially available (for example from Quanta Biodesign, Powell, Ohio). Suitable PEG-containing crosslinkers can also be synthesized from commercially available PEGs themselves using standard synthetic chemistry techniques known to one skilled in the art. The drugs can be reacted with bifunctional PEG-containing cross linkers to give compounds of the following formula, Z-$X_{l'}$-(—$CH_2$—$CH_2$—O—)$_n$-$Y_p$-D, by methods described in detail in US Patent Publication 20090274713 and in WO2009/0134976, which can then react with the cell binding agent to provide a conjugate. Alternatively, the cell binding can be modified with the bifunctional PEG crosslinker to introduce a thiol-reactive group (such as a maleimide or haloacetamide) which can then be treated with a thiol-containing maytansinoid to provide a conjugate. In another method, the cell binding can be modified with the bifunctional PEG crosslinker to introduce a thiol moiety which can then be treated with a thiol-reactive maytansinoid (such as a maytansinoid bearing a maleimide or haloacetamide), to provide a conjugate.

Accordingly, another aspect of the present invention is an anti-EGFR antibody drug conjugate of formula (II) or of formula (II'):

$$CB-[X_{l'}-(-CH_2-CH_2-O-)_n-Y_p-D]_m \qquad (II)$$

$$[D-Y_p-(-CH_2-CH_2-O-)_n-X_l]_m-CB \qquad (II')$$

wherein, CB represents an anti-EGFR antibody or fragment;

D represents a drug;

X represents an aliphatic, an aromatic or a heterocyclic unit bonded to the cell-binding agent via a thioether bond, an amide bond, a carbamate bond, or an ether bond;

Y represents an aliphatic, an aromatic, or a heterocyclic unit bonded to the drug via a covalent bond selected from the group consisting of a thioether bond, an amide bond, a carbamate bond, an ether bond, an amine bond, a carbon-carbon bond and a hydrazone bond;

l is 0 or 1;

p is 0 or 1;

m is an integer from 2 to 15; and n is an integer from 1 to 2000.

In some embodiments, m is an integer from 2 to 8; and

In some embodiments, n is an integer from 1 to 24.

In some embodiments, m is an integer from 2 to 6.

In some embodiments, m is an integer from 3 to 5.

In some embodiments, n is arm integer from 2 to 8. Examples of suitable PEG-containing linkers include linkers having an N-succinimidyl ester or N-sulfosuccinimidyl ester moiety for reaction with the anti-EGFR antibody or fragment thereof, as well as a maleimido- or haloacetyl-based moiety for reaction with the compound. A PEG spacer can be incorporated into any crosslinker known in the art by the methods described herein.

Many of the linkers disclosed herein are described in detail in U.S. Patent Publication Nos. 20050169933 and 20090274713, and in WO2009/0134976; the contents of which are entirely incorporated herein by reference.

The present invention includes aspects wherein about 2 to about 8 drug molecules ("drug load"), for example, maytansinoid, are linked to an anti-EGFR antibody or fragment thereof, the anti-tumor effect of the conjugate is much more efficacious as compared to a drug load of a lesser or higher number of drugs linked to the same cell binding agent. "Drug load", as used herein, refers to the number of drug molecules (e.g., a maytansinoid) that can be attached to a cell binding agent (e.g., an anti-EGFR antibody or fragment thereof). In one aspect the number of drug molecules that can be attached to a cell binding agent can average from about 2 to about 8 (e.g., 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1). $N^{2'}$-deacetyl-$N^{2'}$-(3-mercapto-1-oxopropyl)-maytansine (DM1) and $N^2$-deacetyl-$N^{2'}$-(4-mercapto-4-methyl-1-oxopentyl) maytansine (DM4) can be used.

The anti-EGFR antibody or fragment thereof can be modified by reacting a bifunctional crosslinking reagent with the anti-EGFR antibody or fragment thereof, thereby resulting in the covalent attachment of a linker molecule to the anti-EGFR antibody or fragment thereof. As used herein, a "bifunctional crosslinking reagent" is any chemical moiety that covalently links a cell-binding agent to a drug, such as the drugs described herein. In another method, a portion of the linking moiety is provided by the drug. In this respect, the drug comprises a linking moiety that is part of a larger linker molecule that is used to join the cell-binding agent to the drug. For example, to form the maytansinoid DM1, the side chain at the C-3 hydroxyl group of maytansine is modified to have a free sulfhydryl group (SH). This thiolated form of maytansine can react with a modified cell-binding agent to form a conjugate. Therefore, the final linker is assembled from two components, one of which is provided by the crosslinking reagent, while the other is provided by the side chain from DM1.

The drug molecules can also be linked to the antibody molecules through an intermediary carrier molecule such as serum albumin.

As used herein, the expression "linked to a cell-binding agent" or "linked to an anti-EGFR antibody or fragment" refers to the conjugate molecule comprising at least one drug derivative bound to a cell-binding agent anti-EGFR antibody or fragment via a suitable linking group, or a precursor thereof. One linking group is SMCC.

In certain embodiments, cytotoxic agents useful in the present invention are maytansinoids and maytansinoid analogs. Examples of suitable maytansinoids include esters of maytansinol and maytansinol analogs. Included are any drugs that inhibit microtubule formation and that are highly toxic to mammalian cells, as are maytansinol and maytansinol analogs.

Examples of suitable maytansinol esters include those having a modified aromatic ring and those having modifications at other positions. Such suitable maytansinoids are disclosed in U.S. Pat. Nos. 4,424,219; 4,256,746; 4,294,757; 4,307,016; 4,313,946; 4,315,929; 4,331,598; 4,361,650; 4,362,663; 4,364,866; 4,450,254; 4,322,348; 4,371,533; 5,208,020; 5,416,064; 5,475,092; 5,585,499; 5,846,545; 6,333,410; 7,276,497 and 7,473,796.

In a certain embodiment, the immunoconjugates of the invention utilize the thiol-containing maytansinoid (DM1), formally termed $N^{2'}$-deacetyl-$N^{2'}$-(3-mercapto-1-oxopropyl)-maytansine, as the cytotoxic agent. DM1 is represented by the following structural formula (III):

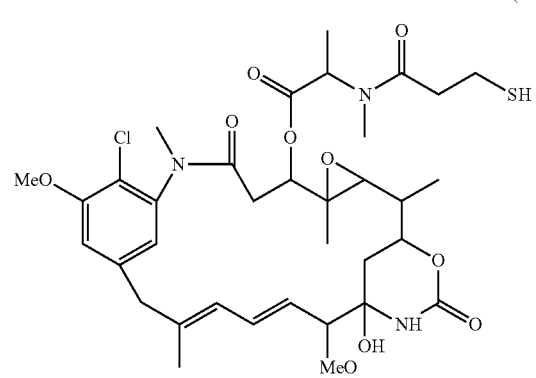

(III)

In another embodiment, the conjugates of the present invention utilize the thiol-containing maytansinoid $N^{2'}$-deacetyl-$N^{2'}$(4-methyl-4-mercapto-1-oxopentyl)-maytansine (e.g., DM4) as the cytotoxic agent. DM4 is represented by the following structural formula (IV):

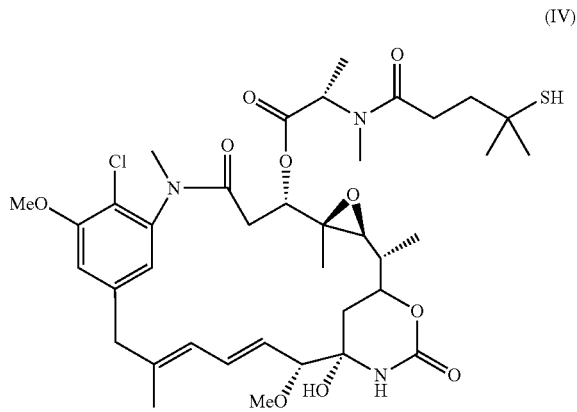 [SMILES: COc1cc2cc(c1Cl)N(C)C(=O)C[C@H](OC(=O)[C@H](C)N(C)C(=O)CCC(C)(C)S)[C@]1(C)O[C@H]1[C@H](C)C1C[C@@](O)(NC(=O)O1)[C@H](OC)/C=C/C=C(\C)C2]

(IV)

Another maytansinoid comprising a side chain that contains a sterically hindered thiol bond is $N^{2'}$-deacetyl-$N$-$^{2'}$(4- mercapto-1-oxopentyl)-maytansine (termed DM3), represented by the following structural formula (V):

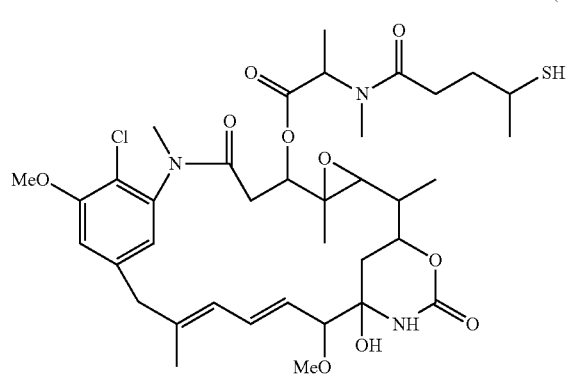

(V)

Each of the maytansinoids taught in U.S. Pat. Nos. 5,208,020 and 7,276,497, can also be used in the conjugate of the present invention. In this regard, the entire disclosure of U.S. Pat. No. 5,208,020 and U.S. Pat. No. 7,276,697 is incorporated herein by reference.

Many positions on maytansinoids can serve as the position to chemically link the linking moiety. For example, the C-3 position having a hydroxyl group, the C-14 position modified with hydroxymethyl, the C-15 position modified with hydroxy and the C-20 position having a hydroxy group are all expected to be useful. In some embodiments, the C-3 position serves as the position to chemically link the linking moiety, and in some particular embodiments, the C-3 position of maytansinol serves as the position to chemically link the linking moiety.

Structural representations of some conjugates are shown below:

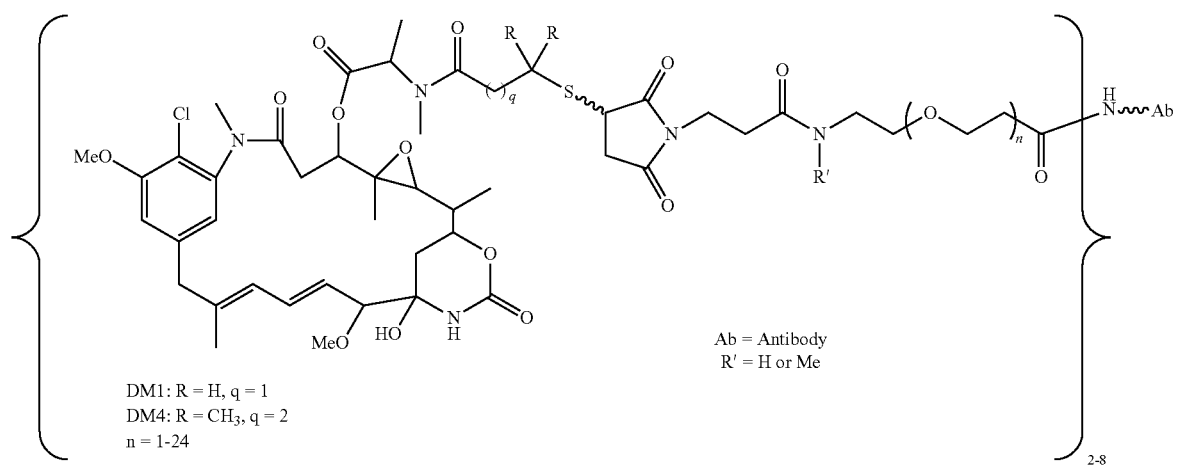

(VI)

DM1: R = H, q = 1
DM4: R = CH$_3$, q = 2
n = 1-24

Ab = Antibody
R' = H or Me

Ab-PEG-Mal-DM1/DM4

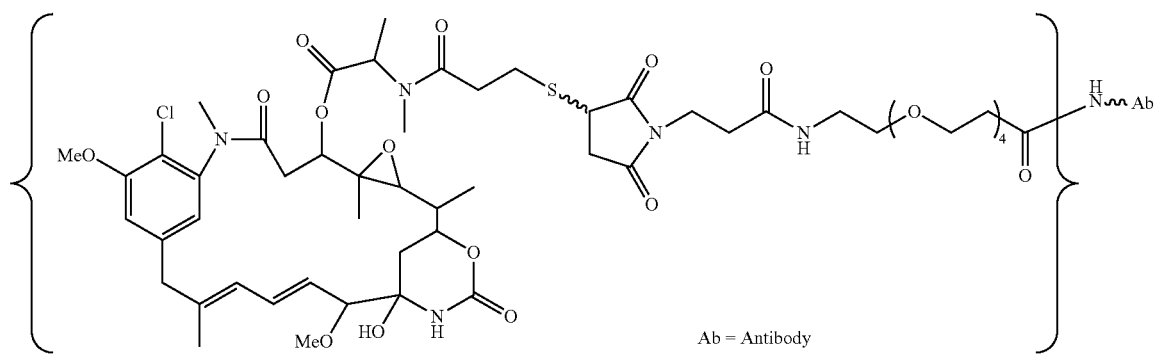

(VII)

Ab = Antibody

Ab-PEG4-Mal-DM1

(VIII)
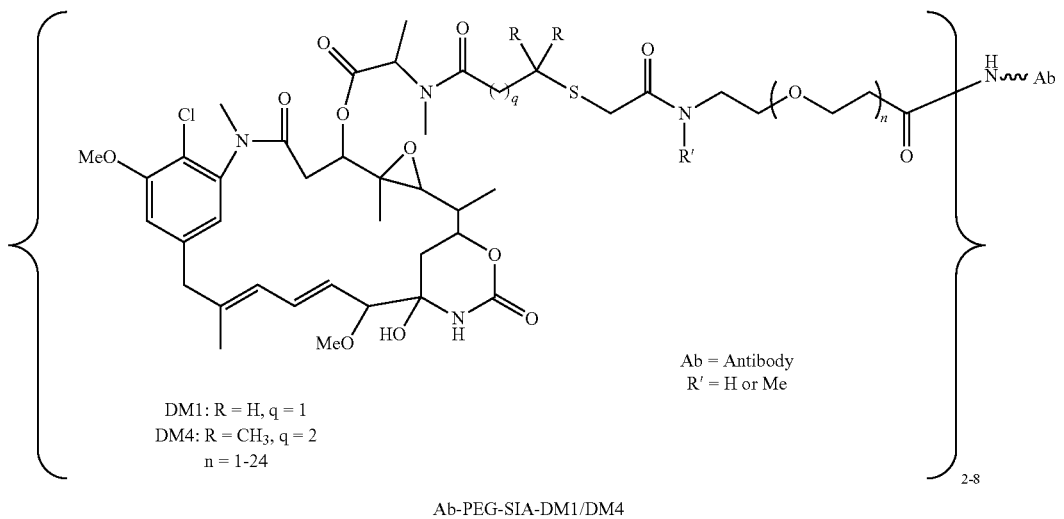
Ab-PEG-SIA-DM1/DM4
(IX)
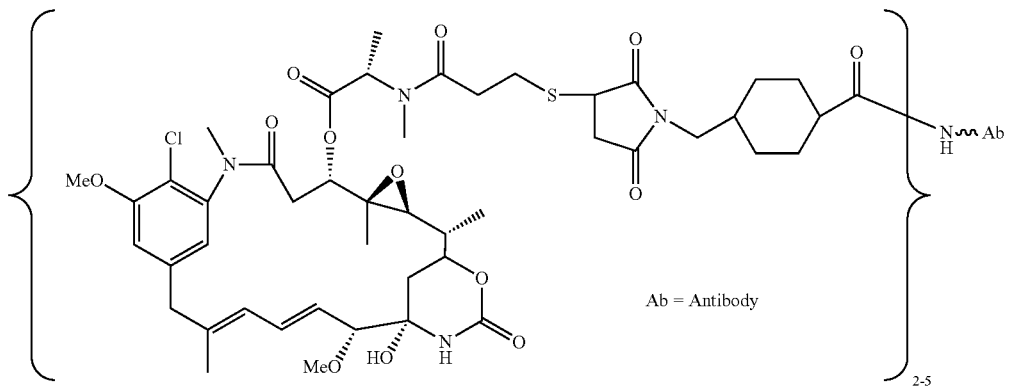
Ab-SMCC-DM1
(X)
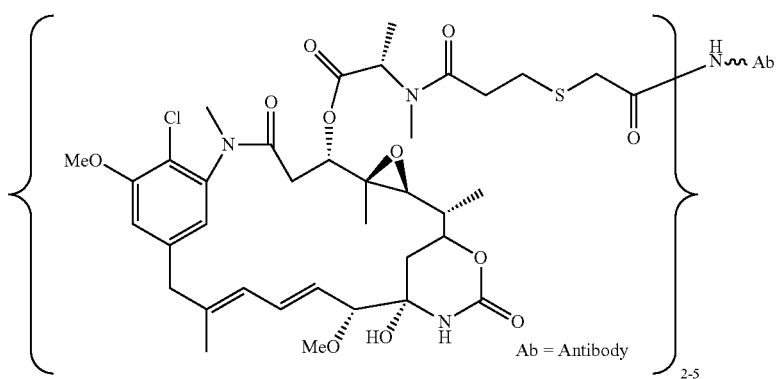
Ab-SIA-DM1

(XI)

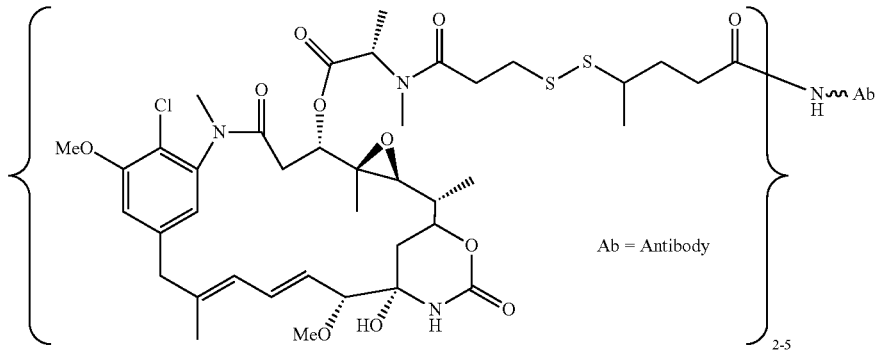

Ab-SPP-DM1

(XII)

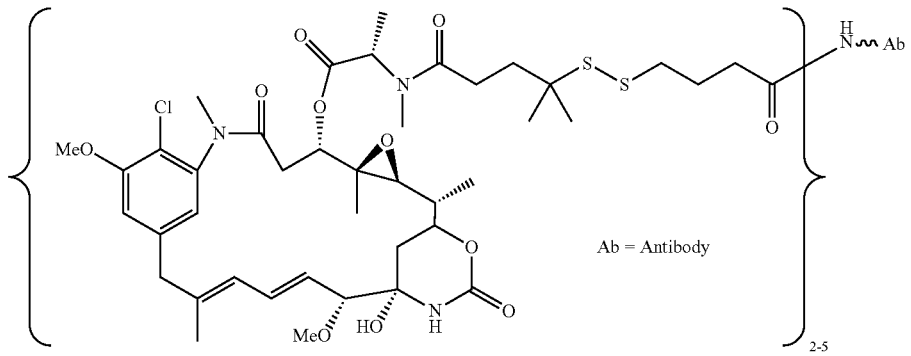

Ab-SPDB-DM4

(XIII)

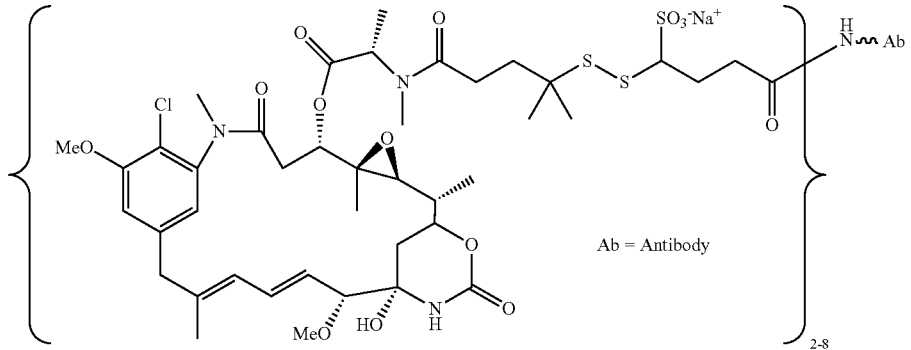

Ab-sulfo-SPDB-DM4

Several descriptions for producing such antibody-maytansinoid conjugates are provided in U.S. Pat. Nos. 6,333,410, 6,441,163, 6,716,821, and 7,368,565, each of which is incorporated herein in its entirety.

In general, a solution of an antibody in aqueous buffer can be incubated with a molar excess of maytansinoids having a disulfide moiety that bears a reactive group. The reaction mixture can be quenched by addition of excess amine (such as ethanolamine, taurine, etc.). The maytansinoid-antibody conjugate can then be purified by gel filtration.

The number of maytansinoid molecules bound per antibody molecule can be determined by measuring spectrophotometrically the ratio of the absorbance at 252 nm and 280 nm. The average number of maytansinoid molecules/antibody can be, for example, 1-10 or 2-5.

Anthracycline compounds, as well as derivatives, intermediates and modified versions thereof, can also be used to prepare anti-EGFR immunoconjugates. For example, doxorubicin, doxorubicin derivatives, doxorubicin intermediates, and modified doxorubicins can be used in anti-EGFR conjugates. Exemplary compounds are described in WO 2010/009124, which is herein incorporated by reference in its entirety. Such compounds include, for example, compounds of the following formula:

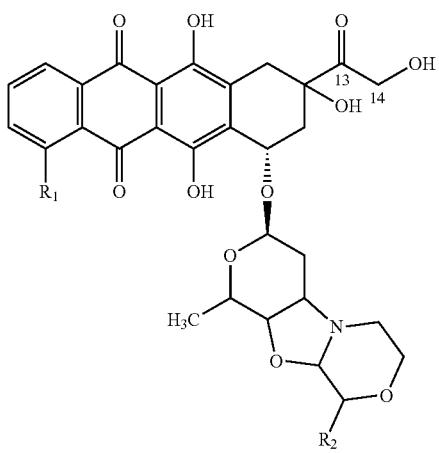

wherein R₁ is a hydrogen atom, hydroxy or methoxy group and R₂ is a $C_1$-$C_5$ alkoxy group, or a pharmaceutically acceptable salt thereof.

Conjugates of antibodies with maytansinoid or other drugs can be evaluated for their ability to suppress proliferation of various unwanted cell lines in vitro. For example, cell lines such NCI-H226, NCI-H292, and NCI-H322M, can easily be used for the assessment of cytotoxicity of these compounds. Cells to be evaluated can be exposed to the compounds for 4 to 5 days and the surviving fractions of cells measured in direct assays by known methods. $IC_{50}$ values can then be calculated from the results of the assays.

The immunoconjugates can, according to some embodiments described herein, be internalized into cells. The immunocongugate, therefore, can exert a therapeutic effect when it is taken up by, or internalized, by a EGFR-expressing cell. In some particular embodiments, the immunoconjugate comprises an antibody, antibody fragment, or polypeptide, linked to a cytotoxic agent by a cleavable linker, and the cytotoxic agent is cleaved from the antibody, antibody fragment, or polypeptide, wherein it is internalized by a EGFR-expressing cell.

In some embodiments, the immunoconjugates are capable of reducing tumor volume. For example, in some embodiments, treatment with an immunoconjugate results in a % T/C value that is less than about 50%, less than about 45%, less than about 40%, less than about 35%, less than about 30%, less than about 25%, less than about 20%, less than about 15%, less than about 10%, or less than about 5%.

In another aspect of the invention siRNA molecules can be linked to the antibodies of the present invention instead of a drug. siRNAs can be linked to the antibodies of the present invention by methods commonly used for the modification of oligonucleotides (see, for example, US Patent Publications 20050107325 and 20070213292). Thus the siRNA in its 3' or 5'-phosphoromidite form can be reacted with one end of the crosslinker bearing a hydroxyl functionality to give an ester bond between the siRNA and the crosslinker. Similarly reaction of the siRNA phosphoramidite with a crosslinker bearing a terminal amino group results in linkage of the crosslinker to the siRNA through an amine. Alternatively, the siRNA can be derivatized by standard chemical methods to introduce a thiol group. This thiol-containing siRNA can be reacted with an antibody that has been modified to introduce an active disulfide or maleimide moiety, to produce a cleavable or non cleavable conjugate. Between 1-20 siRNA molecules can be linked to an antibody by this method.

III. Polynucleotides

In certain embodiments, the invention encompasses polynucleotides that encode a polypeptide that specifically binds EGFR or a fragment of such a polypeptide. For example, the invention provides a polynucleotide comprising a nucleic acid sequence that encodes an antibody to a human EGFR or encodes a fragment of such an antibody. The polynucleotides of the invention can be in the form of RNA or in the form of DNA. DNA includes cDNA, genomic DNA, and synthetic DNA; and can be double-stranded or single-stranded, and if single stranded can be the coding strand or non-coding (anti-sense) strand.

In certain embodiments, the polynucleotides are isolated. In certain embodiments, the polynucleotides are substantially pure.

The invention provides a polynucleotide comprising a polynucleotide encoding a polypeptide comprising a sequence selected from the group consisting of SEQ ID NOs: 1-28.

The invention further provides a polynucleotide comprising a sequence selected from those shown in Tables 7-9 below.

TABLE 7

Variable heavy chain polynucleotide sequences

| Antibody | VH Polynucleotide Sequence |
|---|---|
| ratML66 $V_H$ | caagtgcaactaaaggagtcaggacctggtctggtacag ccatcacagaccctgtctctcacctgcactgtctctggg ttatcattagccagcaatagtgtaagctggattcggcag cctccaggaaagggtctggagtggatgggagtaatatgg aatcatggaggcacagattataattcagttatcaaatcc cgactgagcatcagcagggacacctcgaagagccaagtt ttcttaaagatgaacagtctgcagactgaagacacagcc atgtacttctgtgtcagaaagggtgggatctactttgat tactgggtcaaggagtcatggtcacagtctcctca (SEQ ID NO: 29) |
| muEGFR-8 $V_H$ | gaggttcagctgcagcagtctggggcagagcttgtgaag ccaggggcctcagtcaagttgtcctgcacaacttctggc ttcaacattaaagacacctatatacactgggtgaagaag aggcctgaacagggcctggagtggattggaaggattgat cctacgaatggaaataataaatatgacccgaagttccag ggcaaggccactataacagcagacacatcttccaacaca gcctacctgcagctcagcagcctgacatctgaggacact gccgtctattactgtactagagaagatgggtataggtac gacgactggtacttcgatgtctggggcgcagggaccacg gtcaccgtctcctca (SEQ ID NO: 30) |
| huML66 $V_H$ | aagcttgccaccatgggttggtcttgcattatccttttc ctggttgcaacagccacaggcgttcacagtcaagtgcag ctgcaggaatccggccccggactggttaagcccagcgag accctctctctgacatgcacagtcagcgggctgagcttg gctagtaacagcgtcagttggatcaggcagcctcctggg aaggggctggagtggatgggagtaatctggaaccacggg ggtaccgactacaatccatctattaagagccgcctgagt atctcacgggacaccagcaaatctcaagtgtttctgaag atgaatagcctgactgcagccgatacagccatgtacttc tgtgtccggaagggtggcatttacttcgactattgggt cagggtgtcctggtgactgtctcttcagccagcaccaag ggccc (SEQ ID NO: 31) |
| huEGFR-8 $V_H$ | aagcttgccaccatgggctggtcatgcatcatcttgttt ttggtggcaactgccactggtgtccattctcaagtacag cttgtacagtcaggtgctgaagtcgtcaagcccggggcc agtgtcaagctgtcctgtactacatctggatttacaata aaagacacctacattcactgggtgaagaagaggcccggg caggggctggagtggattggccggattgatcccacaaat ggcaacaataaatatgaccagaaattccaaggcaaagcc accatcactgcagatacctcaagtaacactgcttacctg cagttgtcttctctgacatccgaggatacagccgtgtac tactgcactagagaggatggatacagatatgacgactgg tacttcgatgtggggccagggaccctggtcactgtttcc tccgcttccacaaagggccc (SEQ ID NO: 32) |

TABLE 9

Full-length heavy and light chain polynucleotide sequences

| Antibody | Polynucleotide Sequence |
|---|---|
| huML66 HC | aagcttgccaccatgggttggtcttgcattatccttttc ctggttgcaacagccacaggcgttcacagtcaagtgcag agcaggaatccggccccggactggttaagcccagcgaga ccctctctctgacatgcacagtcagcgggctgagcttgg ctagtaacagcgtcagttggatcaggcagcctcctggga aggggctggagtggatgggagtaatctggaaccacgggg gtaccgactacaatccatctattaagagccgcctgagta tctcacgggacaccgacaaatctcaagtgttttctgaaga tgaatagcctgactgcagccgatacagccatgtacttct gtgtccggaagggtggcatttacttcgactattgggtc agggtgtcctgctgactgtctcttcagccagcaccaagg gcccatcagtttttccccttggctccaagttctaaatcca caagcggtggaacagctgcactgggatcctcgttaaaga ttatttccctgagcctgtgacagtgagctggaatagcgg agcattgacttcaggtgtgcacacttttcccgctgtgtt gcagtcctccggtctgtactcactgtccagtgtcgtaac cgtcccttctagcagcttgggaacccagacctacatctg taacgtcaaccataaaccatccaacacaaaggtggataa gaaggttgaaccaaagagctgtgataagacacatacatg ccctccttgtcctgcaccagagctcctcggaggtccatc tgtgttcctgtttccccccaaaccaaggacactcttat gatctctcgtactccagaggtcacctgtgttgttgtcga cgtgagccatgaagatcccgaggttaaattcaactggta gctggatggagtcgaggttcacaatgccaagaccagcc cagggaggagcaataataattctacatatcgggtagtga cgttctgaccgtgctccaccaagattggctcaatggaaa agagtacaagtgcaaggtgtccaacaaggctcttcccgc tcccattgagaaaactatctccaaagccaaggggcagcc acgggaacccagggtgtatacattgcccccatctagaga cgagctgaccaagaaccaggtgagtctcacttgtctggt caaggggttttaccttctgacattgctgtagagtggga gtctaacggacagccagaaaacaactacaagacaactcc cccagtgctggacagcgacgggagcttcttcctctactc caagttgactgtagacaagtctagatggcagcaaggaaa cgttttctcctgctcagtaatgcatgaggctctgcacaa tcactataccagaaatcactgtcccttagcccagggtg actcgag (SEQ ID NO: 37) |
| huML66 LC | gaattcgccaccatgggatggtcctgtataatcctgttt ctggtcgcaaccgcaaccggcgtgcactccgacactgtg ctgacacagtccccaagcctggctgtttcacctggtgaa agagctaccatcagttgtcgggctagcgaaagcgtgtca actctgatgcactggtaccagcagaagcctggccaacag cccaaactgctgatatatctggcatcacatcgtgagtcc ggagtacctgctaggttctctgggagcggcagcggcacc gactttaccctgacaatcgaccccatggaggccgaagat acagctacttactactgccaacagtctagaaacgatcca tggactttggacaagggaccaaattggagcttaagcgt acggtggctgcaccatctgtcttcatcttcccgccatct gatgagcagttgaaatctggaactgcctctgttgtgtgc ctgctgaataacttctatcccagagaggccaaagtacag tggaaggtggataacgccctccaatcgggtaactcccag gagagtgtcacagagcaggacagcaaggacagcacctac agcctcagcagcaccctgacgctgagcaaagcagactac gagaaacacaaagtctacgcctgcgaagtcacccatcag ggcctgagctcgcccgtcacaaagagcttcaacagggga gagtgttag (SEQ ID NO: 38) |
| huEGFR-8 HC | aagcttgccaccatgggctggtcatgcatcatcttgttt ttggtggcaactgccactggtgtccattctcaagtacag cttgtacagtcaggtgctgaagtcgtcaagcccggggcc agtgtcaagttcctgtactacatctggatttacaata aaagacacctacattcactgggtgaagaagaggcccggg cagggctggagtggattggccggattgatcccacaaat ggcaacaataaatatgaccagaaattccaaggcaaagcc accatcactgcagatacctcaagtaacactgcttacctg cagtgtcttctctgacatccgaggatacagccgtgtac tactgcactagagaggatggatacagatatgacgactgg tacttcgatgtgtggggccaggggaccctggtcactgtt tcctccgcttccacaaagggcccatcagttttccccctg gctccagtctaaatccacaagcggtggaacagctgca ctgggatgcctcgttaaagattatttccctgagcctgtg acagtgagctggaatagcggagcattgacttcaggtgtg cacacttttcccgctgtgttgcagtcctccggtctgtac tcactgtccagtgtcgtaaccgtcccttctagcagcttg |
| | ggaacccagacctacatctgtaacgtcaaccataaacca tccaacacaaaggtggataagaaggttgaaccaaagagc tgtgataagacacatacatgccctccttgtcctgcacca gagctcctcggaggtccatctgtgttcctgtttccccccc aaacccaaggacactcttatgatctctcgtactccagag gtcacctgtgttgttgtcgacgtgagccatgaagatccc gaggttaaattcaactggtacgtggatggagtcgaggtt cacaatgccaagaccagcgggaggagcaataataat tctacatatcgggtagtgagcgttctgaccgtgctccac caagattggctcaatggaaaagagtacaagtgcaaggtg tccaacaaggctcttcccgctcccattgagaaaactatc tccaaagccaaggggcagccacgggaacccagggtgtat acattgccccccatctagagagcgagctgaccaagaaccag gtgagtctcacttgtctggtcaaggggttttaccttct gacattgctgtagagtgggagtctaacggacagccagaa aacaactacaagacaactccccccagtgctggacagcgac gggagcttcttcctctactccaagttgactgtagacaag tctagatggcagcaaggaaacgttttctcctgctcagta atgcatgaggctctgcacaatcactacccagaaatca ctgtcccttagcccagggtgactcgag (SEQ ID NO: 39) |
| huEGFR-8 LC | gaattcgccaccatggggtggtcctgtatcattctgttt ctggtagccacagctaccggcgtgcactccgacatcgtg ctgacacaatcccctgctttatgtcagcttcctccaggaa agaaagtgaccatgacctgctctgcctctagctctgtgt cctacatgcactggtatcagcagaagccagaccagagtc ctaagagatggatctacgctaccagtaaactggcttcgt gcgtgccatctcggcttttcaggaaggcggcagggaaccg actactcattgacaatatcctctatgggaggccgaagacg ctgcaacatactactgtcagcagtggagctcaaatccac tcacattcggacagggtacaaaactggagctgaagcgta cggtggctgcaccatctgtcttcatcttcccgccatctg atgagcagttgaaatctggaactgcctctgttgtgtgcc tgctgaataacttctatcccagagaggccaaagtacagt ggaaggtggataacgccctccaatcgggtaactcccagg agagtgtcacagagcaggacagcaaggacagcacctaca gcctcagcagcaccctgacgctgagcaaagcagactacg agaaacacaaagtctacgcctgcgaagtcacccatcagg gcctgagctcgcccgtcacaaagagcttcaacaggggag agtgttag (SEQ ID NO: 40) |

TABLE 8

Variable light chain polynucleotide sequences

| Antibody | VL Polynucleotide Sequence |
|---|---|
| ratML66 $V_L$ | gacactgtactgacccagtctcctgctttggctgtgtct ccaggagagagggttaccatctcctgtagggccagtgag agtgtcagtcacttatgcactggtaccaacagaaatca ggacagcaacccaaactcctcatctatctagcatcacac cgagaatctggggtccctgccaggttcagtggcagtggg tctgggacagacttcaccctcaccattgatcctatggag gctgatgacactgcaacctattactgtcagcagagtcgg aatgatccgtggacgttcggtggaggcaccaacctggaa ttgaaacgg (SEQ ID NO: 33) |
| muEGFR-8 $V_L$ | caaattgttctcacccagtctccagcaagcatgtctgct tctccaggggagaaggtcaccatgacctgcagtgccagc tcaagtgtaagttacatgcactggtaccagcagaagtca ggcacctccccccaaaagatggatctatgccacatccaaa ctggcttctggagtccctgctcgcttcagtggcagtggg tctgggacctcttactctctcacaatcagcagcatgagg gctgaagatgctgccacttattactgccagcagtggagt agtaatccactcacgttcggtgctgggaccaagctggag ctgaaacgg (SEQ ID NO: 34) |
| huML66 $V_L$ | gaattcgccaccatgggatggtcctgtataatcctgttt ctggtcgcaaccgcaaccggcgtgcactccgacactgtg ctgacacagtccccaagcctggctgtttcacctggtgaa agagctaccatcagttgtcgggctagcgaaagcgtgtca |

TABLE 8-continued

Variable light chain polynucleotide sequences

| Antibody | VL Polynucleotide Sequence |
|---|---|
| | actctgatgcactggtaccagcagaagcctggccaacag<br>cccaaactgctgatatatctggcatcacatcgtgagtcc<br>ggagtacctgctaggttctctgggagcggcagcggcacc<br>gactttaccctgacaatcgaccccatggaggccgaagat<br>acagctacttactactgccaacagtctagaaacgatcca<br>tggacttttggacaagggaccaaattggagcttaagcgt<br>acg (SEQ ID NO: 35) |
| huEGFR-8 V$_L$ | gaattcgccaccatggggtggtcctgtatcattctgttt<br>tctggtagccacagctaccggcgtgcactccgacatcgg<br>ctgacacaatccccctgcttttatgtcagcttctccagga<br>gagaaagtgaccatgacctgctctgcctctagctctgtg<br>tcctacatgcactggtatcagcagaagccagaccagagt<br>cctaagagatggatctacgctaccagtaaactggcttct<br>ggcgtgccatctcggttttcaggaagcggcagcgggacc<br>gactactcattgacaatatcctctatggaggccgaagac<br>gctgcaacatactactgtcagcagtggagctcaaatcca<br>ctcacattcggacagggtacaaaactggagctgaagcgt<br>acg (SEQ ID NO: 36) |

Also provided is a polynucleotide having at least about 95%, at least about 96%, at least about 97%, at least about 98%, or at least about 99% sequence identity to SEQ ID NOs:29-40. Thus, in certain embodiments, the polypeptide comprises (a) a polypeptide having at least about 95% sequence identity to SEQ ID NOs:29-32, 37, or 39, and/or (b) a polypeptide having at least about 95% sequence identity to SEQ ID NOs:33-36, 38, or 40. In certain embodiments, the polypeptide comprises (a) a polypeptide having the amino acid sequence of SEQ ID NOs: 29-32, 37, or 39; and/or (b) a polypeptide having the amino acid sequence of SEQ ID NOs: 33-36, 38, or 40.

In certain embodiments the polynucleotides comprise the coding sequence for the mature polypeptide fused in the same reading frame to a polynucleotide which aids, for example, in expression and secretion of a polypeptide from a host cell (e.g. a leader sequence which functions as a secretory sequence for controlling transport of a polypeptide from the cell). The polypeptide having a leader sequence is a preprotein and can have the leader sequence cleaved by the host cell to form the mature form of the polypeptide. The polynucleotides can also encode for a proprotein which is the mature protein plus additional 5' amino acid residues. A mature protein having a prosequence is a proprotein and is an inactive form of the protein. Once the prosequence is cleaved an active mature protein remains.

In certain embodiments the polynucleotides comprise the coding sequence for the mature polypeptide fused in the same reading frame to a marker sequence that allows, for example, for purification of the encoded polypeptide. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g. COS-7 cells) is used.

The present invention further relates to variants of the hereinabove described polynucleotides encoding, for example, fragments, analogs, and derivatives.

The polynucleotide variants can contain alterations in the coding regions, non-coding regions, or both. In some embodiments the polynucleotide variants contain alterations which produce silent substitutions, additions, or deletions, but do not alter the properties or activities of the encoded polypeptide. In some embodiments, nucleotide variants are produced by silent substitutions due to the degeneracy of the genetic code. Polynucleotide variants can be produced for a variety of reasons, e.g., to optimize codon expression for a particular host (change codons in the human mRNA to those preferred by a bacterial host such as E. coli).

Vectors and cells comprising the polynucleotides described herein are also provided.

IV. Methods of Use and Pharmaceutical Compositions

The EGFR-binding agents (including antibodies, immunoconjugates, and polypeptides) of the invention are useful in a variety of applications including, but not limited to, therapeutic treatment methods, such as the treatment of cancer. In certain embodiments, the agents are useful for inhibiting tumor growth, inducing differentiation, reducing tumor volume, and/or reducing the tumorigenicity of a tumor. The methods of use can be in vitro, ex vivo, or in vivo methods. In certain embodiments, the EGFR-binding agent or antibody or immunoconjugate, or polypeptide is not antagonistic of the human EGFR to which it binds.

In one aspect, anti-EGFR antibodies and immunoconjugates of the invention are useful for detecting the presence of EGFR in a biological sample. The term "detecting" as used herein encompasses quantitative or qualitative detection. In certain embodiments, a biological sample comprises a cell or tissue.

In one aspect, the invention provides a method of detecting the presence of EGFR in a biological sample. In certain embodiments, the method comprises contacting the biological sample with an anti-EGFR antibody under conditions permissive for binding of the anti-EGFR antibody to EGFR, and detecting whether a complex is formed between the anti-EGFR antibody and EGFR.

In one aspect, the invention provides a method of diagnosing a disorder associated with increased expression of EGFR. In certain embodiments, the method comprises contacting a test cell with an anti-EGFR antibody; determining the level of expression (either quantitatively or qualitatively) of EGFR by the test cell by detecting binding of the anti-EGFR antibody to EGFR; and comparing the level of expression of EGFR by the test cell with the level of expression of EGFR by a control cell (e.g., a normal cell of the same tissue origin as the test cell or a cell that expresses EGFR at levels comparable to such a normal cell), wherein a higher level of expression of EGFR by the test cell as compared to the control cell indicates the presence of a disorder associated with increased expression of EGFR. In certain embodiments, the test cell is obtained from an individual suspected of having a disorder associated with increased expression of EGFR. In certain embodiments, the disorder is a cell proliferative disorder, such as a cancer or a tumor.

In certain embodiments, a method of diagnosis or detection, such as those described above, comprises detecting binding of an anti-EGFR antibody to EGFR expressed on the surface of a cell or in a membrane preparation obtained from a cell expressing EGFR on its surface. In certain embodiments, the method comprises contacting a cell with an anti-EGFR antibody under conditions permissive for binding of the anti-EGFR antibody to EGFR, and detecting whether a complex is formed between the anti-EGFR antibody and EGFR on the cell surface. An exemplary assay for detecting binding of an anti-EGFR antibody to EGFR expressed on the surface of a cell is a "FACS" assay.

Certain other methods can be used to detect binding of anti-EGFR antibodies to EGFR. Such methods include, but are not limited to, antigen-binding assays that are well known in the art, such as western blots, radioimmunoassays, ELISA (enzyme linked immunosorbent assay), "sandwich" immunoassays, immunoprecipitation assays, fluorescent immunoassays, protein A immunoassays, and immunohistochemistry (IHC).

In certain embodiments, anti-EGFR antibodies are labeled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction.

In certain embodiments, anti-EGFR antibodies are immobilized on an insoluble matrix. Immobilization entails separating the anti-EGFR antibody from any EGFR that remains free in solution. This conventionally is accomplished by either insolubilizing the anti-EGFR antibody before the assay procedure, as by adsorption to a water-insoluble matrix or surface (Bennich et al., U.S. Pat. No. 3,720,760), or by covalent coupling (for example, using glutaraldehyde cross-linking), or by insolubilizing the anti-EGFR antibody after formation of a complex between the anti-EGFR antibody and EGFR, e.g., by immunoprecipitation.

Any of the above embodiments of diagnosis or detection can be carried out using an immunoconjugate of the invention in place of or in addition to an anti-EGFR antibody.

In certain embodiments, the disease treated with the EGFR-binding agent or antagonist (e.g., an anti-EGFR antibody) is a cancer. In certain embodiments, the cancer is characterized by EGFR expressing cells to which the EGFR-binding agent (e.g., antibody) binds.

In a further aspect, the invention is directed to an improved method for treating cell proliferation disorders wherein EGFR is expressed, particularly wherein EGFR is abnormally expressed (e.g. overexpressed), including cancers of the bladder, brain, head and neck, pancreas, lung, breast, ovary, colon, prostate, skin, and kidney, comprising administering a therapeutically effective amount of an anti-EGFR binding agent of the present invention to a human subject in need thereof. In another embodiment the antibody is humanized. In another preferred embodiment, the humanized antibody comprises modified CDRs which comprise substitutions at any position except those that are necessary to retain binding activity (e.g., the SDRs). Examples of cell proliferation disorders that can be treated by an anti-EGFR binding agent of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system.

Similarly, other cell proliferation disorders can also be treated by the anti-EGFR binding agents of the present invention. Examples of such cell proliferation disorders include, but are not limited to: adrenal cortex hyperplasia (Cushing's disease), congenital adrenal hyperplasia, endometrial hyperplasia, benign prostatic hyperplasia, breast hyperplasia, intimal hyperplasia, focal epithelial hyperplasia (Heck's disease), sebaceous hyperplasia, compensatory liver hyperplasia, and any other cell proliferation disease, besides neoplasia, located in an organ system listed above.

The present invention further provides methods for inhibiting tumor growth using the antibodies or other agents described herein. In certain embodiments, the method of inhibiting the tumor growth comprises contacting the cell with an EGFR-binding agent (e.g., antibody) in vitro. For example, an immortalized cell line or a cancer cell line that expresses EGFR is cultured in medium to which is added the antibody or other agent to inhibit tumor growth. In some embodiments, tumor cells are isolated from a patient sample such as, for example, a tissue biopsy, pleural effusion, or blood sample and cultured in medium to which is added an EGFR-binding agent to inhibit tumor growth.

In some embodiments, the method of inhibiting tumor growth comprises contacting the tumor or tumor cells with the EGFR-binding agent (e.g., antibody) in vivo. In certain embodiments, contacting a tumor or tumor cell with a EGFR-binding agent is undertaken in an animal model. For example, EGFR-binding agents can be administered to xenografts expressing one or more EGFRs that have been grown in immunocompromised mice (e.g. NOD/SCID mice) to inhibit tumor growth. In some embodiments, cancer stem cells are isolated from a patient sample such as, for example, a tissue biopsy, pleural effusion, or blood sample and injected into immunocompromised mice that are then administered a EGFR-binding agent to inhibit tumor cell growth. In some embodiments, the EGFR-binding agent is administered at the same time or shortly after introduction of tumorigenic cells into the animal to prevent tumor growth. In some embodiments, the EGFR-binding agent is administered as a therapeutic after the tumorigenic cells have grown to a specified size.

In certain embodiments, the method of inhibiting tumor growth comprises administering to a subject a therapeutically effective amount of a EGFR-binding agent. In certain embodiments, the subject is a human. In certain embodiments, the subject has a tumor or has had a tumor removed.

In certain embodiments, the tumor expresses the EGFR to which the EGFR-binding agent or antibody binds.

In addition, the invention provides a method of reducing the tumorigenicity of a tumor in a subject, comprising administering a therapeutically effective amount of a EGFR-binding agent to the subject. In certain embodiments, the tumor comprises cancer stem cells. In certain embodiments, the frequency of cancer stem cells in the tumor is reduced by administration of the agent.

The invention further provides methods of differentiating tumorigenic cells into non-tumorigenic cells comprising contacting the tumorigenic cells with a EGFR-binding agent (for example, by administering the EGFR-binding agent to a subject that has a tumor comprising the tumorigenic cells or that has had such a tumor removed.

The use of the EGFR-binding agents, polypeptides, or antibodies described herein to induce the differentiation of cells, including, but not limited to tumor cells, is also provided. For example, methods of inducing cells to differentiate comprising contacting the cells with an effective amount of a EGFR-binding agent (e.g., an anti-EGFR antibody) described herein are envisioned. Methods of inducing cells in a tumor in a subject to differentiate comprising administering a therapeutically effective amount of a EGFR-binding agent, polypeptide, or antibody to the subject are also provided. In certain embodiments, the tumor is a pancreatic tumor. In certain other embodiments, the tumor is a colon tumor. In some embodiments, the treatment methods comprise administering a therapeutically effective amount of the EGFR-binding agent, polypeptide, or antibody to the subject.

The present invention further provides pharmaceutical compositions comprising one or more of the EGFR-binding agents described herein. In certain embodiments, the pharmaceutical compositions further comprise a pharmaceutically acceptable vehicle. These pharmaceutical compositions find use in inhibiting tumor growth and treating cancer in human patients.

In certain embodiments, formulations are prepared for storage and use by combining a purified antibody or agent of the present invention with a pharmaceutically acceptable vehicle (e.g. carrier, excipient) (Remington, The Science and Practice of Pharmacy 20th Edition Mack Publishing, 2000). Suitable pharmaceutically acceptable vehicles include, but are not limited to, nontoxic buffers such as phosphate, citrate, and other organic acids; salts such as sodium chloride; antioxidants including ascorbic acid and methionine; preservatives (e.g. octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3-pentanol; and m-cresol); low molecular weight polypeptides (e.g. less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosacchandes, disaccharides, glucose, mannose, or dextrins; chelating agents such as EDTA; sugars such as sucrose, mannitol, trehalose or sorbitol; salt-forming counter-ions such as sodium; metal complexes (e.g. Zn-protein complexes); and non-ionic surfactants such as TWEEN or polyethylene glycol (PEG).

The pharmaceutical compositions of the present invention can be administered in any number of ways for either local or systemic treatment. Administration can be topical (such as to mucous membranes including vaginal and rectal delivery) such as transdermal patches, ointments, lotions, creams, gels, drops, suppositories, sprays, liquids and powders; pulmonary (e.g., by inhalation or insufflation of powders or aerosols, including by nebulizer; intratracheal, intranasal, epidermal and transdermal); oral; or parenteral including intravenous, intraarterial, subcutaneous, intraperitoneal or intramuscular injection or infusion; or intracranial (e.g., intrathecal or intraventricular) administration.

An antibody or immunoconjugate of the invention can be combined in a pharmaceutical combination formulation, or dosing regimen as combination therapy, with a second compound having anti-cancer properties. The second compound of the pharmaceutical combination formulation or dosing regimen can have complementary activities to the ADC of the combination such that they do not adversely affect each other. Pharmaceutical compositions comprising the EGFR-binding agent and the second anti-cancer agent are also provided.

For the treatment of the disease, the appropriate dosage of an antibody or agent of the present invention depends on the type of disease to be treated, the severity and course of the disease, the responsiveness of the disease, whether the antibody or agent is administered for therapeutic or preventative purposes, previous therapy, patient's clinical history, and so on all at the discretion of the treating physician. The antibody or agent can be administered one time or over a series of treatments lasting from several days to several months, or until a cure is effected or a diminution of the disease state is achieved (e.g. reduction in tumor size). Optimal dosing schedules can be calculated from measurements of drug accumulation in the body of the patient and will vary depending on the relative potency of an individual antibody or agent. The administering physician can easily determine optimum dosages, dosing methodologies and repetition rates. In certain embodiments, dosage is from 0.01 μg to 100 mg per kg of body weight, and can be given once or more daily, weekly, monthly or yearly. In certain embodiments, the antibody or other EGFR-binding agent is given once every two weeks or once every three weeks. In certain embodiments, the dosage of the antibody or other EGFR-binding agent is from about 0.1 mg to about 20 mg per kg of body weight. The treating physician can estimate repetition rates for dosing based on measured residence times and concentrations of the drug in bodily fluids or tissues.

The combination therapy can provide "synergy" and prove "synergistic", i.e. the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

VI. Kits Comprising EGFR Binding Agents

The present invention provides kits that comprise the antibodies, immunoconjugates or other agents described herein and that can be used to perform the methods described herein. In certain embodiments, a kit comprises at least one purified antibody against EGFR in one or more containers. In some embodiments, the kits contain all of the components necessary and/or sufficient to perform a detection assay, including all controls, directions for performing assays, and any necessary software for analysis and presentation of results. One skilled in the art will readily recognize that the disclosed antibodies, immunoconjugates or other agents of the present invention can be readily incorporated into one of the established kit formats which are well known in the art.

Further provided are kits comprising a EGFR-binding agent (e.g., a EGFR-binding antibody), as well as a second anti-cancer agent. In certain embodiments, the second anti-cancer agent is a chemotherapeutic agent (e.g., rituximab),

EXAMPLES

It is understood that the examples and embodiments described herein are for illustrative purposes only and that various modifications or changes in light thereof will be suggested to persons skilled in the art and are to be included within the spirit and purview of this application.

Example 1

Generation and Selection of Rat ML66 EGFR Antibody

To produce rat EGFR antibodies, Sprague Dawley female rats (Charles River Laboratory, Wilmington, Mass.) were injected subcutaneously with membrane prep of MDA-MB468 breast cancer cell line (ATCC) in Titermax adjuvant (Sigma Aldrich, St. Luis, Mo.). The immunization was repeated once with the same antigen in PBS three weeks after the first immunization. Three days before cell fusion, another dose of antigen was injected intraperitoneally. The rat spleen was collected according to standard animal protocols and was ground between two sterile, frosted microscopic slides to obtain a single cell suspension. After the red blood cell lysis with ACK lysing buffer, the spleen cells were then mixed with murine myeloma P3X63Ag8.653 cells (P3 cells) (J. F. Kearney et al. 1979, *J Immunol*, 123:1548-1550) at ratio of 1 P3 cells:3 spleen cells and the cells were fused using polyethelene glycol 1500 (Roche). To select for hybridomas, the fused cells were resuspended in RPMI-1640 medium containing hypoxanthine-aminopterin-thymidine (HAT) (Sigma Aldrich) and seeded into flat bottom 96-well plates at 200 µl/well. The plates were then incubated in 5% $CO_2$ incubator at 37° C. until hydridoma clones were ready for antibody screening.

Hybridoma culture supernatants were screened using whole cell ELISA with human EGFR expressing rat YB2/0 stable cells and wild type YB2/0 cells (ATCC). The hybridoma clones that only reacted with the EGFR expressing YB2/0 cell line, but not the parental cell line, were subcloned by limiting dilution. Stable subclones were cultured and the antibody was isotyped using commercial isotyping reagents (Roche). A total of 12 rat monoclonal antibodies specific to EGFR were obtained and ML66 clone was chosen because of its unique properties described in other Examples.

Generation and Selection of Murine EGFR-8 Antibody

To produce murine anti-EGFR antibodies, head and neck squamous carcinoma cell lines such as CA922 (Japanese Collection of Research Bioresources (JCRB), Shinjuku, Japan) and HSC4 (JCRB, Shinjuku, Japan) were injected subcutaneously into Balb/c female mice (Charles River Laboratory, Wilmington, Mass.) at the dose of $5 \times 10^6$ cells per mouse every 2 weeks for 5 times. Three days before being sacrificed for hybridoma generation, the immunized mice received intraperitoneal injection of another dose of antigen. The spleen from the mouse was collected according to standard animal protocols and was ground between two sterile, frosted microscopic slides to obtain a single cell suspension in RPMI-1640 medium. After the red blood cells were lysed with ACK lysing buffer, the spleen cells were then mixed with murine myeloma P3 cells at ratio of 1 P3 cells:3 spleen cells. The mixture of spleen cells and P3 cells was washed and treated with pronase in fusion media (0.3M mannitol/D-sorbitol, 0.1 mM CaCl2, 0.5 mM MgCl2 and 1 mg/ml BSA) at room temperature for 3 min. The reaction was stopped by addition of FBS (Fetal Bovine Serum, Invitrogen); cells were then washed, resuspended in 2 ml cold fusion media and fused with BTX ECM 2001 electrofusion machine (Harvard Apparatus). The fused cells were added gently to RPMI-1640 selection medium containing hypoxanthine-aminopterin-thymidine (HAT) (Sigma Aldrich), incubated for 20 min at 37° C., and then seeded into flat bottom 96-well plates at 200 µl/well. The plates were then incubated in 5% $CO_2$ incubator at 37° C. until hydridoma clones were ready for antibody screening. Other techniques of immunization and hybridoma production can also be used, including those described in J. Langone and H. Vunakis (Eds., Methods in Enzymology, Vol. 121, "Immunochemical Techniques, Part I"; Academic Press, Florida) and E. Harlow and D. Lane ("Antibodies: A Laboratory Manual"; 1988; Cold Spring Harbor Laboratory Press, New York, N.Y.).

Hybridoma screening was done using flow cytometric binding assay with immunizing cells that are either untreated or treated with EGF (R&D Systems). Because incubation with EGF down-regulates EGFR level on the cell surface, EGFR specific hybridoma supernatant would only react to the untreated cells and not to the EGF-treated cells. Target cells for screening were first cultured in serum free media for overnight and separated into two parts. One part of the cells was left untreated and the other part was treated with EGF for 3 hours at 37° C. The EGF treated cells were labeled with CellTrace™ far red DDAO-SE (Invitrogen), mixed with untreated cells at 1:1 ratio and incubated with the hybridoma supernatant for 2 hours on ice. Cells were then washed, incubated with FITC-labeled anti mouse IgG (Jackson Immunoresearch), washed, fixed with formalin and analyzed using FACScalibur (BD Bioscience). The EGFR specific hybridomas were expanded and the supernatants were rescreened by ELISA using soluble recombinant human EGFR extracellular domain (RELIATech) as antigen. The positive hybridomas were rescreened using flow cytometric binding assay with human EGFR-expressing A431 epidermal carcinoma cell line (ATCC) and monkey EGFR-expressing Vero cell line (an African green monkey kidney epithelial cell line) (ATCC). In brief, the hybridoma supernatant was incubated with A431 cells and DDAO-labeled Vero cells on ice for 1 hour. The cells were washed twice and incubated with PE-conjugated goat anti-mouse IgG antibody (Jackson Immunoresearch) for 1 hour on ice. The cells were then washed with FACS buffer, fixed in formalin and analyzed using a FACSCalibur flow cytometer (BD Biosciences).

The positive hybridoma clones that reacted to both human and monkey antigens were tested for the capacity to inhibit basal proliferation of EGFR-overexpressing HCC827 cells (ATCC). In brief, exponentially growing HCC827 cells were plated at 2000 cells/well in 96 well plates in 100 µl complete media containing 10% FBS. 100 µl of hybridoma supernatant was added to the cells and the mixture was incubated at 37° C. in a humidified 5% $CO_2$ incubator for 5 days. Level of cell proliferation was determined using colorimetric WST-8 assay (Dojindo Molecular Technologies, Rockville, Md.). WST-8 is reduced by dehydrogenases in the living cells to an orange formazan product that is soluble in tissue culture medium, and the amount of formazan produced is directly proportional to the number of living cells. 10% of the final volume of WST-8 was added to each well and plates were incubated at 37° C. for an additional 2-4-h. Plates were then analyzed by measuring the absorbance at 450 nm (A450) in the Spectra Max M2 plate reader (Molecular Devices, Sunnyvale, Calif.). Background A450 absorbance of wells with media and WST-8 only was subtracted from all values. The surviving fraction was calculated by dividing each treated sample value by the average value of wells with untreated cell (surviving fraction=(A450 treated sample−A450 background)/(A450 untreated sample−A450 background)). The results were normalized so that surviving fraction 0 indicated the value of wells without cells and 1 indicated the level of cell proliferation in the serum containing media without any EGFR antibody. EGFR-8 hybridoma was selected for lack of capacity to inhibit HCC827 cell growth. They were subcloned by limiting dilution. One subclone which showed the same reactivity against EGFR as the parental cells by flow cytometry was chosen for subsequent analysis. Stable subclone was cultured and the antibody was isotyped using commercial isotyping reagents (Roche).

Antibody Purification

Antibodies were purified from hybridora subclone supernatants using standard methods, such as, for example Protein A or G chromatography (HiTrap Protein A or G HP, 1 mL, Amersham Biosciences). Briefly, supernatant was prepared for chromatography by the addition of 1/10 volume of 1M Tris/HCl buffer, pH 8.0. The pH-adjusted supernatant was filtered through a 0.22 µm filter membrane and loaded onto column equilibrated with binding buffer (PBS, pH 7.3). The column was washed with binding buffer until a stable baseline was obtained with no absorbance at 280 nm. Antibody was eluted with 0.1M acetic acid buffer containing 0.15M NaCl, pH 2.8, using a flow rate of 0.5 mL/min. Fractions of approximately 0.25 mL were collected and neutralized by the addition of 1/10 volume of 1M Tris/HCl, pH 8.0. The peak fraction(s) was dialyzed overnight twice against 1×PBS and sterilized by filtering through a 0.2 µm filter membrane. Purified antibody was quantified by absorbance at A280.

Protein A purified fractions were further polished using ion exchange chromatography (IEX) with quaternary ammonium (Q) chromatography for murine antibodies. Briefly, samples from protein A purification were buffer exchanged into binding buffer (10 mM Tris, 10 mM sodium chloride, pH 8.0) and filtered through 0.22 μm filer. The prepared sample was then loaded onto a Q fast flow resin (GE Lifesciences) that was equilibrated with binding buffer at a flow rate of 120 cm/hr. Column size was chosen to have sufficient capacity to bind all the MAb in the sample. The column was then washed with binding buffer until a stable baseline was obtained with no absorbance at 280 nm. Antibody was eluted by initiating a gradient from 10 mM to 500 mM sodium chloride in 20 column volume (CV). Peak fractions were collected based on absorbance measurement at 280 nm (A280). The percentage of monomer was assessed with size exclusion chromatography (SEC) on a TSK gel G3000SWXL, 7.8×300 mm with a SWXL guard column, 6.0×40 mm (Tosoh Bioscience, Montgomeryville, Pa.) using an Agilent HPLC 1100 system (Agilent, Santa Clara, Calif.). Fractions with monomer content above 95% were pooled, buffer exchanged to PBS (pH 7.4) using a TFF system, and sterilized by filtering through a 0.2 μm filter membrane. The IgG concentration of purified antibody was determined by A280 using an extinction coefficient of 1.47. Alternative methods such as ceramic hydroxyapatite (CHT) were also used to polish antibodies with good selectivity. Type II CHT resin with 40 μm particle size (Bio-Rad Laboratories) were used with a similar protocol as described for IEX chromatography. The binding buffer for CHT corresponds to 20 mM sodium phosphate, pH 7.0 and antibody was eluted with a gradient of 20-160 mM sodium phosphate over 20 CV.

Example 2

Binding Affinity to Human and Monkey EGFR Antigen

EGFR expressing human tumor cell lines such as MDA-MB468 (ATCC) and A431 cells (ATCC) and an African green monkey kidney cell line, called Vero (ATCC), were used in a flow cytometric binding assay to determine the binding affinity of the EGFR antibodies to the human and monkey antigens. In brief, the cells were incubated with various concentration of EGFR antibody for 1 h at 4° C. The cells were washed and incubated with PE-conjugated secondary antibody (Jackson Immunoresearch) for 1 h at 4° C. The cells were then washed, fixed in formalin and analyzed in FACSarray (BD Bioscience). To determine the binding affinity of these antibodies, geometric mean fluorescence intensity was plotted against the antibody concentration in a semi-log plot. A dose-response curve was generated by non-linear regression and the EC50 value of the curve, which corresponds to the apparent dissociation constant (Kd) of each antibody, was calculated using GraphPad Prism v4 (GraphPad software). The EGFR-8 antibody, ML66 antibody, cetuximab and panitumumab exhibited strong specific binding to both human tumor cell lines and Vero cells. A table shown in FIG. 1 lists the Kd of each antibody to the human and monkey EGFRs.

Example 3

Cloning and Sequencing of the VL and VH Regions of the ML66 Antibody

Total cellular RNA was prepared from $5 \times 10^6$ cells of the ML66 hybridoma using an RNeasy kit (QIAgen) according to the manufacturer's protocol. cDNA was subsequently synthesized from total RNA using the SuperScript II cDNA synthesis kit (Invitrogen).

The procedure for the first round degenerate PCR reaction on the cDNA derived from hybridoma cells was based on methods described in Wang et al. ((2000) *J Immunol Methods*. 233:167-77) and Co et al. ((1992) *J. Immunol*. 148:1149-54). VH sequences were amplified by PCR using the following degenerate primers: EcoMH1 CTTCCGGAATTCSARGTNMAGCTGSAGSAGTC (SEQ ID NO:41), EcoMH2 CTTCCGGAATTCSARGT-NMAGCTGSAGSAGTCWGG (SEQ ID NO:42) and BamIgG1 GGAGGATCCATAGACAGATGGGGGT-GTCGTTTTGGC (SEQ ID NO:43). VL sequences were amplified by PCR using the following degenerate primers: SacIMK GGAGCTCGAYATTGTGMTSACMCARCT-MCA (SEQ ID NO:44) and HindKL TATAGAGCT-CAAGCTTGGATGGTGGGAAGATGGATA-CAGTTGGTGC (SEQ ID NO:45). (Mixed bases are defined as follows: N=G+A+T+C, S=G+C, Y=C+T, M=A+C, R=A+G, W=A+T). The PCR reaction mixtures were then run on a 1% low melt agarose gel, the 300 to 400 bp bands were excised, purified using Zymo DNA mini columns, and sent to Agencourt Biosciences for sequencing. The respective 5' and 3' PCR primers were used as sequencing primers to generate the variable region cDNAs from both directions. The amino acid sequences of VH and VL regions were predicted from the DNA sequencing results.

Since the degenerate primers used to clone the VL and VH cDNA sequences alters the 5' end sequences, additional sequencing efforts were needed to verify the complete sequences. The preliminary cDNA sequences were used to search the NCBI IgBlast site (http://www.ncbi.nlm.nih.gov/igblast/) for the rat germline sequences from which the antibody sequences are derived. PCR primers were then designed to anneal to the germline linked leader sequence of the rat antibody so that this new PCR reaction would yield a complete variable region cDNA sequence, unaltered by the PCR primers. Alternatively, RACE procedures as described in Co et al., ((1992) *J. Immunol*. 148:1149-54) were also used to obtain 5' end sequences. The PCR reactions, band purifications, and sequencing were performed as described above.

Mass determination for sequence confirmation

The cDNA sequence information for the variable region was combined with the germline constant region sequence to obtain full length antibody cDNA sequences. The molecular weights of the heavy chain and light chain were then calculated and compared with the molecular weights obtained by LC/MS analyses of the rat ML66 antibody. The molecular weight measurements are consistent with the cDNA sequences for both the ML66 light and heavy chain.

Humanization of ML66 Antibody

The ML66 antibody was humanized following resurfacing methods previously described, such as, for example in Roguska et al., *Proc. Natl. Acad. Sci., USA*, 91(3): 969-973 (1994) and Roguska et al., *Protein Eng*. 9(10):895-904 (1996), which are incorporated in their entirety herein by reference. Resurfacing generally involves identification of the variable region framework surface residues in both the light and heavy chains and replacing them with human equivalents. The rodent CDR's are preserved in the resurfaced antibody. Exemplary CDRs of ML66 are defined as indicated in Table 10. In addition to the AbM heavy chain CDR2 definition employed for resurfacing, the table provides exemplary Kabat defined heavy chain CDR2's for both the rat and human versions of ML66. The underlined sequence marks the portion of the Kabat heavy chain CDR2 that was not considered a CDR for resurfacing.

TABLE 10

| Light Chain | |
|---|---|
| CDR1: | RASESVSTLMH |
| CDR2: | LASHRES |
| CDR3: | QQSRNDPWT |
| Heavy Chain | |
| CDR1: | ASNSVS |
| CDR2: | VIWNHGGTD |
| CDR3: | KGGIYFDY |
| Kabat ML66 HC CDR2 | |
| Rat HC CDR2: | VIWNHGGTD<u>YNSVIKS</u> |
| Humanized HC CDR2: | VIWNHGGTD<u>YNPSIKS</u> |

Surface residue positions were defined as any position with a relative accessibility of 30% or greater (Pedersen J. T. et. Al, *J. Mol. Biol.* 1994; 235: 959-973). The calculated surface residues were then aligned with human germline surface sequences to identify the most homologous human surface sequence. The human germline sequence used as the replacement surface for the light chain variable domain was IGKV7-3*01, and the human germline sequences used as the replacement surfaces for the heavy chain variable domain was IGHV4-39*02. The specific framework surface residue changes are given in FIG. 1. A total of six surface residues in the light chain and nine in the heavy chain were replaced with the human counterparts. FIG. 2 shows the alignment of the resurfaced sequences for ML66 variable domain of both light chain and heavy chain with their rat counterparts.

Recombinant Expression of Humanized ML66 (huML66 Antibody

The variable region sequences for huML66 were codon-optimized and synthesized by Blue Heron Biotechnology. The sequences are flanked by restriction enzyme sites for cloning in-frame with the respective constant sequences in single chain mammalian expression plasmids. The light chain variable region is cloned into EcoRI and BsiWI sites in the pAbKZeo plasmid. The heavy chain variable region is cloned into the HindIII and ApaI sites in the pAbG1Neo plasmid. These plasmids can be used to express the recombinant antibodies in either transient or stable mammalian cell transfections. Transient transfections to express recombinant antibodies in HEK 293T cells were performed using a modified PEI procedure (Durocher, Y. et al., *Nucleic Acids Res.* 30:E9 (2002)). Supernatant was purified by Protein A and polishing chromatography steps using standard procedures as described above.

Example 4

Binding Affinity of Humanized Antibodies

Binding affinity of the huML66 antibody was compared with the murine counterpart in a flow cytometric assay using MDA-MB468 cells. The binding assays were performed as described in Example 2 and the dose-response curves generated by non-linear regression for each antibody were shown in FIG. 4. The Kds calculated using GraphPad Prism v4 (GraphPad software, San Diego, Calif.) demonstrate that humanization did not affect the binding affinity of ML66 antibody. Anti-KTI (Kunitz Trypsin inhibitor) antibody (produced from hybridoma obtained from ATCC) was used as negative control.

Example 5

Inhibition of EGFR Ligand-Induced EGFR Activation

EGFR ligand binding induces EGFR phosphorylation followed by activation of downstream signaling pathways. To investigate the effect of anti-EGFR antibodies in ligand-induced EGFR activation, Western blot analysis was performed using MDA-MB468 tumor cell line and human primary adult keratinocytes. In brief, cells were seeded at $1 \times 10^6$ cells/well in a 6 well plate and cultured in normal media. Cells were washed and starved in serum/EGF free media containing 0.1% BSA for 2 hours at 37° C. 10 µg/ml antibody was added to the cells and the mixture was incubated for 3 hours at 37° C. 50 ng/ml EGF (R&D Systems) was added to the mixture and incubated for 15 minutes at 37° C. Cells were then washed with ice-cold PBS and lysed in RIPA buffer containing protease and phosphatase inhibitors. The protein lysates were separated in SDS-PAGE and transferred to a nitrocellulose membrane. The membrane was blocked with 5% BSA and incubated with anti-phosphotyrosine antibody (clone 4G10, Millipore) for overnight at 4° C. The membrane was washed, incubated with HRP-conjugated anti-mouse antibody (Jackson Immunoresearch) for 1 hour at room temperature, and washed again. The signal was detected using an ECL (enhanced chemiluminescene) system (GE Healthcare). To ensure equal amount of proteins loaded into each lane, the membrane was stripped and reprobed with anti (3-tubulin antibody (Sigma Aldrich).

As shown in FIG. 5, EGF stimulation led to a strong EGFR phosphorylation in both MDA-MB468 cells and human primary keratinocytes. Treatment of cells with cetuximab and panitumumab strongly inhibited the EGF-induced EGFR phosphorylation while the huML66 and muEGFR-8 antibodies had no effect on the EGFR activation. Anti-KTI antibody was used as negative control.

Example 6

Agonistic Activity of the EGFR Antibodies

Figure 6:
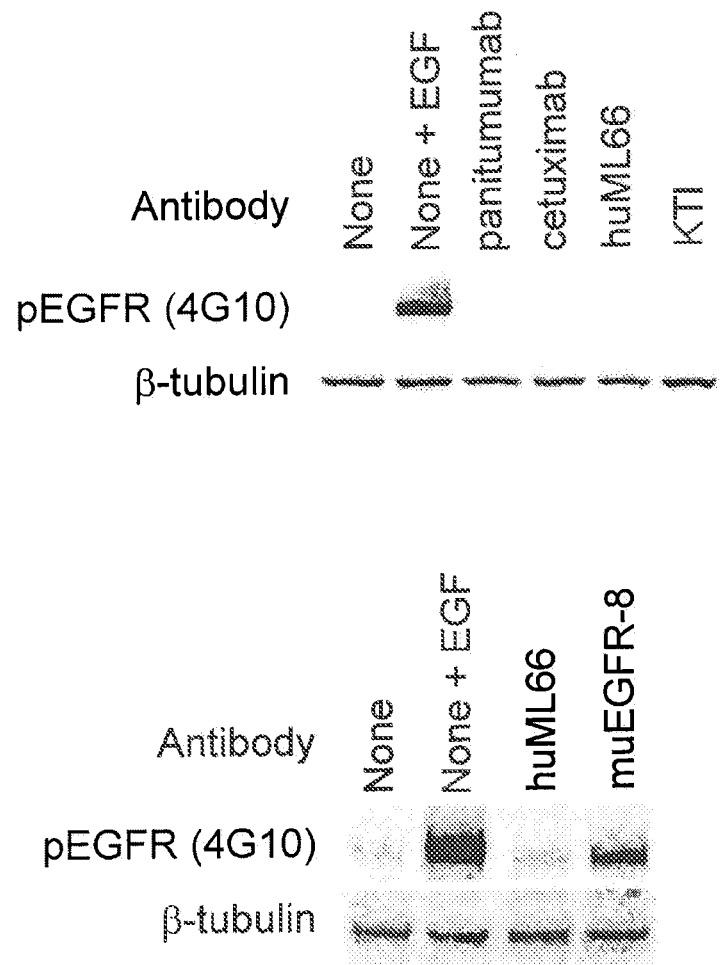
FIG. 6 shows a Western blot data depicting the effect of the indicated anti-EGFR antibodies on EGFR phosphorylation in MDA-MB468 cells in absence of exogenous EGFR ligand.

To investigate the effect of the EGFR antibodies of the invention on EGFR signaling in absence of EGFR ligands, MDA-MB468 tumor cells were starved in serum free media as described in Example 5. The cells were then incubated with 10 µg/ml EGFR antibodies for 3 hours at 37° C. As positive control, untreated cells were incubated with 50 ng/ml EGF for 15 minutes at 37° C. The protein lysates were prepared and analyzed using Western blot as described in Example 5. The representative result is shown in FIG. 6. EGF treatment clearly induced a strong EGFR phosphorylation in MDA-MB468 cells. Similarly, muEGFR-8 antibody also induced EGFR phosphorylation albeit the level of EGFR phosphorylation was lower than that of EGF. In contrast, panitumumab, cetuximab and huML66 antibody did not affect EGFR signaling in absence of the ligand. The results described in Example 5 and 6 show that EGFR-8 antibody is agonistic while ML-66 antibody does not affect the EGFR signaling.

Example 7

Ligand Binding Competition

Figure 7:
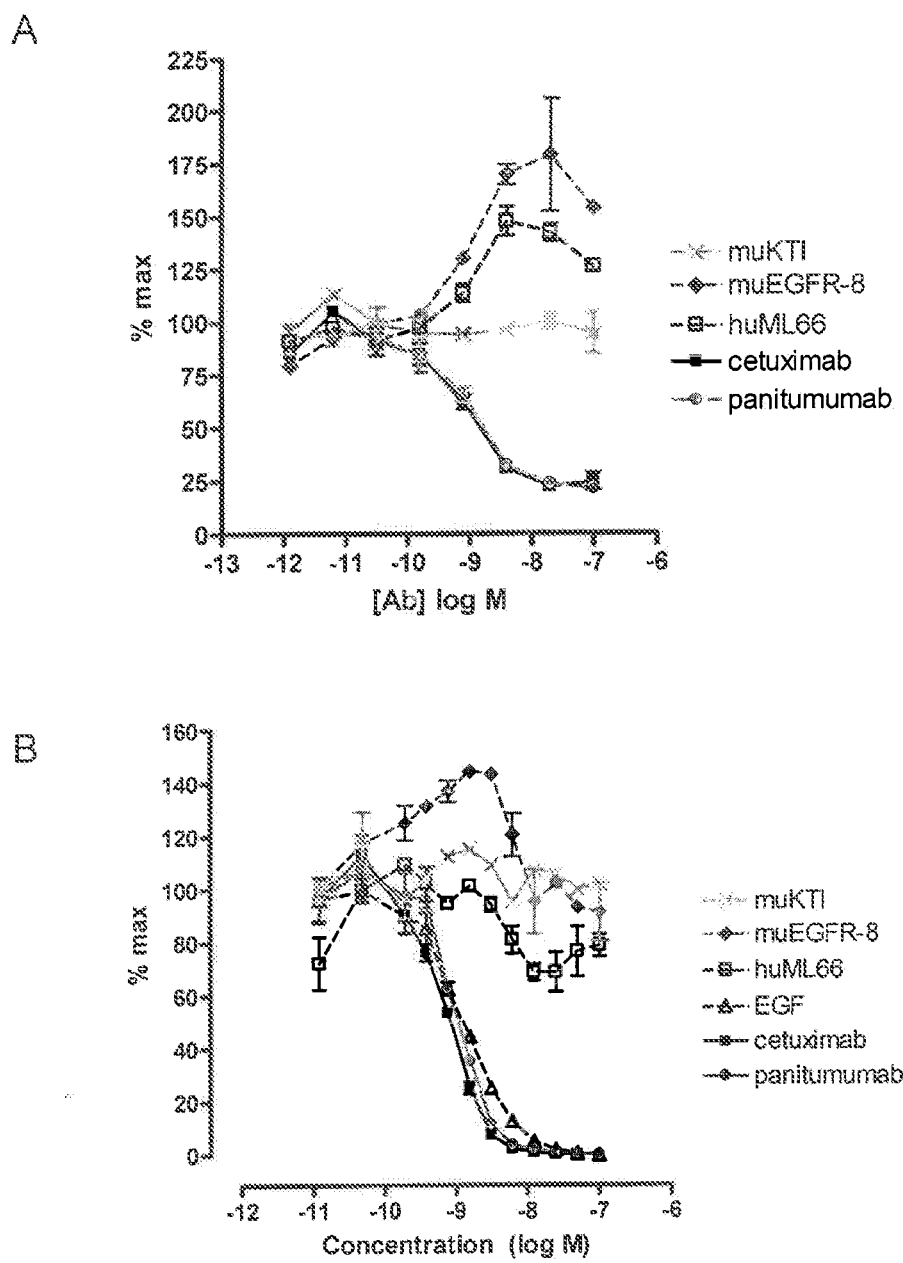
FIG. 7 shows line graphs depicting the binding of biotinylated TGFα (A) and EGF (B) ligand to tumor cells in presence of muEGFR-8 (diamonds) and huML66 (open squares).

One mechanism of EGFR signaling inhibition is blockade of ligand binding. To examine if the EGFR antibodies inhibit the ligand binding to the EGFR, the binding of biotinylated EGFR ligands to the MDA-MB468 cells was measured by flow cytometry in the presence of anti-EGFR antibodies. Biotinylation of TGFα (R&D system) was done using EZ-link Micro Sulfo-NHS-LC-biotinylation kit (Pierce, Rockland, Ill.) according to the manufacturer's instruction. Biotinylated EGF was purchased from Invitrogen. Prior to competition assay, the binding curve of the biotinylated ligands was established. Varying concentrations of anti EGFR antibodies were pre-mixed with biotinylated ligands at EC50 concentration (1.8 nM and 10 nM for EGF and TGFα, respectively), and the mixture was incubated with the cells for 30 min on ice. Cells were then washed twice with FACS buffer and incubated with streptavidin-APC conjugate (Jackson Immunoresearch) for 15 min on ice. Cells were washed twice with FACS buffer and analyzed in FACS Calibur (BD Bioscience) using FlowJo program (Tree Star). The geometric mean fluorescence intensities were plotted against the antibody concentration in a semi-log plot. As shown in FIG. 7, cetuximab and panitumumab both strongly inhibited the ligand binding while the negative control antibody, anti-KTI antibody did not have any effect. Intriguingly, huML66 antibody seemed to potentiate the TGFα binding (FIG. 7A) while it had minimal effect on the EGF binding (FIG. 7B) and muEGFR-8 antibody seemed to potentiate both TGFα and EGF binding.

Example 8

Growth Inhibition Assay of Human Primary Keratinocytes and Normal Epithelial Cell Line Human normal basal epithelial cells in skin, gastrointestinal tract and other organs physiologically express EGFR. The EGFR signaling in these tissues is critical for the epithelial cell growth. Disruption of EGFR function by cetuximab and panitumumab as well as small tyrosine kinase inhibitors such as erlotinib and gefitinib causes significant skin toxicity. To mimic the potential toxicity in skin and other epithelial cells, proliferation assay using human primary keratinocytes (Invitrogen) and a non-tumorigenic breast epithelial cell line, MCF100A (ATCC), was established. In this assay, cells were plated at 1,500-2,000 cells per well in EGFR ligand-containing media suggested by the manufacturers and incubated with anti-EGFR antibodies at 37° C. for 5 days. In the keratinocytes assay (FIG. 8), cells were grown in 0.2 ng/mt EGF with varying concentration of antibodies. While in MCF10A cell assay (FIG. 9), cells were incubated with varying concentration of EGFR ligands and fixed concentration (10 μg/ml) of antibodies. Level of cell proliferation was determined using colorimetric WST-8 assay (Dojindo Molecular Technologies, Rockville, Md.). WST-8 is reduced by dehydrogenases in the living cells to an orange formazan product that is soluble in tissue culture medium, and the amount of formazan produced is directly proportional to the number of living cells. 10% of the final volume of WST-8 was added to each well and plates were incubated at 37° C. in a humidified 5% $CO_2$ incubator for an additional 2-4-h. Plates were then analyzed by measuring the absorbance at 450 nm (A450) in the Spectra Max M2 plate reader (Molecular Devices, Sunnyvale, Calif.). Background A450 absorbance of wells with media and WST-8 only was subtracted from all values. The surviving fraction was calculated by dividing each treated sample value by the average value of wells with untreated cell (surviving fraction=(A450 treated sample−A450 background)/(A450 untreated sample−A450 background)). The results were normalized so that 0 indicated the level of cell proliferation in absence of EGF and 1 indicated the level of cell proliferation in presence of EGF without any anti-EGFR antibody treatment.

Figure 8:
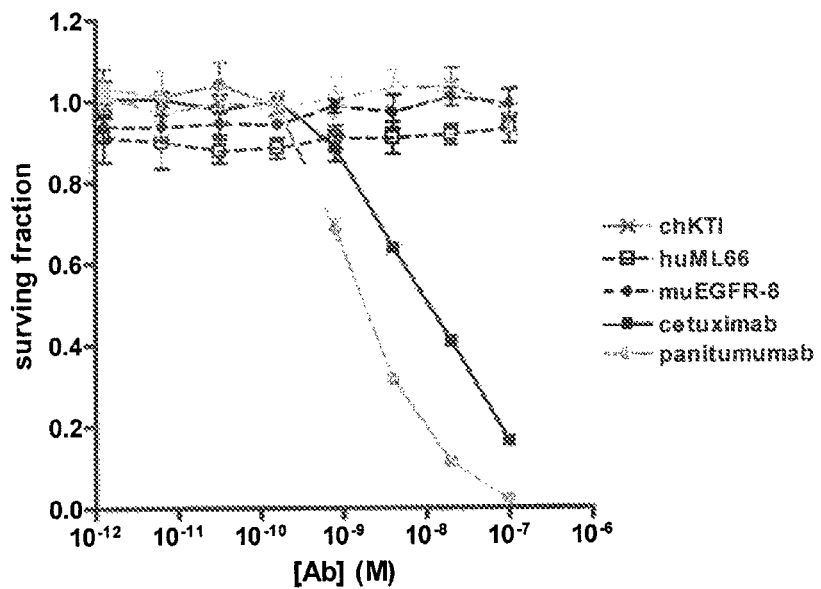
FIG. 8 depicts a line graph depicting the capacity of muEGFR-8 (diamonds) and huML66 (open squares) in inhibiting the growth of human primary keratinocytes.
Figure 9:
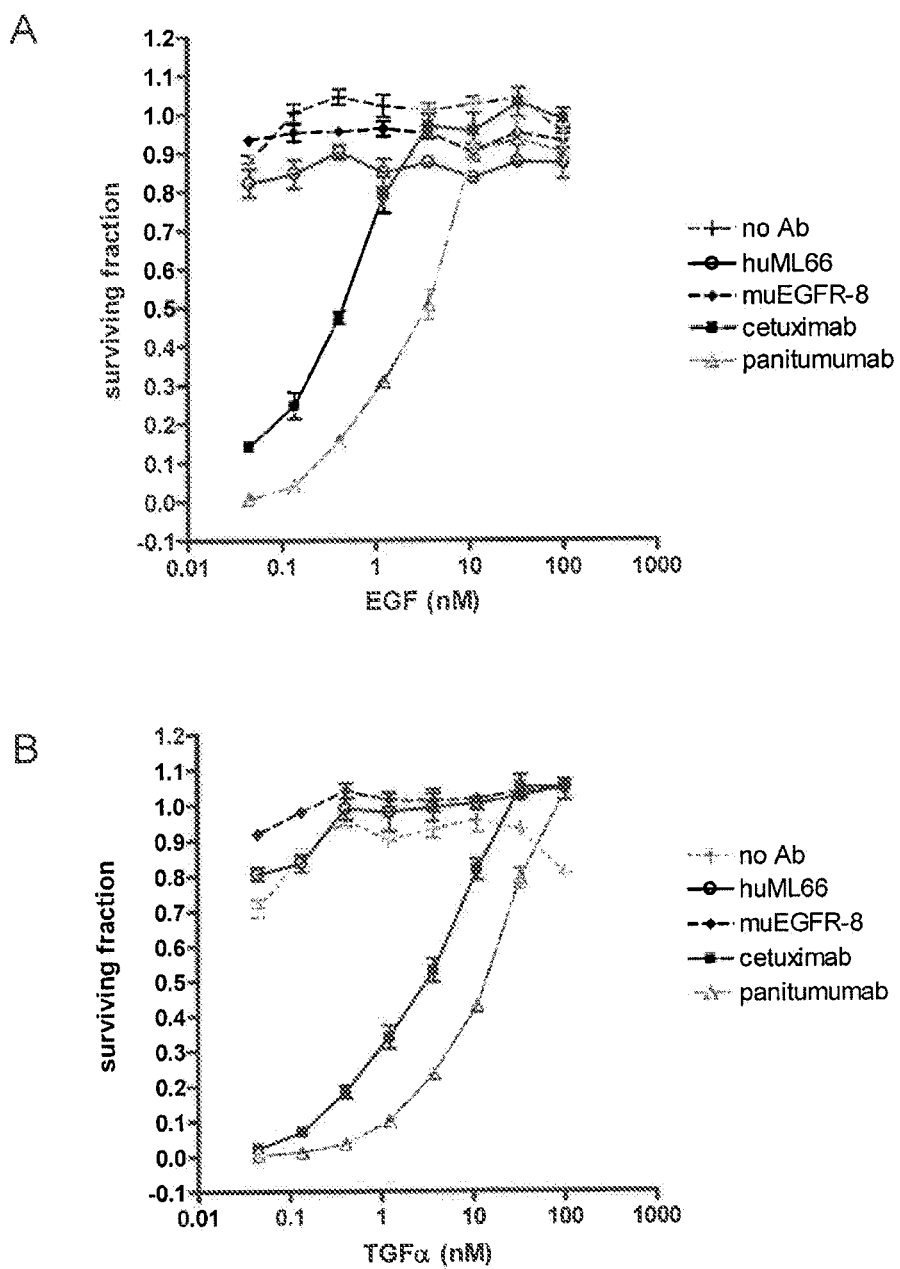
FIG. 9 shows line graphs depicting the capacity of muEGFR-8 (diamonds) and huML66 (open circles) in inhibiting MCF10A cell growth stimulated by the indicated concentration of EGF (A) or TGF☐ (B).

The binding of the anti-EGFR antibodies to human primary keratinocytes as well as MCF10A cells was confirmed before the proliferation assays were performed. A representative result of the keratinocytes proliferation assay is shown in FIG. 8. As expected from the toxicity profile, cetuximab and panitumumab strongly inhibited the keratinocytes proliferation in dose dependent manner while the huML66 and muEGFR-8 antibodies, similar as the negative control chimeric KTI antibody, had little or no effect on the keratinocytes. Similarly, as shown in FIG. 9, cetuximab and panitumumab strongly inhibited MCF10A cell proliferation while the huML66 and muEGFR-8 antibodies had little or no effect on the normal epithelial cell growth. These data suggest that ML66 and EGFR-8 antibody are less toxic than cetuximab and panitumumab on normal epithelial cells.

Example 9

Inhibition of basal proliferation of NCI-H292 and NCI-H322M cell lines

To determine the capacity of anti-EGFR antibodies in inhibiting the basal level proliferation of tumor cells, proliferation assays with EGFR expressing NCI-H292 (ATCC) and NCI-H322M (NCI) lung tumor cell lines were established. Cells were plated at 2,000 cells per well in normal growth media containing 10% FBS and grown at 37° C. for 5 days in presence of varying concentration of anti-EGFR antibodies. Level of cell proliferation was determined using colorimetric WST-8 assay as described in example 8. The OD results were normalized so that surviving fraction 1 represents cells grown in normal growth media without anti-EGFR antibodies, and 0 represents the wells without any cells.

Figure 10:
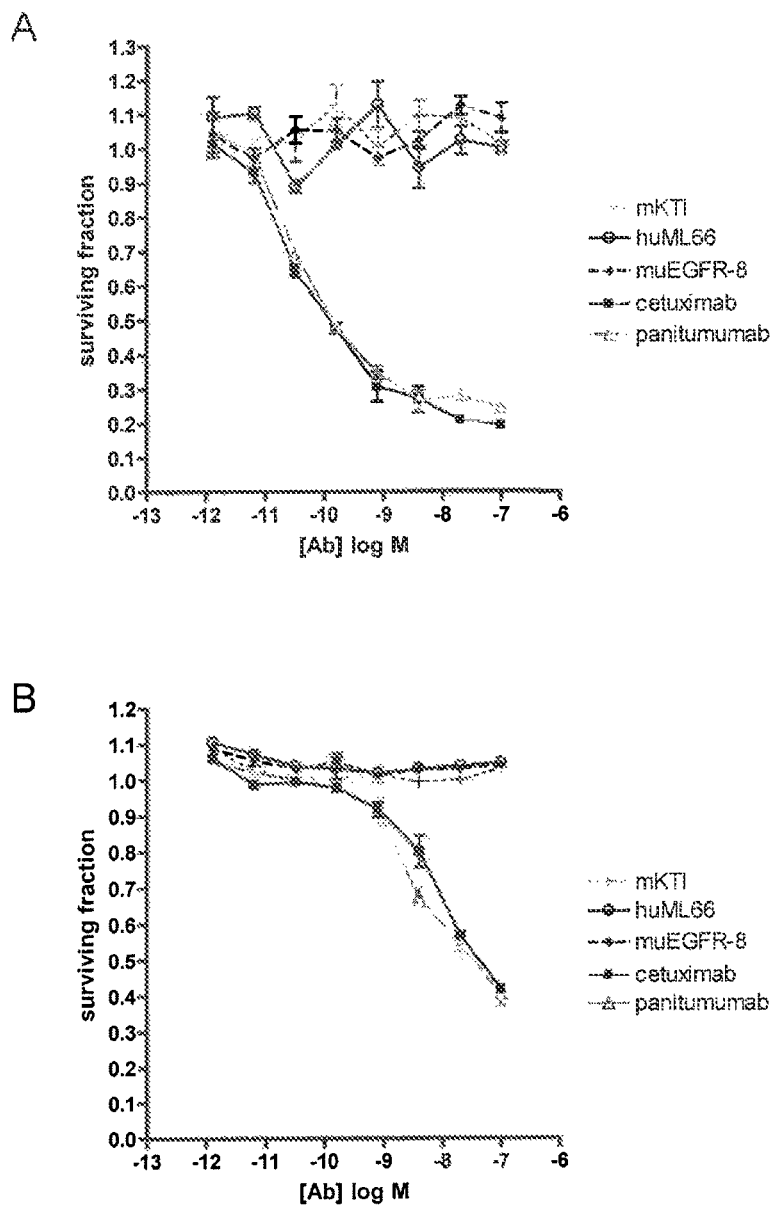
FIG. 10 shows line graphs depicting the capacity of muEGFR-8 (diamonds) and huML66 (open circles) in inhibiting the basal cell growth of NCI-H292 (A) and NCI-H322M (B) cell lines.

FIGS. 10A and B show the proliferation assay results with NCI-H292 and NCI-H322M cells, respectively. Cetuximab and panitumumab treatment inhibited the proliferation of both cell lines in dose dependent manner. In contrast, huML66 and muEGFR-8 antibodies did not affect the tumor cell growth.

Example 10

Anti-EGFR Antibody Binding Competition

Figure 11:
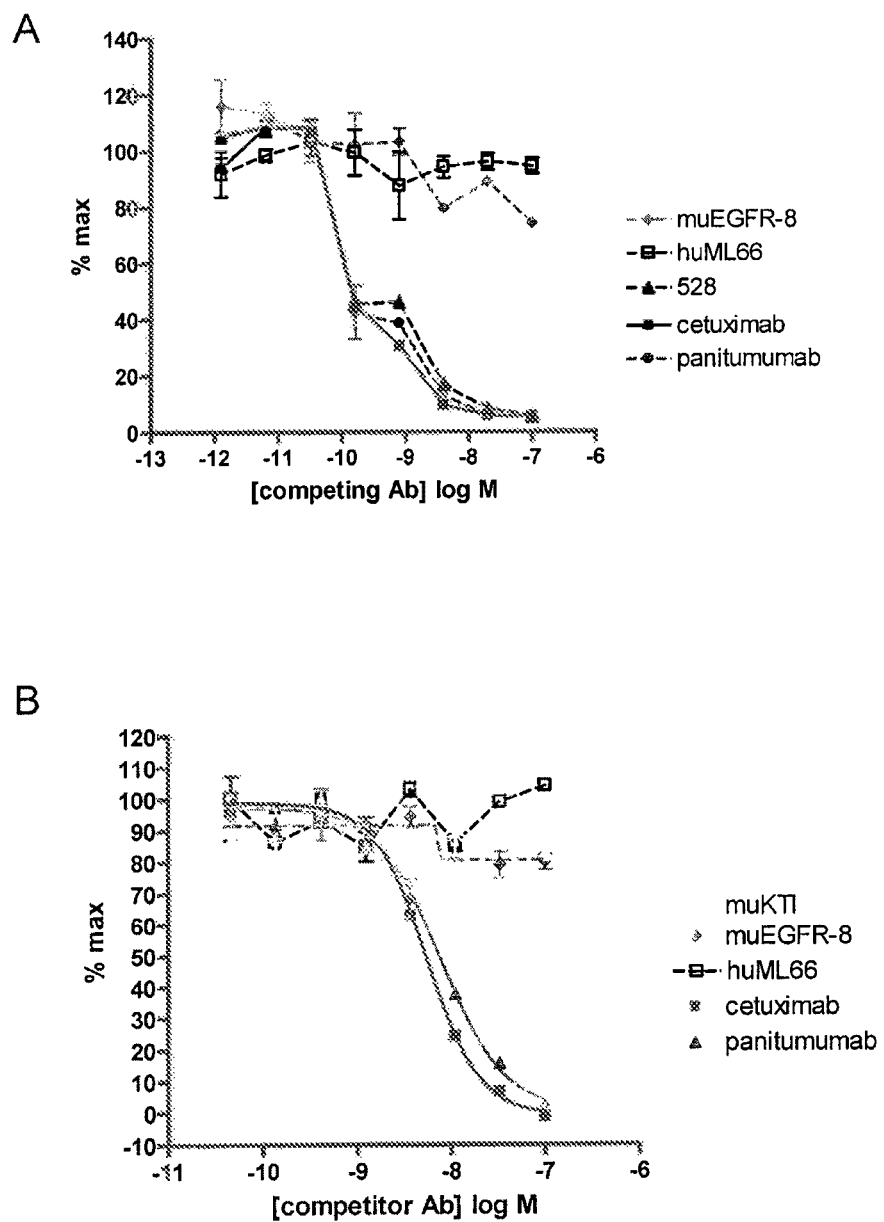
FIG. 11 shows line graphs depicting the binding of biotinylated 528 antibody (A) and cetuximab (B) to the MDA-MB468 cells in presence of muEGFR-8 (diamonds) and huML66 (open squares) at the indicated concentration.

To distinguish binding epitopes of anti-EGFR antibodies, antibody binding competition assays were performed using flow cytometry. In this experiment, binding of biotinylated 528 antibody (produced from 528 hybridoma obtained from ATCC) and cetuximab to the MDA-MB468 cells was measured in presence of varying concentration of 'competing' antibodies. The 528 antibody and cetuximab were first labeled with biotin as described in Example 8. 0.2 nM biotinylated 528 antibody or cetuximab was pre-mixed with varying concentration of panitumumab, cetuximab, 528, muEGFR-8, huML66 and KTI antibody. The antibody mixture was incubated with the target A431 cells on ice for 2 h. The cells were washed and incubated with streptavidin-alexa 488 conjugate on ice for 1 h. After washing, the cells were fixed and analyzed in FACS calibur. The geometric mean fluorescence intensity was plotted against antibody concentration in semi-log plot and normalized so that 100% represents the maximal binding of the biotinylated reference antibody in absence of the competitor antibody and 0% represents the background staining in absence of the biotinylated antibody. FIG. 11A and B show representative binding result of biotinylated 528 antibody and cetuximab, respectively, in presence of the competitor antibodies. The data in FIG. 11 show that 528, cetuximab and panitumumab compete with one another while the huML66 and muEGFR-8 antibodies do not compete with both cetuximab and 528 antibodies, suggesting the antibodies of the invention bind to epitope(s) distinct from those of cetuximab and 528 antibodies.

Example 11

ADCC Activity of huEGFR Antibodies

A lactate dehydrogenase (LDH) release assay was used to measure antibody-dependent cell mediated cytotoxicity (ADCC) of tumor cells lines using freshly isolated human natural killer (NK) cells as effector cells (Shields R L, *J Biol. Chem.* 2001 276(9):6591-604). The NK cells were first isolated from human peripheral blood from a normal donor (Research Blood Components, Inc., Brighton, Mass.) using a modified protocol for the NK cell Isolation Kit II (#130-091-152; Miltenyi Biotec, Auburn, Calif.). Peripheral blood was diluted 2-fold with 1×PBS. 25 mL of diluted blood was carefully layered over 25 mL of Ficoll Paque in a 50 mL conical tube and centrifuged at 400 g for 45 min at RT. The peripheral blood mononuclear cells (PBMC) were collected from the interface, transferred into a new conical 50 mL tube, and washed once with 1×PBS. The PBMC were counted and resuspended at concentration of $2.5 \times 10^7$ cells/100 µl with MACS buffer (1×PBS, 0.5% BSA, 2 mM EDTA), and then ¼× volume of NK cell Biotin-Antibody Cocktail were added to the cell suspension. The NK cell Biotin-Antibody Cocktail contains biotinylated antibodies that bind to the lymphocytes, except for NK cells, resulting in a negative selection of NK cells. The mixture was incubated at 4° C. for 10 min, and then ⅗× volume of MACS buffer and ⅖× volume of NK cell MicroBead cocktail that would bind to the biotinylated antibodies were added. The cell-antibody mixture was incubated for another 15 min at 4° C. Next, cells were washed once with 50 mL of MACS buffer and resuspended in 3 mL of MACS buffer. NK cells were separated as negative fraction using autoMACS separator (Miltenyi Biotec). The resulting NK cells were plated into 30 mL of complete RPMI media (RPMI-1640 supplemented with 5% fetal bovine serum, 1% penicillin-streptomycin, 1 mM HEPES, 1 mM Sodium Pyruvate, 1% 100×MEM non-essential Amino Acid Solution) overnight. The subsequent assay and all dilutions were carried out in RHBP medium (RPMI-1640 medium supplemented with 20 mM HEPES, pH 7.4, 0.1% BSA and 1% penicillin-streptomycin).

Various concentrations of antibodies in RHBP medium were aliquoted in duplicate at 50 µL/well into a round bottom 96-well plate. The target cells (in this experiment A431 cell line) were resuspended at $10^6$ cells/mL in RHBP medium and added at 100 µL/well to each well containing antibody dilutions. The plate containing target cells and antibody dilutions was incubated for 30 min at RT. NK cells were then added to the wells containing the target cells at 50 µL/well. The typical ratio was 1 target cell to 3-4 NK cells. The following controls were set up for each experiment: NK cells alone, target cells alone (spontaneous LDH release), target cells with NK cells (antibody independent LDH release), target cells with 10% Triton X-100 (maximum LDH release). The mixtures were incubated at 37° C. for 4 h to allow for cell lysis. Plates were centrifuged for 10 min at 1200 rpm, and 100 µL of the supernatant was carefully transferred to a new flat-bottom 96-well plate. LDH reaction mixture (100 µL/well) from the Cytotoxicity Detection Kit (Roche 1 644 793) was added to each well and incubated at room temperature for 5 to 30 min. The optical density (OD) of samples was measured at 490 nm (OD490). The percent specific lysis of each sample was determined using the following formula: percent specific lysis= (sample value−spontaneous release)/(maximum release− spontaneous release)*100.

Figure 12:
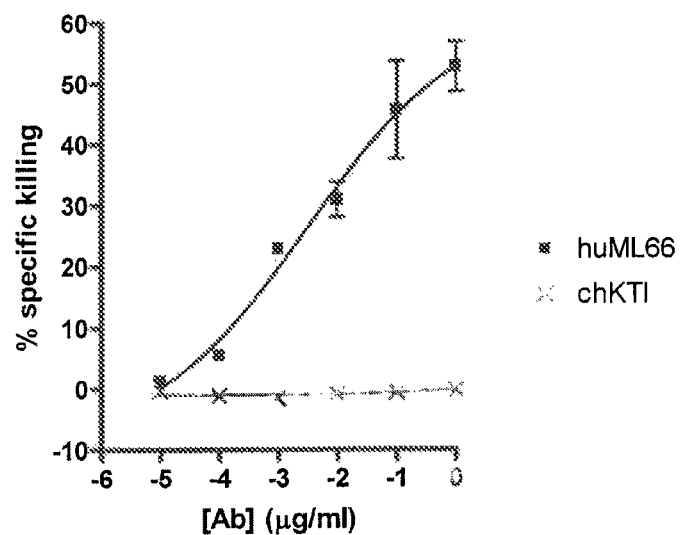
FIG. 12 shows a line graph depicting NK cell mediated % specific killing in presence of huML66 and chKTI antibodies at the indicated concentration.

FIG. 12 shows a representive ADCC activity of huML66 antibody in comparison to that of chKTI antibody. The huML66 antibody induced NK cell mediated killing of target cells in dose dependent manner with maximal specific killing reached more than 50%. In contrast, chKTI antibody that did not bind to target cells failed to mediate ADCC.

Example 12

Preparation of huML66-SMCC-DM1

The (Succinimidyl 4-(N-maleimidomethyl)cyclohexane-1-carboxylate (SMCC, Pierce Biotechnology, Inc) linker was dissolved in dimethylacetamide (DMA). The huEGFR antibody was modified with SMCC to introduce maleimides into the antibody by incubating the antibody at 5 mg/mL in 50 mM potassium phosphate, 50 mM NaCl, 2 mM EDTA, pH 6.5 with a 10 molar excess of SMCC. After approximately 100 minutes at ambient temperature, the reaction mixture was purified using a SEPHADEX™ G25 column equilibrated with the same potassium phosphate buffer. Antibody containing fractions were pooled and used for subsequent steps.

The SMCC-modified antibody was reacted with a 10 mM solution of DM1 at a 1.7 molar excess relative to the maleimide linker. The reaction was stirred at ambient temperature under for approximately 18 hours. The conjugation reaction mixture was filtered through a SEPHADEX™ G25 gel filtration column equilibrated with xPBS at pH 6.5. The huEGFR antibody-SMCC-DM1 conjugate was then dialyzed into buffer containing 10 mM histidine, 250 mM glycine, 1% sucrose pH 5.5. The number of DM1 molecules linked per antibody molecule was determined using the previously reported extinction coefficients for antibody and DM1 (Liu et al., *Proc. Natl. Acad. Sci. USA,* 93, 8618-8623 (1996)). The percentage of free maytansinoid present after the conjugation reaction was determined by injecting 20-50 µg conjugate onto a HiSep column equilibrated in 25% acetonitrile in 100 mM ammonium acetate buffer, pH 7.0, and eluting in acetonitrile. The peak area of total free maytansinoid species (eluted in the gradient and identified by comparison of elution time with known standards) was measured using an absorbance detector set to a wavelength of 252 nm and compared with the peak area related to bound maytansinoid (eluted in the conjugate peak in the column flow-through fractions) to calculate the percentage of total free maytansinoid species. Conjugates with 3.5-4 DM1 molecules per huEGFR antibody were obtained with <1% present as unconjugated maytansinoid.

Preparation of huML66-SPDB-DM4

The exemplary N-succinimidyl 4-(2-pyridyldithio) butanoate (SPDB) linker was dissolved in ethanol. The huEGFR antibody was incubated at 8 mg/mL with a 5.5-5 fold molar excess of SPDB linker for approximately 2 hours at room temperature in 50 mM potassium phosphate buffer (pH 6.5) containing 50 mM NaCl, 2 mM EDTA, and 3% ethanol. The SPDB modified antibody was diluted 2-fold in PBS, pH 6.5 and modified with a 1.5 fold molar excess of the maytansinoid DM4 by the addition of a concentrated solution (15-30 mM) of DM4 in dimethylacetamide (DMA). After overnight incubation at room temperature, the conjugated antibody was purified by chromatography on SEPHADEX™ G25F equilibrated with 10 mM histidine, 250 mM glycine, 1% sucrose pH 5.5. The number of DM4 molecules linked per antibody molecule was determined using the previously reported extinction coefficients for antibody and maytansinoid (Widdison W C et al. J Med Chem, 49:4392-4408 (2006)). The percentage of total free maytansinoid species were determined as described above. Conjugates with 3.5-4 DM4 molecules per huEGFR antibody were obtained with <1% present as unconjugated maytansinoid.

Example 13

Binding Affinity of Maytansinoid Conjugates

Binding affinity of the huML66 and muEGFR-8 antibody maytansinoid conjugates was compared with that of the naked antibodies using MDA-MB468 cells or A431 cells as described in the Example 2. The Kds calculated from binding curve of the huML66 antibody and conjugates (FIG. 13A) were 1.12 nM for naked huML66 antibody, 2.33 nM for huML66-SMCC-DM1 conjugate, and 2.93 nM for huML66-SPDB-DM4 conjugate. The Kds calculated from binding curve of the muEGFR-8 antibody and conjugates (FIG. 13B) were 1.43 nM for naked muEGFR-8 antibody and 4.54 nM for muEGFR-8-SMCC-DM1 conjugate. This data demonstrates that DM conjugation does not notably alter the binding affinity of the huML66 and muEGFR-8 antibody to the huEGFR.

Example 14

In Vitro Cytotoxicity Assays

The ability of EGFR antibody maytansinoid conjugates to inhibit tumor cell growth was measured using in vitro cytotoxicity assays. Briefly, target cells were plated at 1,500 to 3,000 cells per well in 100 µL complete RPMI media containing 10% FBS. Conjugates were diluted into complete RPMI media using 5-fold dilution series and 100 µL were added per well. The final concentration typically ranged from $3 \times 10^{-8}$ M to $8 \times 10^{-14}$ M. Cells were incubated at 37° C. in a humidified 5% $CO_2$ incubator for 5 days. Viability of the remaining cells was determined by colorimetric WST-8 assay and the absorbance at 450 nm (A450) was measured in a multiwell plate reader. The surviving fraction was calculated by dividing each treated sample value by the average value of untreated controls. The surviving fraction value was plotted against the antibody-conjugate concentration in a semi-log plot for each treatment.

Figure 13:
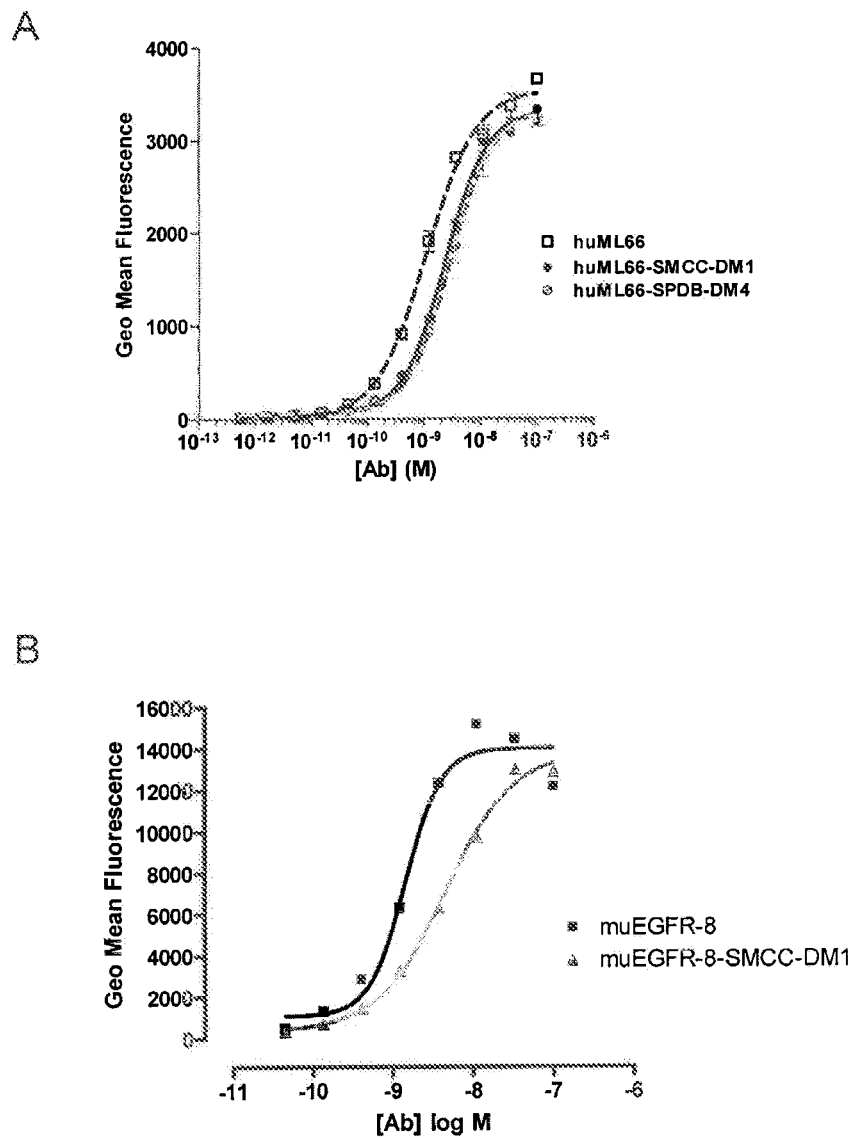
FIG. 13 depicts binding curves of the huML66 (A) and muEGFR-8 (B) naked antibodies and their corresponding DMx conjugates.
Figure 14:
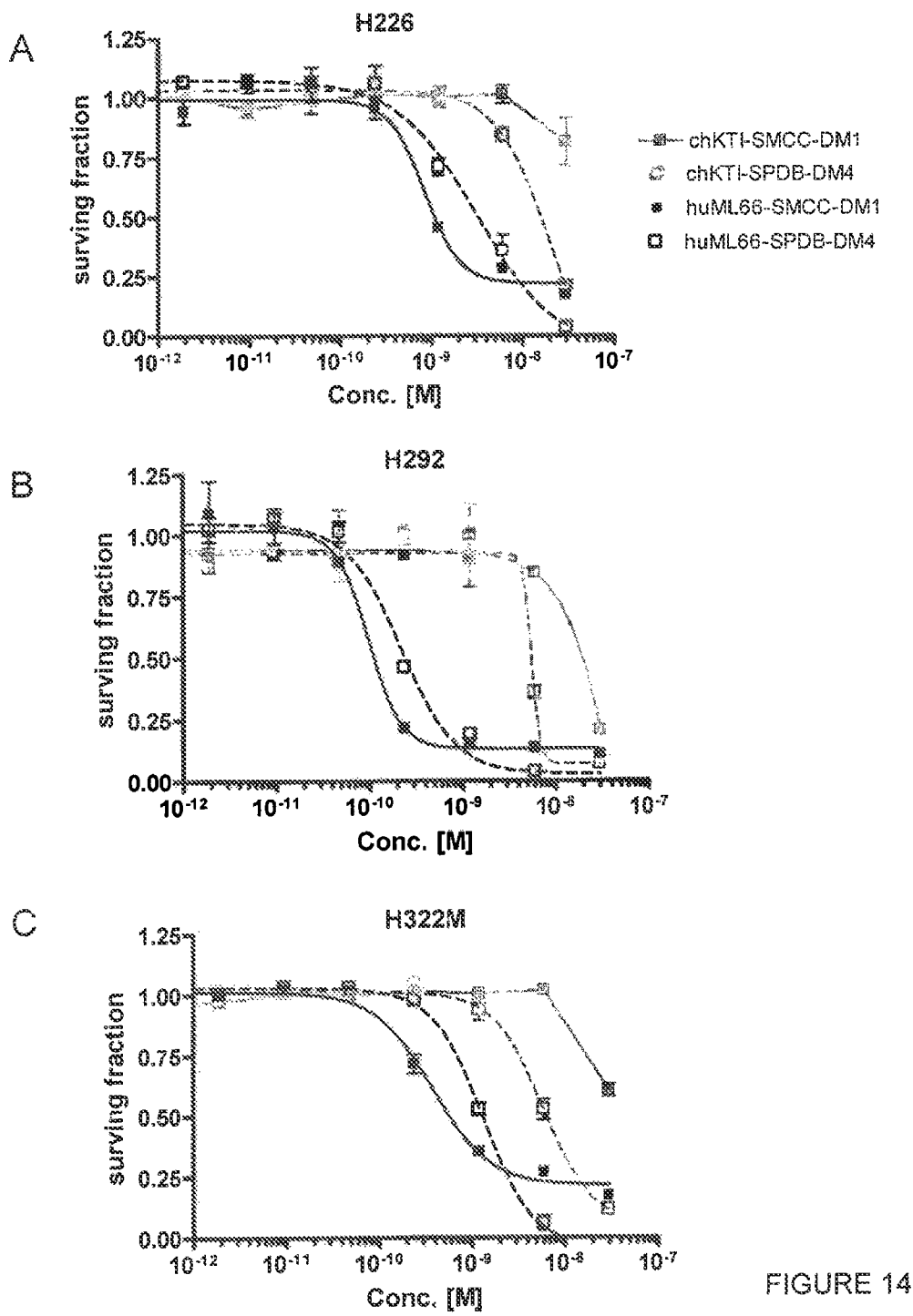
FIG. 14 shows line graphs depicting the cytotoxic activity of ML66-SMCC-DM1 and ML66-SPDB-DM4 conjugates in NCI-H226 (A), NCI-H292 (B) and NCI-H322M (C) cell lines.

In FIG. 14, the in vitro cytotoxicity of huML66-SMCC-DM1 and huML66-SPDB-DM4 conjugates was compared to the activity of a non-specific maytansinoid conjugates such as chKTI-SMCC-DM1 and chKTI-SPDB-DM4 conjugates. The results from a typical cytotoxicity assay are shown in FIGS. 13A, B and C for NCI-H226 (ATCC), NCI-H292 (ATCC) and NCI-H322M cells (NCI), respectively. The huML66 Ab conjugates exhibited strong and specific cytotoxicity in the three EGFR-expressing tumor cell lines with EC50 ranging from 3 nM to 0.1 nM.

Figure 15:
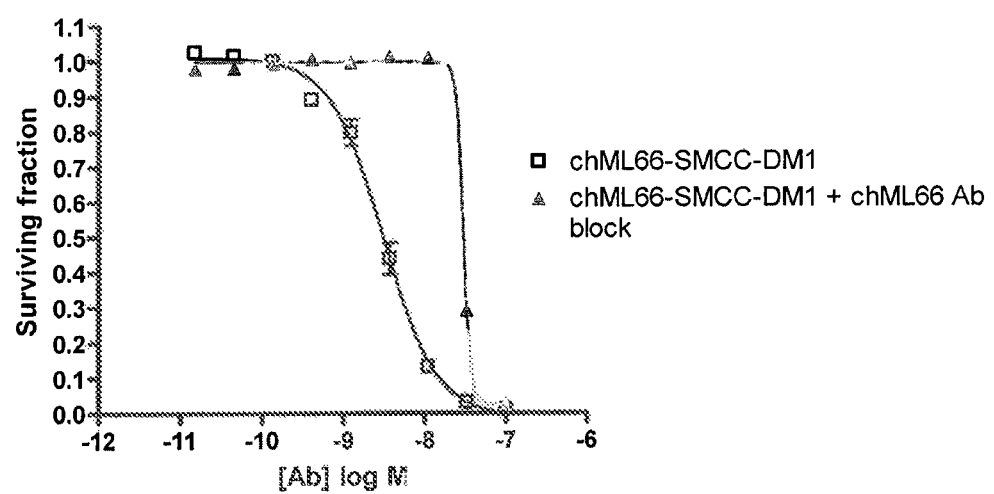
FIG. 15 shows line graphs depicting the cytotoxic activity of ML66-SMCC-DM1 in KB cell lines in presence or absence of excess ML66 blocking antibody.

In FIG. 15, the specific toxicity of chimeric ML66-SMCC-DM1 (chML66-SMCC-DM1) was tested in KB cell line. In this experiment, the target cells were incubated with chML66 conjugate with or without excess of naked chML66 antibody (1 µM). The naked chML66 antibody blocked the binding of ML66 conjugate thus inhibited the specific cytotoxicity of the conjugate. The EC50s are 30 nM and 3 nM for ML66-SMCC-DM1 with and without naked ML66 antibody blocking, respectively. Therefore, there is one log specificity window with the ML66 conjugate.

Figure 16:
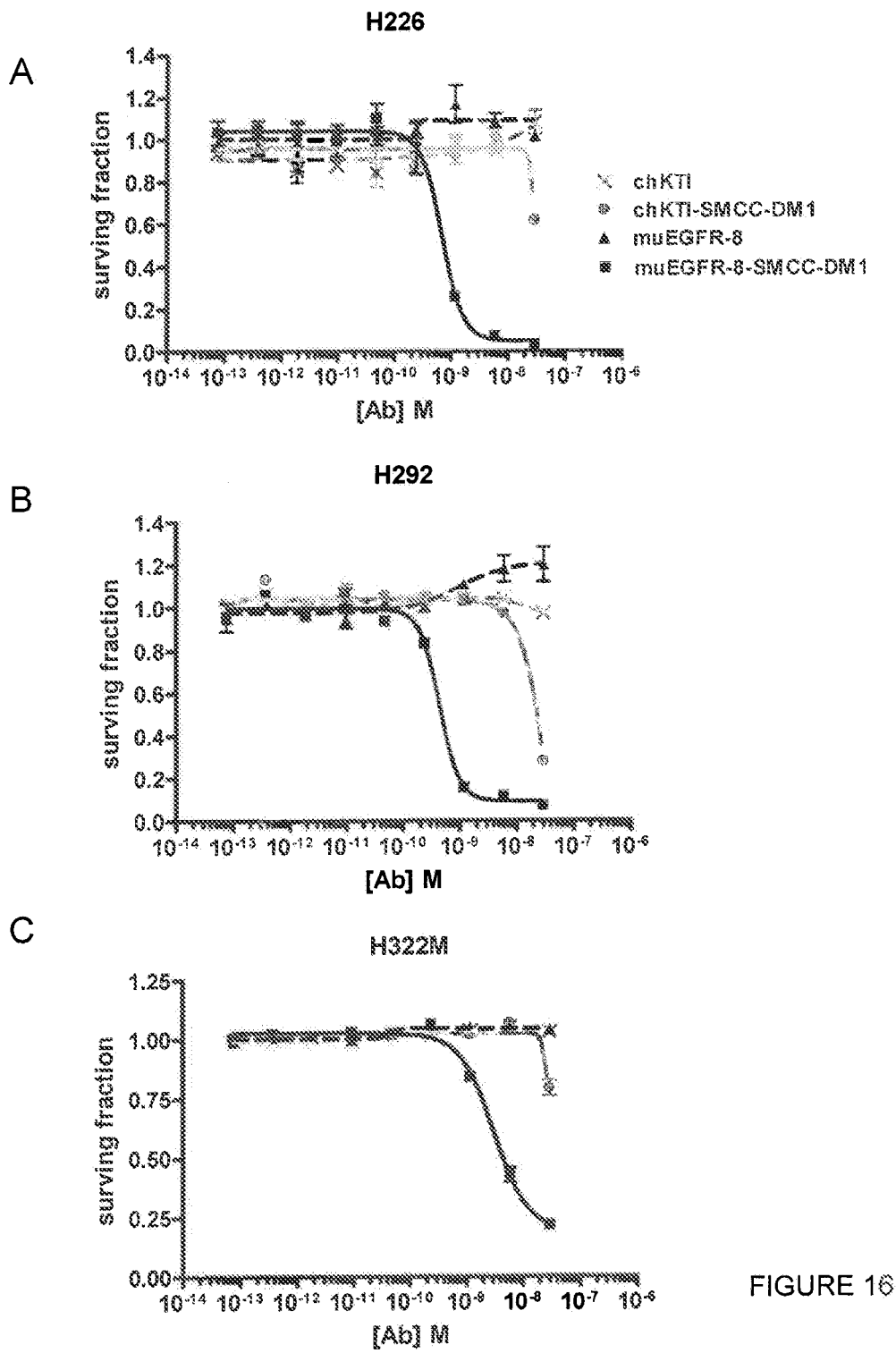
FIG. 16 shows line graphs depicting the cytotoxic activity of muEGFR-8-SMCC-DM1 conjugate in NCI-H226 (A), NCI-H292 (B) and NCI-H322M (C) cell lines.

In FIG. 16, the in vitro cytotoxicity of muEGFR-8-SMCC-DM 1 was compared to the activity of a non-specific chKTI-SMCC-DM1 conjugate. The results from a typical cytotoxicity assay are shown in FIGS. 16A, B and C for NCI-H226 (ATCC), NCI-H292 (ATCC) and NCI-H322M cells (NCI), respectively. The muEGFR-8-SMCC-DM1 conjugate showed a strong and specific cytotoxicity in the three EGFR-expressing tumor cell lines with EC50 of 0.68 nM, 0.43 nM and 3.07 nM in NCI-H226, NCI-H292 and NCI-H322M respectively. In contrast, chKTI-SMCC-DM1 had little effect and the naked muEGFR-8 antibody did not show any toxicity in all three cell lines. These data suggest that DMx conjugation makes non-antagonistic EGFR antibodies of the invention to become highly cytotoxic.

Example 15

Figure 17:
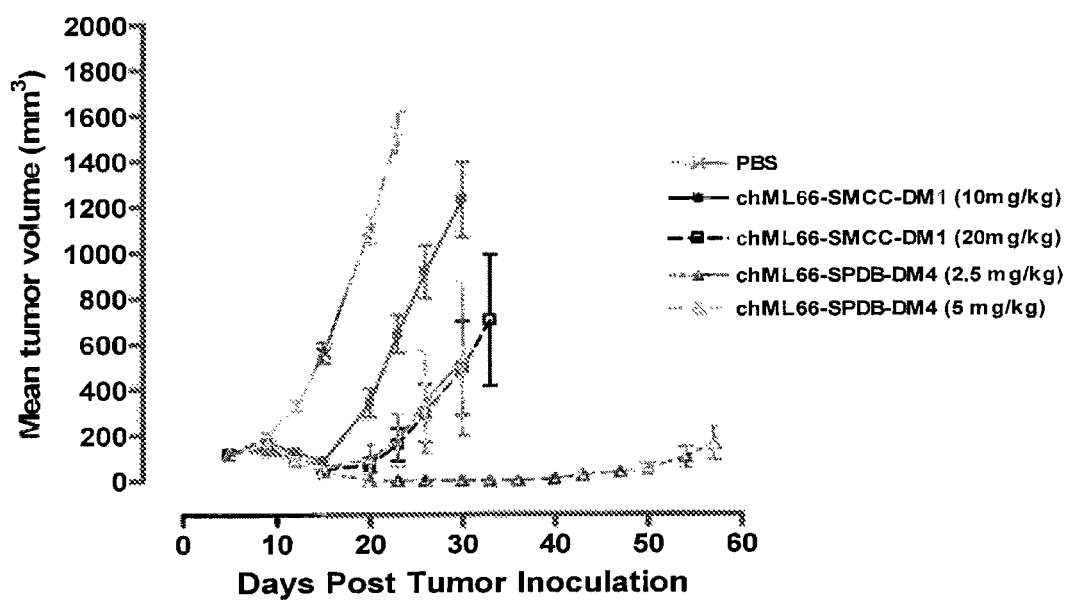
FIG. 17 shows line graphs depicting growth of KB tumor xenograft in mice treated with the indicated maytansinoid conjugates.

In Vivo Efficacy Study of chML66 Antibody Maytansinoid Conjugates in KB Tumor Model The activity chML66-antibody-maytansinoid conjugates was tested in an established tumor xenograft model using EGFR expressing KB cells implanted subcutaneously in SCID mice. Animals were randomized by tumor volume into treatment groups when tumors reached a mean tumor volume of approximately 115 $mm^3$ and injected once with 20 or 10 mg/kg of chML66-SMCC-DM1 conjugate or 5 or 2.5 mg/kg chML66-SPDB-DM4 conjugate. The mean tumor volume of each treatment groups is plotted against time post tumor cell inoculation in FIG. 17. It is apparent that treatment with chML66-DM conjugates significantly delays the tumor growth. In particular, treatment of chML66-SPDB-DM4 at 5 mg/kg dose resulted in 3 out of 6 mice tumor free and all 6 mice experienced complete response (no palpable tumor detected). The lower dose of chML66-SPDB-DM4 also resulted in complete response in 4 out of 6 mice. None of the mice treated with chML66-SMCC-DM1 experienced complete response, however the conjugate treatment significantly inhibited tumor growth. Percent of tumor growth inhibition (% T/C) corresponds to the median of tumor volume of each treated group divided by the median tumor volume of control group when the tumor volume of the control group reaches a predetermined size. A treatment with a % T/C value of below 42% is considered active, while a treatment with a % T/C value of below 12% is considered highly active. The % T/C value on day 20 post cell inoculation corresponded to 23%, 6%, 0% or 0% for 10 mg/kg chML66-SMCC-DM1, 20 mg/kg chML66-SMCC-DM1, 2.5 mg/kg chML66-SPDB-DM4 and 5 mg/kg chML66-SPDB-DM4, respectively. This result shows that the chML66 maytansinoid conjugates are highly active in KB tumor xenograft.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. An antibody or antigen binding fragment thereof that specifically binds to human EGFR, wherein said antibody or antigen binding fragment thereof comprises:
   a) a heavy chain variable region comprising the heavy chain CDR1 of SEQ ID NO:6, the heavy chain CDR2 of SEQ ID NO:7, 9, or 10, and the heavy chain CDR3 of SEQ ID NO:8; and
   b) a light chain variable region comprising the light chain CDR1 of SEQ ID NO:14, the light chain CDR2 of SEQ ID NO:15, and the light chain CDR3 of SEQ ID NO:16.

2. The antibody or antigen binding fragment thereof of claim 1, wherein said antibody or antigen binding fragment thereof comprises:
   a) a heavy chain variable region comprising the heavy chain CDR1 of SEQ ID NO:6, the heavy chain CDR2 of SEQ ID NO:7, and the heavy chain CDR3 of SEQ ID NO:8; and
   b) a light chain variable region comprising the light chain CDR1 of SEQ ID NO:14, the light chain CDR2 of SEQ ID NO:15, and the light chain CDR3 of SEQ ID NO:16.

3. The antibody or antigen binding fragment thereof of claim 1, wherein said antibody or antigen binding fragment thereof comprises:
   a) a heavy chain variable region comprising the heavy chain CDR1 of SEQ ID NO:6, the heavy chain CDR2 of SEQ ID NO:10, and the heavy chain CDR3 of SEQ ID NO:8; and
   b) a light chain variable region comprising the light chain CDR1 of SEQ ID NO:14, the light chain CDR2 of SEQ ID NO:15, and the light chain CDR3 of SEQ ID NO:16.

4. The antibody or antigen binding fragment thereof of claim 1, wherein said antibody or antigen binding fragment thereof comprises:
   a) a heavy chain variable region comprising the heavy chain CDR1 of SEQ ID NO:6, the heavy chain CDR2 of SEQ ID NO:9, and the heavy chain CDR3 of SEQ ID NO:8; and
   b) a light chain variable region comprising the light chain CDR1 of SEQ ID NO:14, the light chain CDR2 of SEQ ID NO:15, and the light chain CDR3 of SEQ ID NO:16.

5. The antibody or antigen binding fragment thereof of claim 1, wherein said antibody or antigen binding fragment thereof comprises the heavy chain variable region of SEQ ID NO:20 and the light chain variable region of SEQ ID NO:24.

6. The antibody or antigen binding fragment thereof of claim 1, wherein said antibody or antigen binding fragment thereof comprises the heavy chain variable region of SEQ ID NO:19 and the light chain variable region of SEQ ID NO:23.

7. The antibody or antigen binding fragment thereof of claim 1, wherein said antibody or antigen binding fragment thereof is murine, non-human, humanized, chimeric, resurfaced, or human.

8. The antibody or antigen binding fragment thereof of claim 1, wherein said antibody or antigen binding fragment thereof comprises the full length heavy chain of SEQ ID NO:27 and the full length light chain of SEQ ID NO:28.

9. The antibody or antigen binding fragment thereof of claim 1, which is a full length antibody.

10. The antibody or antigen binding fragment thereof of claim 1, which is an antigen binding fragment.

11. The antibody or antigen binding fragment thereof of claim 1, wherein said antibody or antigen binding fragment thereof comprises a Fab, Fab', F(ab')2, single chain Fv or scFv, disulfide linked Fv, intrabody, IgGΔCH2, minibody, F(ab')3, tetrabody, triabody, diabody, DVD-Ig, mAb2, (scFv)2, or scFv-Fc.

12. The antibody or antigen binding fragment thereof of claim 1, wherein said antibody or antigen binding fragment thereof binds both human and macaque EGFR with a substantially similar binding affinity.

13. The antibody or antigen binding fragment thereof of claim 12, wherein the binding affinity is measured by flow cytometry, Biacore, or radioimmunoassay.

14. The antibody or antigen binding fragment thereof of claim 1, wherein said antibody or antigen binding fragment thereof binds to human or macaque EGFR with a Kd of about 1.0 to about 10 nM.

15. The antibody or antigen binding fragment thereof of claim 1, wherein said antibody or antigen binding fragment thereof binds to human or macaque EGFR with a Kd of about 1.0 nM or better.

16. The antibody or antigen binding fragment thereof of claim 1, wherein the antibody or antigen binding fragment thereof is produced by the hybridoma deposited with the ATCC on Oct. 21, 2010 and having ATCC deposit no. PTA-11423.

17. A pharmaceutical composition comprising the antibody or antigen binding fragment thereof of claim 1 and a pharmaceutically acceptable carrier.

18. A kit comprising the antibody or antigen binding fragment thereof of claim 1.

19. A diagnostic reagent comprising the antibody or antigen binding fragment thereof of claim 1.

20. An immunoconjugate having the formula (A)-(L)-(C), wherein:
- (A) is an antibody or antigen binding fragment thereof that specifically binds to human EGFR comprising a heavy chain variable region comprising the heavy chain CDR1 of SEQ ID NO:6, the heavy chain CDR2 of SEQ ID NO:7, 9, or 10, and the heavy chain CDR3 of SEQ ID NO:8; and a light chain variable region comprising the light chain CDR1 of SEQ ID NO:14, the light chain CDR2 of SEQ ID NO:15, and the light chain CDR3 of SEQ ID NO:16;
- (L) is a linker;
- (C) is a cytotoxic agent; and
- wherein said linker (L) links (A) to (C).

21. The immunoconjugate of claim 20, wherein (A) comprises a heavy chain variable region comprising the heavy chain CDR1 of SEQ ID NO:6, the heavy chain CDR2 of SEQ ID NO:7, and the heavy chain CDR3 of SEQ ID NO:8; and a light chain variable region comprising the light chain CDR1 of SEQ ID NO:14, the light chain CDR2 of SEQ ID NO:15, and the light chain CDR3 of SEQ ID NO:16.

22. The immunoconjugate of claim 20, wherein (A) comprises a heavy chain variable region comprising the heavy chain CDR1 of SEQ ID NO:6, the heavy chain CDR2 of SEQ ID NO:10, and the heavy chain CDR3 of SEQ ID NO:8; and a light chain variable region comprising the light chain CDR1 of SEQ ID NO:14, the light chain CDR2 of SEQ ID NO:15, and the light chain CDR3 of SEQ ID NO:16.

23. The immunoconjugate of claim 20, wherein (A) comprises a heavy chain variable region comprising the heavy chain CDR1 of SEQ ID NO:6, the heavy chain CDR2 of SEQ ID NO:9, and the heavy chain CDR3 of SEQ ID NO:8; and a light chain variable region comprising the light chain CDR1 of SEQ ID NO:14, the light chain CDR2 of SEQ ID NO:15, and the light chain CDR3 of SEQ ID NO:16.

24. The immunoconjugate of claim 20, wherein (A) comprises an antibody or antigen binding fragment thereof comprising the heavy chain variable domain of SEQ ID NO:20 and the light chain variable domain of SEQ ID NO:24.

25. The immunoconjugate of claim 20, wherein (A) comprises an antibody or antigen binding fragment thereof comprising the heavy chain variable domain of SEQ ID NO:19 and the light chain variable domain of SEQ ID NO:23.

26. The immunoconjugate of claim 20, wherein (L) is selected from the group consisting of: a cleavable linker, a non-cleavable linker, a hydrophilic linker, and a dicarboxylic acid based linker.

27. The immunoconjugate of claim 26, wherein (L) comprises a linker selected from the group consisting of: N-succinimidyl 4-(2-pyridyldithio)pentanoate (SPP), N-succinimidyl 4-(2-pyridyldithio)butanoate (SPDB), N-succinimidyl 4-(2-pyridyldithio)-2-sulfobutanoate (sulfo-SPDB), N-succinimidyl 4-(maleimidomethyl) cyclohexanecarboxylate (SMCC), N-sulfosuccinimidyl 4-(maleimidomethyl) cyclohexanecarboxylate (sulfoSMCC), N-succinimidyl-4-(iodoacetyl)-aminobenzoate (SIAB), and N-succinimidyl-[(N-maleimidopropionamido)-tetraethyleneglycol]ester (NHS-PEG4-maleimide).

28. The immunoconjugate of claim 20, wherein (C) comprises a cytotoxic agent selected from the group consisting of: a maytansinoid, a maytansinoid analog, benzodiazepine, taxoid, CC-1065, CC-1065 analog, duocarmycin, duocarmycin analog, calicheamicin, dolastatin, dolastatin analog, auristatin, tomaymycin derivative, doxorubicin, leptomycin derivative, methotrexate, cisplatin, carboplatin, daunorubicin, vincristine, vinblastine, melphalan, mitomycin C, chlorambucil and morpholino doxorubicin, or a prodrug of the cytotoxic agent.

29. The immunoconjugate of claim 28, wherein said immunoconjugate comprises multiple (C) with an average of 2 to 8 (C) per (A).

30. The immunoconjugate of claim 29, wherein (C) comprises a maytansinoid.

31. The immunoconjugate of claim 30, wherein (C) comprises N(2')-deacetyl-N (2')-(3-mercapto-1-oxopropyl)-maytansine (DM1) or N(2')-deacetyl-N(2')-(4-mercapto-4-methyl-1-oxopentyl)-maytansine (DM4).

32. The immunoconjugate of claim 31, wherein (L) is a N-succinimidyl 4-(maleimidomethyl) cyclohexanecarboxylate (SMCC) linker, and wherein (C) is the cytotoxic agent N(2')-deacetyl-N(2')-(3-mercapto-1-oxopropyl)-maytansine (DM1).

33. The immunoconjugate of claim 31, wherein (L) is a N-succinimidyl 4-(2-pyridyldithio) butanoate (SPDB) linker, and wherein (C) is the cytotoxic agent N(2')-deacetyl-N (2')-(4-mercapto-4-methyl-1-oxopentyl)-maytansine (DM4).

34. The immunoconjugate of claim 20, wherein:
- (A) is an antibody or antigen binding fragment thereof comprising the heavy chain variable region of SEQ ID NO:20 and the light chain variable region of SEQ ID NO:24;
- (L) is a N-succinimidyl 4-(maleimidomethyl) cyclohexanecarboxylate (SMCC) linker; and
- (C) is the cytotoxic agent N(2')-deacetyl-N(2')-(3-mercapto-1-oxopropyl)-maytansine (DM1).

35. The immunoconjugate of claim 20, wherein:
- (A) is an antibody or antigen binding fragment thereof comprising the heavy chain variable region of SEQ ID NO:20 and the light chain variable region of SEQ ID NO:24;
- (L) is a N-succinimidyl 4-(2-pyridyldithio) butanoate (SPDB) linker; and
- (C) is the cytotoxic agent N(2')-deacetyl-N(2')-(4-mercapto-4-methyl-l-oxopentyl)-maytansine (DM4).

36. A pharmaceutical composition comprising the immunoconjugate of claim 20 and a pharmaceutically acceptable carrier.

37. A kit comprising the immunoconjugate of claim 20.

38. A diagnostic reagent comprising the immunoconjugate of claim 20.

* * * * *

UNITED STATES PATENT AND TRADEMARK OFFICE
CERTIFICATE OF CORRECTION

PATENT NO.        : 9,238,690 B2
APPLICATION NO.   : 13/882059
DATED             : January 19, 2016
INVENTOR(S)       : Setiady et al.

It is certified that error appears in the above-identified patent and that said Letters Patent is hereby corrected as shown below:

Claims

At column 98, lines 7-8 (claim 27), please replace
"N-succinimidyl-[(N-maleimidopropionamido) –tetraethyleneglycol]ester" with
--N-succinimidyl-[(N-maleimidopropionamido)–tetraethyleneglycol]ester--;

At column 98, lines 26-27 (claim 31), please replace
"N(2')-deacetyl-N (2')-(3-mercapto-1-oxopropyl)-maytansine" with
--N(2')-deacetyl-N(2')-(3-mercapto-1-oxopropyl)-maytansine--; and At column 98, lines 36-37 (claim 33), please replace
"N(2')-deacetyl-N (2')-(4-mercapto-4-methyl-1-oxopentyl)-maytansine" with
--N(2')-deacetyl-N(2')-(4-mercapto-4-methyl-1-oxopentyl)-maytansine--.

Signed and Sealed this
Twelfth Day of April, 2016

Michelle K. Lee
*Director of the United States Patent and Trademark Office*

SEQUENCE LISTING

```
<160> NUMBER OF SEQ ID NOS: 45

<210> SEQ ID NO 1
<211> LENGTH: 6
<212> TYPE: PRT
<213> ORGANISM: Artificial
<220> FEATURE:
<223> OTHER INFORMATION: ML66 VH-CDR1

<400> SEQUENCE: 1

Ala Ser Asn Ser Val Ser
1               5

<210> SEQ ID NO 2
<211> LENGTH: 9
<212> TYPE: PRT
<213> ORGANISM: Artificial
<220> FEATURE:
<223> OTHER INFORMATION: ML66 VH-CDR2

<400> SEQUENCE: 2

Val Ile Trp Asn His Gly Gly Thr Asp
1               5

<210> SEQ ID NO 3
<211> LENGTH: 8
<212> TYPE: PRT
<213> ORGANISM: Artificial
<220> FEATURE:
<223> OTHER INFORMATION: ML66 VH-CDR3

<400> SEQUENCE: 3

Lys Gly Gly Ile Tyr Phe Asp Tyr
1               5

<210> SEQ ID NO 4
<211> LENGTH: 16
<212> TYPE: PRT
<213> ORGANISM: Artificial
<220> FEATURE:
<223> OTHER INFORMATION: ML66 Kabat HC CDR2 (rat), VH-CDR2

<400> SEQUENCE: 4

Val Ile Trp Asn His Gly Gly Thr Asp Tyr Asn Ser Val Ile Lys Ser
1               5                   10                  15

<210> SEQ ID NO 5
<211> LENGTH: 16
<212> TYPE: PRT
<213> ORGANISM: Artificial
<220> FEATURE:
<223> OTHER INFORMATION: ML66 Kabat HC CDR2 (humanized), VH-CDR2

<400> SEQUENCE: 5

Val Ile Trp Asn His Gly Gly Thr Asp Tyr Asn Pro Ser Ile Lys Ser
1               5                   10                  15

<210> SEQ ID NO 6
<211> LENGTH: 6
<212> TYPE: PRT
<213> ORGANISM: Artificial
<220> FEATURE:
<223> OTHER INFORMATION: EGFR-8 VH-CDR1

<400> SEQUENCE: 6

Lys Asp Thr Tyr Ile His
1               5
```

<210> SEQ ID NO 7
<211> LENGTH: 10
<212> TYPE: PRT
<213> ORGANISM: Artificial
<220> FEATURE:
<223> OTHER INFORMATION: EGFR-8 VH-CDR2

<400> SEQUENCE: 7

Arg Ile Asp Pro Thr Asn Gly Asn Asn Lys
1               5                   10

<210> SEQ ID NO 8
<211> LENGTH: 13
<212> TYPE: PRT
<213> ORGANISM: Artificial
<220> FEATURE:
<223> OTHER INFORMATION: EGFR-8 VH-CDR3

<400> SEQUENCE: 8

Glu Asp Gly Tyr Arg Tyr Asp Asp Trp Tyr Phe Asp Val
1               5                   10

<210> SEQ ID NO 9
<211> LENGTH: 17
<212> TYPE: PRT
<213> ORGANISM: Artificial
<220> FEATURE:
<223> OTHER INFORMATION: EGFR-8 Kabat HC CDR2 (murine), VH-CDR2

<400> SEQUENCE: 9

Arg Ile Asp Pro Thr Asn Gly Asn Asn Lys Tyr Asp Pro Lys Phe Gln
1               5                   10                  15

Gly

<210> SEQ ID NO 10
<211> LENGTH: 17
<212> TYPE: PRT
<213> ORGANISM: Artificial
<220> FEATURE:
<223> OTHER INFORMATION: EGFR-8 Kabat HC CDR2, VH-CDR2

<400> SEQUENCE: 10

Arg Ile Asp Pro Thr Asn Gly Asn Asn Lys Tyr Asp Gln Lys Phe Gln
1               5                   10                  15

Gly

<210> SEQ ID NO 11
<211> LENGTH: 11
<212> TYPE: PRT
<213> ORGANISM: Artificial
<220> FEATURE:
<223> OTHER INFORMATION: ML66 VL-CDR1

<400> SEQUENCE: 11

Arg Ala Ser Glu Ser Val Ser Thr Leu Met His
1               5                   10

<210> SEQ ID NO 12
<211> LENGTH: 7
<212> TYPE: PRT
<213> ORGANISM: Artificial
<220> FEATURE:
<223> OTHER INFORMATION: ML66 VL-CDR2

<400> SEQUENCE: 12

```
Leu Ala Ser His Arg Glu Ser
1               5

<210> SEQ ID NO 13
<211> LENGTH: 9
<212> TYPE: PRT
<213> ORGANISM: Artificial
<220> FEATURE:
<223> OTHER INFORMATION: ML66 VL-CDR3

<400> SEQUENCE: 13

Gln Gln Ser Arg Asn Asp Pro Trp Thr
1               5

<210> SEQ ID NO 14
<211> LENGTH: 10
<212> TYPE: PRT
<213> ORGANISM: Artificial
<220> FEATURE:
<223> OTHER INFORMATION: EGFR-8 VL-CDR1

<400> SEQUENCE: 14

Ser Ala Ser Ser Ser Val Ser Tyr Met His
1               5                   10

<210> SEQ ID NO 15
<211> LENGTH: 7
<212> TYPE: PRT
<213> ORGANISM: Artificial
<220> FEATURE:
<223> OTHER INFORMATION: EGFR-8 VL-CDR2

<400> SEQUENCE: 15

Ala Thr Ser Lys Leu Ala Ser
1               5

<210> SEQ ID NO 16
<211> LENGTH: 9
<212> TYPE: PRT
<213> ORGANISM: Artificial
<220> FEATURE:
<223> OTHER INFORMATION: EGFR-8 VL-CDR3

<400> SEQUENCE: 16

Gln Gln Trp Ser Ser Asn Pro Leu Thr
1               5

<210> SEQ ID NO 17
<211> LENGTH: 116
<212> TYPE: PRT
<213> ORGANISM: Artificial
<220> FEATURE:
<223> OTHER INFORMATION: ratML66 VH

<400> SEQUENCE: 17

Gln Val Gln Leu Lys Glu Ser Gly Pro Gly Leu Val Gln Pro Ser Gln
1               5                   10                  15

Thr Leu Ser Leu Thr Cys Thr Val Ser Gly Leu Ser Leu Ala Ser Asn
            20                  25                  30

Ser Val Ser Trp Ile Arg Gln Pro Pro Gly Lys Gly Leu Glu Trp Met
        35                  40                  45

Gly Val Ile Trp Asn His Gly Gly Thr Asp Tyr Asn Ser Val Ile Lys
    50                  55                  60

Ser Arg Leu Ser Ile Ser Arg Asp Thr Ser Lys Ser Gln Val Phe Leu
```

```
              65                  70                  75                  80
Lys Met Asn Ser Leu Gln Thr Glu Asp Thr Ala Met Tyr Phe Cys Val
                    85                  90                  95

Arg Lys Gly Gly Ile Tyr Phe Asp Tyr Trp Gly Gln Gly Val Met Val
                100                 105                 110

Thr Val Ser Ser
        115

<210> SEQ ID NO 18
<211> LENGTH: 116
<212> TYPE: PRT
<213> ORGANISM: Artificial
<220> FEATURE:
<223> OTHER INFORMATION: huML66 VH

<400> SEQUENCE: 18

Gln Val Gln Leu Gln Glu Ser Gly Pro Gly Leu Val Lys Pro Ser Glu
1               5                   10                  15

Thr Leu Ser Leu Thr Cys Thr Val Ser Gly Leu Ser Leu Ala Ser Asn
                20                  25                  30

Ser Val Ser Trp Ile Arg Gln Pro Pro Gly Lys Gly Leu Glu Trp Met
            35                  40                  45

Gly Val Ile Trp Asn His Gly Gly Thr Asp Tyr Asn Pro Ser Ile Lys
        50                  55                  60

Ser Arg Leu Ser Ile Ser Arg Asp Thr Ser Lys Ser Gln Val Phe Leu
65                  70                  75                  80

Lys Met Asn Ser Leu Thr Ala Ala Asp Thr Ala Met Tyr Phe Cys Val
                85                  90                  95

Arg Lys Gly Gly Ile Tyr Phe Asp Tyr Trp Gly Gln Gly Val Leu Val
                100                 105                 110

Thr Val Ser Ser
        115

<210> SEQ ID NO 19
<211> LENGTH: 122
<212> TYPE: PRT
<213> ORGANISM: Artificial
<220> FEATURE:
<223> OTHER INFORMATION: muEGFR-8 VH

<400> SEQUENCE: 19

Glu Val Gln Leu Gln Gln Ser Gly Ala Glu Leu Val Lys Pro Gly Ala
1               5                   10                  15

Ser Val Lys Leu Ser Cys Thr Thr Ser Gly Phe Asn Ile Lys Asp Thr
                20                  25                  30

Tyr Ile His Trp Val Lys Lys Arg Pro Glu Gln Gly Leu Glu Trp Ile
            35                  40                  45

Gly Arg Ile Asp Pro Thr Asn Gly Asn Asn Lys Tyr Asp Pro Lys Phe
        50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Arg Glu Asp Gly Tyr Arg Tyr Asp Asp Trp Tyr Phe Asp Val Trp
                100                 105                 110

Gly Ala Gly Thr Thr Val Thr Val Ser Ser
        115                 120
```

```
<210> SEQ ID NO 20
<211> LENGTH: 122
<212> TYPE: PRT
<213> ORGANISM: Artificial
<220> FEATURE:
<223> OTHER INFORMATION: huEGFR-8 VH

<400> SEQUENCE: 20

Gln Val Gln Leu Val Gln Ser Gly Ala Glu Val Val Lys Pro Gly Ala
1               5                   10                  15

Ser Val Lys Leu Ser Cys Thr Thr Ser Gly Phe Thr Ile Lys Asp Thr
            20                  25                  30

Tyr Ile His Trp Val Lys Lys Arg Pro Gly Gln Gly Leu Glu Trp Ile
        35                  40                  45

Gly Arg Ile Asp Pro Thr Asn Gly Asn Asn Lys Tyr Asp Gln Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Arg Glu Asp Gly Tyr Arg Tyr Asp Asp Trp Tyr Phe Asp Val Trp
            100                 105                 110

Gly Gln Gly Thr Leu Val Thr Val Ser Ser
        115                 120

<210> SEQ ID NO 21
<211> LENGTH: 107
<212> TYPE: PRT
<213> ORGANISM: Artificial
<220> FEATURE:
<223> OTHER INFORMATION: ratML66 VL

<400> SEQUENCE: 21

Asp Thr Val Leu Thr Gln Ser Pro Ala Leu Ala Val Ser Pro Gly Glu
1               5                   10                  15

Arg Val Thr Ile Ser Cys Arg Ala Ser Glu Ser Val Ser Thr Leu Met
            20                  25                  30

His Trp Tyr Gln Gln Lys Ser Gly Gln Gln Pro Lys Leu Leu Ile Tyr
        35                  40                  45

Leu Ala Ser His Arg Glu Ser Gly Val Pro Ala Arg Phe Ser Gly Ser
    50                  55                  60

Gly Ser Gly Thr Asp Phe Thr Leu Thr Ile Asp Pro Met Glu Ala Asp
65                  70                  75                  80

Asp Thr Ala Thr Tyr Tyr Cys Gln Gln Ser Arg Asn Asp Pro Trp Thr
                85                  90                  95

Phe Gly Gly Gly Thr Asn Leu Glu Leu Lys Arg
            100                 105

<210> SEQ ID NO 22
<211> LENGTH: 107
<212> TYPE: PRT
<213> ORGANISM: Artificial
<220> FEATURE:
<223> OTHER INFORMATION: huML66 VL

<400> SEQUENCE: 22

Asp Thr Val Leu Thr Gln Ser Pro Ser Leu Ala Val Ser Pro Gly Glu
1               5                   10                  15

Arg Ala Thr Ile Ser Cys Arg Ala Ser Glu Ser Val Ser Thr Leu Met
```

```
            20                  25                  30

His Trp Tyr Gln Gln Lys Pro Gly Gln Gln Pro Lys Leu Leu Ile Tyr
            35                  40                  45

Leu Ala Ser His Arg Glu Ser Gly Val Pro Ala Arg Phe Ser Gly Ser
 50                  55                  60

Gly Ser Gly Thr Asp Phe Thr Leu Thr Ile Asp Pro Met Glu Ala Glu
 65                  70                  75                  80

Asp Thr Ala Thr Tyr Tyr Cys Gln Gln Ser Arg Asn Asp Pro Trp Thr
                 85                  90                  95

Phe Gly Gln Gly Thr Lys Leu Glu Leu Lys Arg
                100                 105

<210> SEQ ID NO 23
<211> LENGTH: 107
<212> TYPE: PRT
<213> ORGANISM: Artificial
<220> FEATURE:
<223> OTHER INFORMATION: muEGFR-8 VL

<400> SEQUENCE: 23

Gln Ile Val Leu Thr Gln Ser Pro Ala Ser Met Ser Ala Ser Pro Gly
 1               5                  10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
            35                  40                  45

Ala Thr Ser Lys Leu Ala Ser Gly Val Pro Ala Arg Phe Ser Gly Ser
 50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Ser Ser Asn Pro Leu Thr
                 85                  90                  95

Phe Gly Ala Gly Thr Lys Leu Glu Leu Lys Arg
                100                 105

<210> SEQ ID NO 24
<211> LENGTH: 107
<212> TYPE: PRT
<213> ORGANISM: Artificial
<220> FEATURE:
<223> OTHER INFORMATION: huEGFR-8 VL

<400> SEQUENCE: 24

Asp Ile Val Leu Thr Gln Ser Pro Ala Phe Met Ser Ala Ser Pro Gly
 1               5                  10                  15

Glu Lys Val Thr Met Thr Cys Ser Ala Ser Ser Ser Val Ser Tyr Met
            20                  25                  30

His Trp Tyr Gln Gln Lys Pro Asp Gln Ser Pro Lys Arg Trp Ile Tyr
            35                  40                  45

Ala Thr Ser Lys Leu Ala Ser Gly Val Pro Ser Arg Phe Ser Gly Ser
 50                  55                  60

Gly Ser Gly Thr Asp Tyr Ser Leu Thr Ile Ser Ser Met Glu Ala Glu
 65                  70                  75                  80

Asp Ala Ala Thr Tyr Tyr Cys Gln Gln Trp Ser Ser Asn Pro Leu Thr
                 85                  90                  95

Phe Gly Gln Gly Thr Lys Leu Glu Leu Lys Arg
                100                 105
```

<210> SEQ ID NO 25
<211> LENGTH: 445
<212> TYPE: PRT
<213> ORGANISM: Artificial
<220> FEATURE:
<223> OTHER INFORMATION: huML66HC, full-Length Heavy/Light Chain

<400> SEQUENCE: 25

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Leu Ser Leu Ala Ser Asn
            20                  25                  30

Ser Val Ser Trp Ile Arg Gln Pro Pro Gly Lys Gly Leu Glu Trp Met
        35                  40                  45

Gly Val Ile Trp Asn His Gly Gly Thr Asp Tyr Asn Pro Ser Ile Lys
    50                  55                  60

Ser Arg Leu Ser Ile Ser Arg Asp Thr Ser Lys Ser Gln Val Phe Leu
65                  70                  75                  80

Lys Met Asn Ser Leu Thr Ala Ala Asp Thr Ala Met Tyr Phe Cys Val
                85                  90                  95

Arg Lys Gly Gly Ile Tyr Phe Asp Tyr Trp Gly Gln Gly Val Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365
```

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly
                435                 440                 445

<210> SEQ ID NO 26
<211> LENGTH: 213
<212> TYPE: PRT
<213> ORGANISM: Artificial
<220> FEATURE:
<223> OTHER INFORMATION: huML66LC, full-Length Heavy/Light Chain

<400> SEQUENCE: 26

Asp Thr Val Leu Thr Gln Ser Pro Ser Leu Ala Val Ser Pro Gly Glu
1               5                   10                  15

Arg Ala Thr Ile Ser Cys Arg Ala Ser Glu Ser Val Ser Thr Leu Met
                20                  25                  30

His Trp Tyr Gln Gln Lys Pro Gly Gln Gln Pro Lys Leu Leu Ile Tyr
            35                  40                  45

Leu Ala Ser His Arg Glu Ser Gly Val Pro Ala Arg Phe Ser Gly Ser
        50                  55                  60

Gly Ser Gly Thr Asp Phe Thr Leu Thr Ile Asp Pro Met Glu Ala Glu
65                  70                  75                  80

Asp Thr Ala Thr Tyr Tyr Cys Gln Gln Ser Arg Asn Asp Pro Trp Thr
                85                  90                  95

Phe Gly Gln Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 27
<211> LENGTH: 451
<212> TYPE: PRT
<213> ORGANISM: Artificial
<220> FEATURE:
<223> OTHER INFORMATION: huEGFR-8 HC, full-Length Heavy/Light Chain

<400> SEQUENCE: 27

Gln Val Gln Leu Val Gln Ser Gly Ala Glu Val Val Lys Pro Gly Ala
1               5                   10                  15

```
Ser Val Lys Leu Ser Cys Thr Ser Gly Phe Thr Ile Lys Asp Thr
         20                  25                  30
Tyr Ile His Trp Val Lys Arg Pro Gly Gln Gly Leu Glu Trp Ile
         35                  40                  45
Gly Arg Ile Asp Pro Thr Asn Gly Asn Lys Tyr Asp Gln Lys Phe
 50                  55                  60
Gln Gly Lys Ala Thr Ile Thr Ala Asp Thr Ser Ser Asn Thr Ala Tyr
 65                  70                  75                  80
Leu Gln Leu Ser Ser Leu Thr Ser Glu Asp Thr Ala Val Tyr Tyr Cys
             85                  90                  95
Thr Arg Glu Asp Gly Tyr Arg Tyr Asp Asp Trp Tyr Phe Asp Val Trp
            100                 105                 110
Gly Gln Gly Thr Leu Val Thr Val Ser Ser Ala Ser Thr Lys Gly Pro
            115                 120                 125
Ser Val Phe Pro Leu Ala Pro Ser Ser Lys Ser Thr Ser Gly Gly Thr
130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                    165                 170                 175
Ala Val Leu Gln Ser Ser Gly Leu Tyr Ser Leu Ser Ser Val Val Thr
                    180                 185                 190
Val Pro Ser Ser Ser Leu Gly Thr Gln Thr Tyr Ile Cys Asn Val Asn
                    195                 200                 205
His Lys Pro Ser Asn Thr Lys Val Asp Lys Lys Val Glu Pro Lys Ser
        210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                    245                 250                 255
Met Ile Ser Arg Thr Pro Glu Val Thr Cys Val Val Val Asp Val Ser
                    260                 265                 270
His Glu Asp Pro Glu Val Lys Phe Asn Trp Tyr Val Asp Gly Val Glu
                    275                 280                 285
Val His Asn Ala Lys Thr Lys Pro Arg Glu Glu Gln Tyr Asn Ser Thr
        290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                    325                 330                 335
Ile Glu Lys Thr Ile Ser Lys Ala Lys Gly Gln Pro Arg Glu Pro Gln
                    340                 345                 350
Val Tyr Thr Leu Pro Pro Ser Arg Asp Glu Leu Thr Lys Asn Gln Val
                    355                 360                 365
Ser Leu Thr Cys Leu Val Lys Gly Phe Tyr Pro Ser Asp Ile Ala Val
                    370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                    405                 410                 415
Val Asp Lys Ser Arg Trp Gln Gln Gly Asn Val Phe Ser Cys Ser Val
                    420                 425                 430
```

Met His Glu Ala Leu His Asn His Tyr Thr Gln Lys Ser Leu Ser Leu
            435                 440                 445

Ser Pro Gly
    450

<210> SEQ ID NO 28
<211> LENGTH: 213
<212> TYPE: PRT
<213> ORGANISM: Artificial
<220> FEATURE:
<223> OTHER INFORMATION: huEGFR-8 LC, full-Length Heavy/Light Chain

<400> SEQUENCE: 28

Asp Ile Val Leu Thr Gln Ser Pro Ala Phe Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Pro Asp Gln Ser Pro Lys Arg Trp Ile Tyr
        35                  40                  45

Ala Thr Ser Lys Leu Ala Ser Gly Val Pro Ser Arg Phe Ser Gly Ser
    50                  55                  60

Gly Ser Gly Thr Asp Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Gln Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 29
<211> LENGTH: 348
<212> TYPE: DNA
<213> ORGANISM: Artificial
<220> FEATURE:
<223> OTHER INFORMATION: ratML66 VH polynucleotide

<400> SEQUENCE: 29
caagtgcaac taaaggagtc aggacctggt ctggtacagc catcacagac cctgtctctc      60
acctgcactg tctctgggtt atcattagcc agcaatagtg taagctggat tcggcagcct     120
ccaggaaagg gtctggagtg gatgggagta atatggaatc atggaggcac agattataat     180
tcagttatca aatcccgact gagcatcagc aggacacct cgaagagcca agttttctta      240
aagatgaaca gtctgcagac tgaagacaca gccatgtact tctgtgtcag aaagggtggg     300
atctactttg attactgggg tcaaggagtc atggtcacag tctcctca                  348

<210> SEQ ID NO 30
<211> LENGTH: 366
<212> TYPE: DNA
<213> ORGANISM: Artificial
<220> FEATURE:
<223> OTHER INFORMATION: muEGFR-8 VH polynucleotide

<400> SEQUENCE: 30

```
gaggttcagc tgcagcagtc tggggcagag cttgtgaagc caggggcctc agtcaagttg      60
tcctgcacaa cttctggctt caacattaaa gacacctata tacactgggt gaagaagagg     120
cctgaacagg gcctggagtg gattggaagg attgatccta cgaatggaaa taataaatat     180
gacccgaagt tccagggcaa ggccactata acagcagaca tcttccaa cacagcctac       240
ctgcagctca gcagcctgac atctgaggac actgccgtct attactgtac tagagaagat     300
gggtataggt acgacgactg gtacttcgat gtctggggcg cagggaccac ggtcaccgtc     360
tcctca                                                                366
```

<210> SEQ ID NO 31
<211> LENGTH: 434
<212> TYPE: DNA
<213> ORGANISM: Artificial
<220> FEATURE:
<223> OTHER INFORMATION: huML66 VH polynucleotide

<400> SEQUENCE: 31

```
aagcttgcca ccatgggttg gtcttgcatt atccttttcc tggttgcaac agccacaggc      60
gttcacagtc aagtgcagct gcaggaatcc ggccccggac tggttaagcc cagcgagacc     120
ctctctctga catgcacagt cagcgggctg agcttggcta gtaacagcgt cagttggatc     180
aggcagcctc ctgggaaggg gctggagtgg atgggagtaa tctggaacca cgggggtacc     240
gactacaatc catctattaa gagccgcctg agtatctcac gggacaccag caaatctcaa     300
gtgtttctga agatgaatag cctgactgca gccgatacag ccatgtactt ctgtgtccgg     360
aagggtggca tttacttcga ctattggggt cagggtgtcc tggtgactgt ctcttcagcc     420
agcaccaagg gccc                                                       434
```

<210> SEQ ID NO 32
<211> LENGTH: 452
<212> TYPE: DNA
<213> ORGANISM: Artificial
<220> FEATURE:
<223> OTHER INFORMATION: huEGFR-8 VH polynucleotide

<400> SEQUENCE: 32

```
aagcttgcca ccatgggctg gtcatgcatc atcttgtttt tggtggcaac tgccactggt      60
gtccattctc aagtacagct tgtacagtca ggtgctgaag tcgtcaagcc cggggccagt     120
gtcaagctgt cctgtactac atctggattt acaataaaag acacctacat tcactgggtg     180
aagaagaggc ccgggcaggg gctggagtgg attggccgga ttgatcccac aaatggcaac     240
aataaatatg accagaaatt ccaaggcaaa gccaccatca ctgcagatac ctcaagtaac     300
actgcttacc tgcagttgtc ttctctgaca tccgaggata cagccgtgta ctactgcact     360
agagaggatg gatacagata tgacgactgg tacttcgatg tgtggggcca ggggaccctg     420
gtcactgttt cctccgcttc cacaaagggc cc                                   452
```

<210> SEQ ID NO 33

```
<211> LENGTH: 321
<212> TYPE: DNA
<213> ORGANISM: Artificial
<220> FEATURE:
<223> OTHER INFORMATION: ratML66 VL polynucleotide

<400> SEQUENCE: 33
gacactgtac tgacccagtc tcctgctttg gctgtgtctc aggagagag ggttaccatc      60 tcctgtaggg ccagtgagag tgtcagtaca cttatgcact ggtaccaaca gaaatcagga     120
cagcaaccca aactcctcat ctatctagca tcacaccgag aatctggggt ccctgccagg    180
ttcagtggca gtgggtctgg gacagacttc accctcacca ttgatcctat ggaggctgat    240
gacactgcaa cctattactg tcagcagagt cggaatgatc cgtggacgtt cggtggaggc    300
accaacctgg aattgaaacg g                                              321

<210> SEQ ID NO 34
<211> LENGTH: 321
<212> TYPE: DNA
<213> ORGANISM: Artificial
<220> FEATURE:
<223> OTHER INFORMATION: muEGFR-8 VL polynucleotide

<400> SEQUENCE: 34
caaattgttc tcacccagtc tccagcaagc atgtctgctt ctccagggga gaaggtcacc     60
atgacctgca gtgccagctc aagtgtaagt tacatgcact ggtaccagca gaagtcaggc    120
acctccccca aaagatggat ctatgccaca tccaaactgg cttctggagt ccctgctcgc    180
ttcagtggca gtgggtctgg gacctcttac tctctcacaa tcagcagcat ggaggctgaa    240
gatgctgcca cttattactg ccagcagtgg agtagtaatc cactcacgtt cggtgctggg    300
accaagctgg agctgaaacg g                                              321

<210> SEQ ID NO 35
<211> LENGTH: 393
<212> TYPE: DNA
<213> ORGANISM: Artificial
<220> FEATURE:
<223> OTHER INFORMATION: huML66 VL polynucleotide

<400> SEQUENCE: 35
gaattcgcca ccatgggatg gtcctgtata atcctgtttc tggtcgcaac cgcaaccggc     60
gtgcactccg acactgtgct gacacagtcc ccaagcctgg ctgtttcacc tggtgaaaga    120
gctaccatca gttgtcgggc tagcgaaagc gtgtcaactc tgatgcactg gtaccagcag    180
aagcctggcc aacagcccaa actgctgata tatctggcat cacatcgtga gtccggagta    240
cctgctaggt tctctgggag cggcagcggc accgacttta ccctgacaat cgaccccatg    300
gaggccgaag atacagctac ttactactgc caacagtcta aaacgatcc atggactttt    360 ggacaaggga ccaaattgga gcttaagcgt acg                                 393

<210> SEQ ID NO 36
<211> LENGTH: 393
<212> TYPE: DNA
<213> ORGANISM: Artificial
<220> FEATURE:
<223> OTHER INFORMATION: huEGFR-8 VL polynucleotide

<400> SEQUENCE: 36
gaattcgcca ccatgggggtg gtcctgtatc attctgtttc tggtagccac agctaccggc     60
gtgcactccg acatcgtgct gacacaatcc cctgctttta tgtcagcttc tccaggagag    120
```

| | | | | |
|---|---|---|---|---|
| aaagtgacca | tgacctgctc | tgcctctagc | tctgtgtcct | acatgcactg | gtatcagcag | 180 |
| aagccagacc | agagtcctaa | gagatggatc | tacgctacca | gtaaactggc | ttctggcgtg | 240 |
| ccatctcggt | tttcaggaag | cggcagcggg | accgactact | cattgacaat | atcctctatg | 300 |
| gaggccgaag | acgctgcaac | atactactgt | cagcagtgga | gctcaaatcc | actcacattc | 360 |
| ggacagggta | caaaactgga | gctgaagcgt | acg | | | 393 |

<210> SEQ ID NO 37
<211> LENGTH: 1413
<212> TYPE: DNA
<213> ORGANISM: Artificial
<220> FEATURE:
<223> OTHER INFORMATION: huML66 HC polynucleotide

<400> SEQUENCE: 37

| | | | | | | |
|---|---|---|---|---|---|---|
| aagcttgcca | ccatggggttg | gtcttgcatt | atccttttcc | tggttgcaac | agccacaggc | 60 |
| gttcacagtc | aagtgcagct | gcaggaatcc | ggccccggac | tggttaagcc | cagcgagacc | 120 |
| ctctctctga | catgcacagt | cagcgggctg | agcttggcta | gtaacagcgt | cagttggatc | 180 |
| aggcagcctc | ctgggaaggg | gctggagtgg | atgggagtaa | tctggaacca | cggggggtacc | 240 |
| gactacaatc | catctattaa | gagccgcctg | agtatctcac | gggacaccag | caaatctcaa | 300 |
| gtgtttctga | agatgaatag | cctgactgca | gccgatacag | ccatgtactt | ctgtgtccgg | 360 |
| aagggtggca | tttacttcga | ctattgggggt | cagggtgtcc | tgctgactgt | ctcttcagcc | 420 |
| agcaccaagg | gcccatcagt | tttcccctttg | gctccaagtt | ctaaatccac | aagcggtgga | 480 |
| acagctgcac | tgggatgcct | cgttaaagat | tatttccctg | agcctgtgac | agtgagctgg | 540 |
| aatagcggag | cattgacttc | aggtgtgcac | acttttcccg | ctgtgttgca | gtcctccggt | 600 |
| ctgtactcac | tgtccagtgt | cgtaaccgtc | ccttctagca | gcttgggaac | ccagacctac | 660 |
| atctgtaacg | tcaaccataa | accatccaac | acaaaggtgg | ataagaaggt | tgaaccaaag | 720 |
| agctgtgata | agacacatac | atgccctcct | tgtcctgcac | cagagctcct | cggaggtcca | 780 |
| tctgtgttcc | tgtttccccc | caaacccaag | gacactctta | tgatctctcg | tactccagag | 840 |
| gtcacctgtg | ttgttgtcga | cgtgagccat | gaagatcccg | aggttaaatt | caactggtac | 900 |
| gtggatggag | tcgaggttca | caatgccaag | accaagccca | gggaggagca | atataattct | 960 |
| acatatcggg | tagtgagcgt | tctgaccgtg | ctccaccaag | attggctcaa | tggaaaagag | 1020 |
| tacaagtgca | aggtgtccaa | caaggctctt | cccgctccca | ttgagaaaac | tatctccaaa | 1080 |
| gccaaggggc | agccacggga | accccaggtg | tatacattgc | ccccatctag | agacgagctg | 1140 |
| accaagaacc | aggtgagtct | cacttgtctg | gtcaaggggt | tttacccttc | tgacattgct | 1200 |
| gtagagtggg | agtctaacgg | acagccagaa | aacaactaca | agacaactcc | cccagtgctg | 1260 |
| gacagcgacg | ggagcttctt | cctctactcc | aagttgactg | tagacaagtc | tagatggcag | 1320 |
| caaggaaacg | ttttctcctg | ctcagtaatg | catgaggctc | tgcacaatca | ctatacccag | 1380 |
| aaatcactgt | cccttagccc | agggtgactc | gag | | | 1413 |

<210> SEQ ID NO 38
<211> LENGTH: 711
<212> TYPE: DNA
<213> ORGANISM: Artificial
<220> FEATURE:
<223> OTHER INFORMATION: huML66 LC polynucleotide

<400> SEQUENCE: 38

| | |
|---|---|
| gaattcgcca ccatgggatg gtcctgtata atcctgtttc tggtcgcaac cgcaaccggc | 60 |
| gtgcactccg acactgtgct gacacagtcc ccaagcctgg ctgtttcacc tggtgaaaga | 120 |
| gctaccatca gttgtcgggc tagcgaaagc gtgtcaactc tgatgcactg gtaccagcag | 180 |
| aagcctggcc aacagcccaa actgctgata tatctggcat cacatcgtga gtccggagta | 240 |
| cctgctaggt tctctgggag cggcagcggc accgacttta ccctgacaat cgaccccatg | 300 |
| gaggccgaag atacagctac ttactactgc aacagtctag aaacgatccc atggactttt | 360 |
| ggacaaggga ccaaattgga gcttaagcgt acggtggctg caccatctgt cttcatcttc | 420 |
| ccgccatctg atgagcagtt gaaatctgga actgcctctg ttgtgtgcct gctgaataac | 480 |
| ttctatccca gagaggccaa agtacagtgg aaggtggata acgccctcca atcgggtaac | 540 |
| tcccaggaga gtgtcacaga gcaggacagc aaggacagca cctacagcct cagcagcacc | 600 |
| ctgacgctga gcaaagcaga ctacgagaaa cacaaagtct acgcctgcga agtcacccat | 660 |
| cagggcctga gctcgcccgt cacaaagagc ttcaacaggg gagagtgtta g | 711 |

<210> SEQ ID NO 39
<211> LENGTH: 1431
<212> TYPE: DNA
<213> ORGANISM: Artificial
<220> FEATURE:
<223> OTHER INFORMATION: huEGFR-8 HC polynucleotide

<400> SEQUENCE: 39

| | |
|---|---|
| aagcttgcca ccatgggctg gtcatgcatc atcttgtttt tggtggcaac tgccactggt | 60 |
| gtccattctc aagtacagct tgtacagtca ggtgctgaag tcgtcaagcc cggggccagt | 120 |
| gtcaagctgt cctgtactac atctggattt acaataaaag acacctacat tcactgggtg | 180 |
| aagaagaggc ccgggcaggg gctggagtgg attggccgga ttgatcccac aaatggcaac | 240 |
| aataaatatg accagaaatt ccaaggcaaa gccaccatca ctgcagatac ctcaagtaac | 300 |
| actgcttacc tgcagttgtc ttctctgaca tccgaggata cagccgtgta ctactgcact | 360 |
| agagaggatg gatacagata tgacgactgg tacttcgatg tgtggggcca ggggaccctg | 420 |
| gtcactgttt cctccgcttc cacaaagggc ccatcagttt tccccttggc tccaagttct | 480 |
| aaatccacaa gcgtggaac agctgcactg ggatgcctcg ttaaagatta tttccctgag | 540 |
| cctgtgacag tgagctggaa tagcggagca ttgacttcag gtgtgcacac tttttcccgct | 600 |
| gtgttgcagt cctccggtct gtactcactg tccagtgtcg taaccgtccc ttctagcagc | 660 |
| ttgggaaccc agacctacat ctgtaacgtc aaccataaac catccaacac aaaggtggat | 720 |
| aagaaggttg aaccaaagag ctgtgataag acacatacat gccctccttg tcctgcacca | 780 |
| gagctcctcg gaggtccatc tgtgttcctg tttccccca acccaaagga cactcttatg | 840 |
| atctctcgta ctccagaggt cacctgtgtt gttgtcgacg tgagccatga agatcccgag | 900 |
| gttaaattca ctggtacgt ggatggagtc gaggttcaca atgccaagac caagcccagg | 960 |
| gaggagcaat ataattctac atatcgggta gtgagcgttc tgaccgtgct ccaccaagat | 1020 |
| tggctcaatg gaaaagagta caagtgcaag gtgtccaaca aggctcttcc cgctcccatt | 1080 |
| gagaaaacta tctccaaagc caaggggcag ccacggaac cccaggtgta cattgccc | 1140 |
| ccatctagag acgagctgac caagaaccag gtgagtctca cttgtctggt caagggggttt | 1200 |
| tacccttctg acattgctgt agagtgggag tctaacggac agccagaaaa caactacaag | 1260 |
| acaactcccc cagtgctgga cagcgacggg agcttcttcc tctactccaa gttgactgta | 1320 |
| gacaagtcta gatggcagca aggaaacgtt ttctcctgct cagtaatgca tgaggctctg | 1380 |

```
cacaatcact atacccagaa atcactgtcc cttagcccag ggtgactcga g        1431
```

<210> SEQ ID NO 40
<211> LENGTH: 711
<212> TYPE: DNA
<213> ORGANISM: Artificial
<220> FEATURE:
<223> OTHER INFORMATION: huEGFR-8 LC polynucleotide

<400> SEQUENCE: 40

```
gaattcgcca ccatggggtg gtcctgtatc attctgtttc tggtagccac agctaccggc    60
gtgcactccg acatcgtgct gacacaatcc cctgctttta tgtcagcttc tccaggagag   120
aaagtgacca tgacctgctc tgcctctagc tctgtgtcct acatgcactg gtatcagcag   180
aagccagacc agagtcctaa agatggatc tacgctacca gtaaactggc ttctggcgtg    240
ccatctcggt tttcaggaag cggcagcggg accgactact cattgacaat atcctctatg   300
gaggccgaag acgctgcaac atactactgt cagcagtgga gctcaaatcc actcacattc   360
ggacagggta caaaactgga gctgaagcgt acggtggctg caccatctgt cttcatcttc   420
ccgccatctg atgagcagtt gaaatctgga actgcctctg ttgtgtgcct gctgaataac   480
ttctatccca gagaggccaa agtacagtgg aaggtggata cgccctcca atcgggtaac    540
tcccaggaga gtgtcacaga gcaggacagc aaggacagca cctacagcct cagcagcacc   600
ctgacgctga gcaaagcaga ctacgagaaa cacaaagtct acgcctgcga agtcacccat   660
cagggcctga gctcgcccgt cacaaagagc ttcaacaggg gagagtgtta g             711
```

<210> SEQ ID NO 41
<211> LENGTH: 32
<212> TYPE: DNA
<213> ORGANISM: Artificial
<220> FEATURE:
<223> OTHER INFORMATION: EcoMH1 primer
<220> FEATURE:
<221> NAME/KEY: misc_feature
<222> LOCATION: (18)..(18)
<223> OTHER INFORMATION: n is a, c, g, or t

<400> SEQUENCE: 41

```
cttccggaat tcsargtnma gctgsagsag tc                                   32
```

<210> SEQ ID NO 42
<211> LENGTH: 35
<212> TYPE: DNA
<213> ORGANISM: Artificial
<220> FEATURE:
<223> OTHER INFORMATION: EcoMH2
<220> FEATURE:
<221> NAME/KEY: misc_feature
<222> LOCATION: (18)..(18)
<223> OTHER INFORMATION: n is a, c, g, or t

<400> SEQUENCE: 42

```
cttccggaat tcsargtnma gctgsagsag tcwgg                                35
```

<210> SEQ ID NO 43
<211> LENGTH: 36
<212> TYPE: DNA
<213> ORGANISM: Artificial
<220> FEATURE:
<223> OTHER INFORMATION: BamIgG1 primer

<400> SEQUENCE: 43

```
ggaggatcca tagacagatg ggggtgtcgt tttggc                              36

<210> SEQ ID NO 44
<211> LENGTH: 31
<212> TYPE: DNA
<213> ORGANISM: Artificial
<220> FEATURE:
<223> OTHER INFORMATION: SacIMK

<400> SEQUENCE: 44
ggagctcgay attgtgmtsa cmcarwctmc a                                   31

<210> SEQ ID NO 45
<211> LENGTH: 46
<212> TYPE: DNA
<213> ORGANISM: Artificial
<220> FEATURE:
<223> OTHER INFORMATION: HindKL primer

<400> SEQUENCE: 45
tatagagctc aagcttggat ggtgggaaga tggatacagt tggtgc                   46
```